(12) United States Patent
Jolly et al.

(10) Patent No.: US 9,663,834 B2
(45) Date of Patent: May 30, 2017

(54) RETROVIRUS DETECTION

(75) Inventors: Douglas J. Jolly, Encinitas, CA (US); Omar Perez, San Diego, CA (US); Amy Lin, San Diego, CA (US)

(73) Assignee: Tocagen Inc., San Diego, CA (US)

( * ) Notice: Subject to any disclaimer, the term of this patent is extended or adjusted under 35 U.S.C. 154(b) by 169 days.

(21) Appl. No.: 13/810,403

(22) PCT Filed: Jul. 16, 2011

(86) PCT No.: PCT/US2011/044296
§ 371 (c)(1),
(2), (4) Date: Mar. 29, 2013

(87) PCT Pub. No.: WO2012/009711
PCT Pub. Date: Jan. 19, 2012

(65) Prior Publication Data
US 2013/0266931 A1    Oct. 10, 2013

Related U.S. Application Data

(60) Provisional application No. 61/365,297, filed on Jul. 16, 2010, provisional application No. 61/386,941, filed on Sep. 27, 2010, provisional application No. 61/391,360, filed on Oct. 8, 2010.

(51) Int. Cl.
*C07H 21/04* (2006.01)
*C12Q 1/70* (2006.01)

(52) U.S. Cl.
CPC ............. *C12Q 1/702* (2013.01); *C12Q 1/701* (2013.01); *C12N 2740/13011* (2013.01); *C12N 2799/027* (2013.01)

(58) Field of Classification Search
None
See application file for complete search history.

(56) References Cited

U.S. PATENT DOCUMENTS

| 2010/0167268 A1 | 7/2010 | Mikovits et al. | |
| 2010/0184015 A1* | 7/2010 | Silverman | C12Q 1/6886 435/5 |

FOREIGN PATENT DOCUMENTS

| WO | 2006/110489 A2 | 10/2006 |
| WO | 2010/075414 A2 | 7/2010 |
| WO | 2012058637 A2 | 5/2012 |

OTHER PUBLICATIONS

Buck, G. et al., "Design strategies and performance of custom DNA sequencing primers", 1999, Biotechniques, vol. 27: pp. 528-536.*
Becamel, Philippe, International Preliminary Report on Patentability, The International Bureau of WIPO, Jan. 31, 2013.
Erlwein et al., "Failure to detect the novel retrovirus XMRV in chronic fatigue syndrome," PLoS One, Jan. 6, 2010, p. e8519, vol. 5, No. 1.
Urisman et al., "Identification of a novel gammaretrovirus in prostate tumors of patients homozygous for R462Q RNASEL variant," PLoS Pathogens, Mar. 2006, p. 325, vol. 2, No. 3.
Lee, Hyun Ji, International Search Report and Written Opinion, Korean Intellectual Property Office, PCT/US2011/044296, Mar. 28, 2012.
Lo et al., "Detection of MLV-related virus gene sequences in blood of patients with chronic fatigue syndrome and healthy blood donors", Proceedings of the National Academy of Sciences, vol. 7, No. 36, Sep. 7, 2010, pp. 15874-15879.
Lombardi et al., "Detection of an infectious retrovirus, XMRV, in blood cells of patients with chronic fatigue syndrome", Science, American Association for the Advancement of Science, U.S.; U.S. National Library of Medicine (NLM), Bethesda, MD, U.S., vol. 326, No. 5952, Oct. 23, 2009, pp. 585-589.
Phane et al., "Disease-associated XMRV sequences are consistent with laboratory contamination", Retrovirology, Biomed Central Ltd., London, GB, vol. 7, No. 1, Dec. 20, 2010, p. 111.
Robinson et al., "No Evidence of XMRV or MuLv Sequences in Prostate Cancer, Diffuse Large B-Cell Lymphoma, or the UK Blood Donor Population", Advances in Virology, vol. 2011, Jan. 1, 2011, pp. 1-6.
Schmitt, Anja, European Patent Application No. EP11807616, Supplementary European Search Report, Oct. 17, 2013.
Office Action issued in Chinese Patent Application No. 201180044680.1, Sep. 24, 2014.
Arnold, R.S. e t al., "XMRV Infection in Patients with Prostate Cancer: Novel Serologic Assay and Correlation with PCR and FISH", Urology, vol. 75, No. 4, Apr. 1, 2010.
Baptista Cassio S et al., "Viral microarray oligonucleotide sequence SEQ ID No. 11", Database Geneseq [Online] Jul. 10, 2008, XP002739251, retrieved from EBI Accession No. GSN:AQX99908; Database Accession No. AQX99908 and WO 2007/130519 A2, Nov. 15, 2007.
Chen, Yin, "Oligonucleotide of the invention 3'-E/S/P/P-LINKER", Database Geneseq [Online], Sep. 9, 2004, retrieved from EBI Accession No. GSN:ADP67227; Database Accession No. ADP67227 and WO 2004/052297.
Dong et al., "From the Cover: An infectious retrovirus susceptible to an IFN antiviral pathway from human prostate tumors", Proceedings of the National Academy of Sciences, vol. 104, No. 5, Jan. 30, 2007.
Dubensky, JR Thomas W. et al., "Moloney murine leukaemia virus LTR PCT primer SEQ ID No. 16", Database Geneseq [Online], May 22, 2000, XP002739249, retrieved from EBI Accession No. GSN:AAZ92907; Database Accession No. AAZ92907 and U.S. Pat. No. 6,015,694 A, Jan. 18, 2000.
Erlwein et al., "Failure to Detect the Novel Retrovirus XMRV in Chronic Fatigue Syndrome", POLS One, vol. 5, No. 1, Jan. 6, 2010.
Fischer N., et al., "Prevalence of human gammaretrovirus XMRV in sporadic prostate cancer", Journal of Clinical Virology, vol. 43, No. 3, Nov. 1, 2008.
Hohn, Oliver et al., "Lack of evidence for xenotropic murine leukemia virus-related virus (XMRV) in German prostate cancer patients", Retrovirology, vol. 6, No. 1, Oct. 16, 2009.

(Continued)

*Primary Examiner* — Michael Burkhart
(74) *Attorney, Agent, or Firm* — Gavrilovich, Dodd & Lindsey LLP

(57) ABSTRACT

Provided are methods and compositions useful for detecting viral infection or contamination in a biological sample.

30 Claims, 21 Drawing Sheets

(56) References Cited

OTHER PUBLICATIONS

Lombardi et al., "Detection of an infectious retrovirus, XMRV, in blood cells of patients with chronic fatigue syndrome", Science, vol. 326, No. 5952, Oct. 23, 2009.
Schlaberg et al., "XMRV is present in malignant prostatic epithelium and is associated with prostate cancer, especially high-grade tumors", Proceedings of the National Academy of Sciences, vol. 106, No. 38, Sep. 22, 2009.
Schmitt, Anja, Extended European Search Report, European Patent Application No. 14191299.8, May 18, 2015.
Viromed Ltd., "pGEM T easy-3dLTR3 DNA amplifying PCR primer 3LTR-3, SEQ ID:9", Database Geneseq [Online] Jan. 22, 2009, XP002739250, retrieved from EBI Accession No. GSN:ATS37006; Database Accession No. ATS37006 and KR 20080032562 A, Apr. 15, 2008.

* cited by examiner

```
Query  230   ACAGTTCCCGCCT{XXXXXXXXXXXXXXXXXXXXXXX}-TTTGGGACCGAAGCCGCGCCGCGC   288
             ||| |||||||||   ||||||||||||||||||||| ||| | ||||| ||||||||||||
Sbjct  486   ACACTTCCCGCCCCCGTCTGAATTTTTGCTTTCGGTTTTACG-CCGAAACCGCGCCGCGC   544

Query  289   GTCTTG-TCTG--CTGCAG--CATC-GTTCTGT-GTT-GTCTCTGTCTGACTGTGTTTCT   340
             ||| || | ||   ||   : | || ||||| | ||| |||  ||| | |   |||| |||
Sbjct  545   GTC-TGATTTGTTTTGTTGTTCTTCTGTTCT-TCGTTAGT-T-T-TCT-TCTGTCTTTAA   598

Query  341   GTATTTGTCTGAGAAT-ATGGGCCAGACTGTTACCACTCCCT-TAACTTTGACCTTAG--   396
             ||  || ||  ||| || ||:|||  ||||| || || || |||| | ||| | ||||||  |
Sbjct  599   GT-GTTCTC-GAG-ATCATGGGACAGACCGTAACTAC-CCCTCTGAGTCTAACCTT-GCA   653

Query  397   GTCACTGGAAAGATGTCGAGCGGATCGC-TCACAACCAGTCGGTAGATGTCAAGAAGAGA   455
             |  ||||||   ||||||| |||| || || || || |||||||||  || ||||:|||||||||
Sbjct  654   G-CACTGGGGAGATGTCCAGCGCATTGCATC-CAACCAGTCTGTGGATGTCAAGAAGAGG   711

Query  456   CGTTGGGTTACCTTCTGCTCTGCAGAATGGCCAACCTTT-AACGTCGGATGGCCGCGA-G   513
             || ||||||||||:|||| |||:||| ||||||||||:||| | ||||| ||| || ||| | |
Sbjct  712   CGCTGGGTTACCTTCTGTTCCGCCGAATGGCCAA-CTTTCAATGTAGGATGGCCTC-AGG   769

Query  514   ACGGCACCTTTAACCGAGACCTCATCACCCAGGTTAAGATCAAG-CTCTTTTCACCTGG-   571
             | || || |||||    || | ||| | ||||| ||| || || || || || || |||| |||||
Sbjct  770   ATGGTACTTTTAATTTAGGTGTTATCTCTCAGGTCAAG-TCTAGAGTGTTTTGTCCTGGT   828

Query  572   CCCGCATGGACACCCAGACCAGGTCCCCTACATCGTGACCTGGGAAGC-CTTGGCTTTTG   630
             ||| || ||||||||| || ||||||||  || ||||| |||||||| |:|||| ||| || | ||
Sbjct  829   CCC-CACGGACACCCGGATCAGGTCCCATATATCGTCACCTGGGAGGCACTT-GCCTATG   886

Query  631   ACCCCCCTCCCTGGGTCAAGCCCTTTGTACAC-CCTAAGCCTCCGCCTCCTCTTCCTCCA   689
             ||||||| |||| ||||||:||| || |||| || ||||| | || ||| | |||| || | |
Sbjct  887   ACCCCCCTCCGTGGGTCAAACCGTTTGT-CTCTCCTAA-AC-CC-CCTCCT-TTAC-CGA   940

Query  690   TCCGC-CCCGTCTCTCCC-CCTTGAACCTCCTCGTTCGACC-CCG-CCTCGATCCT-CCC   744
             | || |||||||| |||||  || || | ||| | ||| |||  |||  ||||| |||| | |||
Sbjct  941   -CAGCTCCCGTC-CTCCCGCC-CGGTCCTTCT-GCGCAACCTCCGTCC-CGAT-CTGCCC   994

Query  745   TTTATCCAGCCCTCACTCCTTCTCT-AGGCGCCAAA---CCTAAACCTCAAGTTCTTTCT   800
             |||| || ||||| || || ||| | | |||||  |||||     ||||| || || ||||| ||
Sbjct  995   TTTACCCTGCCCTTACCCCCTCTATAAAG-TCCAAACCTCCTAAGCCCCAGGTTCTCCCT   1053

Query  801   GACAGTGGGGGCCGCTCATCGACCTACTTACAGAAGACCCCCGCCTTATAGGGACCCA   860
             || || || || || ||||| ||||||| |||||||| ||||||||   |||| || || |||
Sbjct  1054  GATAGCGGCGGACCTCTCATTGACCTTCTCACAGAGGATCCCCCGCC--GTACGGA-GCA   1110

Query  861   -AGACC-ACCCCCTTCCGACAGGGACGGA-AATGGTGGAGAAGC-G---ACC-CCTGCGGG   913
              | ||| || || || | ||||||| | || ||| | |||| ||| |   ||| |||| |
Sbjct  1111  CA-ACCTTCCTCC-TCTGCCAGGGA-GAACAATGAAGAAGAGGCGGCCACCACCT-C-CG   1165

Query  914   AGAGGCACCGGACCCC-TC-CCCAATGGCATCTCGCCTACGTGGGAGACGG-GAG-CCC-   968
             || |   ||   |||| ||  |||  || |||| ||||| || ||| |||| || ||| |||
Sbjct  1166  AG-GTTTCC--CCCCCTTCTCCC-ATGGTGTCTCGACTGCG-GGGA-A-GGAGAGACCCT   1218

Query  969   CCTGTGGCCGACTCCACTACCTCGCAGGCATTCCCCCTCCGCGCAGGAGGAAACGGACAG   1028
             ||  | || |||||||||  ||||||| |||||||  ||| | ||| | || |||
Sbjct  1219  CCCGCAGCGGACTCCACCACCTCCCAGGCATTCCCACTCCGCATGGGGGAGATGGCCAG   1278
```

FIGURE 5

```
Query  1029  CTTCAATACTGGCCGTTCTCCTCTTCTGACCTT-TACAACTGGAAAAATAATAACCCTTC  1087
             |||| ||||||||||||| ||||| |||||  || || || ||||||||||||||||||
Sbjct  1279  CTTCAGTACTGGCCGTTTTCCTCCTCTGA-TTTATATAATTGGAAAAATAATAACCCTTC  1337

Query  1088  TTTTTCTGAAGATCCAGGTAAACTGACAG-CTCTGATCGAGTCTGTTCTCATCACCCATC  1146
             |||||||||||||||||||||| ||||   |||| ||||| |||||| ||| ||||||
Sbjct  1338  CTTTTCTGAAGATCCAGGTAAATTGACGGCCT-TGATTGAGTCCGTCCTCATCACCCACC  1396

Query  1147  AGCCCACCTGGGACGACTGTCAGCAGCTGTTGGGACTCTGCTGACCGGAGAAGAAAAAC  1206
             ||||||||||||||||||||||||||  |||||||||| |||||||||||||||||| |
Sbjct  1397  AGCCCACCTGGGACGACTGTCAGCAGTTGTTGGGACCCTGCTGACCGGAGAAGAAAAGC  1456

Query  1207  AACGGGTGCTCTTAGAGGCTAGAAAGGCGGTGCGGGGCGATGATGGGCGCCCCACTCAAC  1266
             | ||||||||| |||||||||||||||| || ||||| ||||||||| ||||||||| |
Sbjct  1457  AGCGGGTGCTCCTAGAGGCTAGAAAGGCAGTCCGGGCAATGATGGACGCCCCACTCAGT  1516

Query  1267  TGCCCAATGAAGTCGATGCCGCTTTTCCCCTCGAGCGCCCAGACTGGGATTACACCAC-C  1325
             |||| ||||||||| ||| ||||||||||| ||||||| | |||||||||||||||| |
Sbjct  1517  TGCCTAATGAAGTCAATGCTGCTTTTCCCCTTGAGCGCCCCGATTGGGATTACACCACTA  1576

Query  1326  CAGGCAGGTAGGAACCACCTAGTCCACTATCGCCAGTTGCTCCTAGCGGGTCTCCAAAAC  1385
             || | ||||||||||||||||||||  || ||||||||||||||||||||||||||||
Sbjct  1577  CA-GAAGGTAGGAACCACCTAGTCCTCTACCGCCAGTTGCTCTTAGCGGGTCTCCAAAAC  1635

Query  1386  GCGGGCAGGAGCCCCACCAATTTGGCCAAGGTAAAAGCAATAACACAAGGC-CCCAATGA  1444
             |||||||||||||||||||||||||||||||||||| ||||| | |||| || |||||
Sbjct  1636  GCGGGCAGGAGCCCCACCAATTTGGCCAAGGTAAAAGGGATAAC-CCAGGGACCTAATGA  1694

Query  1445  GTCTCCCTCGGCCTTCCTAGAGAGACTTAAGGAAGCCTATCGCAGGTACACTCCTTATGA  1504
             ||||||||| ||||| |||||||||||||||||| |||||| |||||||||||||||||
Sbjct  1695  GTCTCCCTCAGCCTTTTTAGAGAGACTCAAGGAGGCCTATCGCAGGTACACTCCTTATGA  1754

Query  1505  CCCTGAGGACCCAGGGCAAGAAACTAATGTGTCTATGTCTTTCATTTGGCAGTCTGCCCC  1564
             ||||||||||||||||||||||| |||||||| ||||| ||||| |||||||||||||
Sbjct  1755  CCCTGAGGACCCAGGGCAAGAAACCAATGTGTCCATGTCATTCATCTGGCAGTCTGCCCC  1814

Query  1565  AGACATTGGGA-GAAAGTTAGAGAGGTTAGAAGATTTAAAAAACAAGACGCTT-GGAGAT  1622
             || || ||| | |||||||||||| |||||||||||||||| | |||||| ||| |||||
Sbjct  1815  GGATATCGG-ACGAAAGTTAGAGCGGTTAGAAGATTTAAAGAGCAAGAC-CTTAGGAGAC  1872

Query  1623  TTGGTTAGAGAGGCAGAAAAGATCTTTAATaas                            1682
             || || || || || ||||||||||||||||  ||||||||||||||||||||||||||
Sbjct  1873  TTAGTGAGGGAAGCTGAAAAGATCTTTAATAAGCGAGAAACCCCGGAAGAAAGAGAGGAA  1932

Query  1683                  -                             acagaggatyagcagaaa  1742
             |||||||||||||||  |||||||||||||||||||||||||  |||||||||||||| |
Sbjct  1933  CGTATCAGGAGAGAAATAGAGGAAAAAGAAGAACGCCCTAGGGCAGAGGATGAGCAGAGA  1992

Query  1743  gagasagaaagage TCGTAGGAGACATAGAGAGATGAGCAAGCTATTGGCCACTGTCGTT  1802
             ||| | |||||| | ||||||  |  || ||||||||||||||||||||||||||||
Sbjct  1993  GAGAGAGAAAGGGACCGCAGAAGACATAGAGAGATGAGCAAGCTCTTGGCCACTGTAGTT  2052

Query  1803  AGTGGACAGAAACAGGATAGACAGGGAGGAGAACGAACGAGGTCCCAACTCGATC-GCGA  1861
             | ||| |||| ||||||||||||||| ||||| ||||| |||||| ||| ||| |  |
Sbjct  2053  ATTGGTCAGAGACAGGATAGACAGGGGGGAGAGCGGAGGAGGCCCCAACTTGATAAG-GA  2111
```

FIGURE 5 (cont'd)

```
Query  1862  CCAGTGTGCCTACTGCAAAGAAAAGGGGCACTGGGCTAAAGATTGTCCCAA-GAAACCAC  1920
             ||| ||  ||||||||||||||||||| ||||||||||||| || || ||||| ||| ||||
Sbjct  2112  CCAATGCGCCTACTGCAAAGAAAAGGGACACTGGGCTAAGGACTG-CCCAAAGAAGCCAC  2170

Query  1921  GAGGACCTCGGGGACCAAGACCCCAGACCTCCCTCCTGACCCTAGATGACTAGGGAGGTC  1980
             |||| || || |||||| ||  ||||||||||||||||||||| ||| |||||||||||||
Sbjct  2171  GAGGGCCCCGAGGACCGAGGCCCCAGACCTCCCTCCTGACCTTAGGTGACTAGGGAGGTC  2230

Query  1981  AGGGTCAGGAG          TGAACCCAGGATAACCCTCAAAGTCGGGGGGCAACCCGTCA  2040
             |||||||||||          |||||||||||||||||||||||||||||||||||||||
Sbjct  2231  AGGGTCAGGAGCCCCCCCCTGAACCCAGGATAACCCTCAAAGTCGGGGGGCAACCCGTCA  2290

Query  2041  CCTTCCTGGTAGATACTGGGGCCAACACTCCGTGCTGACCCAAAATCCTGGACCCCTAA  2100
             |||||||||||||||||||||||||||||||||||||||||||||||||||||||||||
Sbjct  2291  CCTTCCTGGTAGATACTGGGGCCCAACACTCCGTGCTGACCCAAAATCCTGGACCCCTAA  2350

Query  2101  GTGATAAGTCTGCCTGGGTCCAAGGGGCTACTGGAGGAAAGCGGTATCGCTGGACCACGG  2160
             ||||  ||||||||||||||||||||||||||||||||||||||||||||||||||||||
Sbjct  2351  GTGACAAGTCTGCCTGGGTCCAAGGGGCTACTGGAGGAAAGCGGTATCGCTGGACCACGG  2410

Query  2161  ATCGCAAAGTACATCTAGCTACCGGTAAGGTCACCCACTCTTTCCTCCATGTACCAGACT  2220
             |||||||||||||||  |||||||||||||||||||||||||||||||||||||||||||
Sbjct  2411  ATCGCAAAGTACATCTGGCTACCGGTAAGGTCACCCACTCTTTCCTCCATGTACCAGACT  2470

Query  2221  GTCCCTATCCTCTGTTAGGAAGAGATTTGCTGACTAAAACTAAAAGCCCAAATCCACTTTG  2280
             |   ||||||||||| |||||||||| |||||||||||||||||||||||||||||||||
Sbjct  2471  GCCCCTATCCTCTGCTAGGAAGAGACTTGCTGACTAAACTAAAAGCCCAAATCCACTTTG  2530

Query  2281  AGGGATCAGGAGCTCAGGTTATGGGACCAATGGGGCAGCCCCTGCAAGTGTTGACCCTAA  2340
             ||||||||||||||||||    |||||||||||||||||||||||||||||| |||| ||
Sbjct  2531  AGGGATCAGGAGCTCAGGTTGTGGGACCGATGGGACAGCCCCTGCAAGTGCTGACAGTAA  2590

Query  2341  ATATAGAAGATGAGCATCGGCTACATGAGACCTCAAAAGAGCCAGATGTTTCTCTAGGGT  2400
             |  ||||||||||| || |||||||||  |||||||||||||||||||||  |||||||||
Sbjct  2591  ACATAGAAGATGAGTATTGGCTACATGATACCAGGAAAGAGCCAGATGTTCCTCTAGGGT  2650

Query  2401  CCACATGGCTGTCTGATTTTCCT-CAGCCCTGGGCGGAAACCGGGGGCATGGGACTGGCA  2459
             |||||||||| ||||||||  ||| ||||||||||||||||||||||||||||||||||
Sbjct  2651  CCACATGGCTTTCTGATTT-CCTTCAGGCCTGGGCGGAAACCGGGGGCATGGGACTGGCA  2709

Query  2460  GTTGCCAAGCTCCTCTGATCATACCTCTGAAGGCAACCTCTACCCCGTGTCCATAAAA  2519
             |||||||||||||||||||||||||||||||||||||||||||||||||||||||||
Sbjct  2710  GTTCGCCAAGCTCCTCTGATCATACCTCTGAAGGCAACCTCTACCCCCGTGTCCATAAAA  2769

Query  2520  CAATACCCCATGTCACAAGAAGCCAGACTGGGATCAAGCCCCACATACAGAGACTGTTG  2579
             ||||||||||||||||||||||||||||||||||||||||||||||||||||| ||||||
Sbjct  2770  CAATACCCCATGTCACAAGAAGCCAGACTGGGATCAAGCCCCACATACAGAGGCTGTTG  2829

Query  2580  GACCAGGGAATACTGGTACCCTGCCAGTCCCCCTGGAACACGCCCCTGCTACCCGTTAAG  2639
             |||||||||||||||||||||||||||||||||||||||||||||||||||||||||||
Sbjct  2830  GACCAGGGAATACTGGTACCCTGCCAGTCCCCCTGGAACACGCCCCTGCTACCCGTTAAG  2889

Query  2640  AAACCAGGGACTAATGATTATAGGCCTGTCCAGGATCTGACACAAGTCAACAAGCGGGTG  2699
             ||||||||||||||||||||||||||||||||||||||||||||||||||||||||||||
Sbjct  2890  AAACCAGGGACTAATGATTATAGGCCTGTCCAGGATCTGAGAGAAGTCAACAAGCGGGTG  2949
```

FIGURE 5 (cont'd)

```
Query  2700  GAAGACATCCACCCCACCGTGCCCAACCCTTACAACCTCTTGAGCGGGCTCCCACCGTCC  2759
             ||||||||||||||||||||||||||||||||||||||||||||||||||||||||||||
Sbjct  2950  GAAGACATCCACCCCACCGTGCCCAACCCTTACAACCTCTTGAGCGGGCTCCCACCGTCC  3009

Query  2760  CACCAGTGGTACACTGTGCTTGATTTAAAGGATGCCTTTTCTGCCTGAGACTCCACCCC   2819
             ||||||||||||||||||||||||||||||||||||||||||||||||||||||||||
Sbjct  3010  CACCAGTGGTACACTGTGCTTGATTTAAAGGATGCCTTTTTCTGCCTGAGACTCCACCCC  3069

Query  2820  ACCAGTCAGCCTCTCTTCGCCTTTGAGTGGAGAGATCCAGAGATGGGAATCTCAGGACAA  2879
             ||||||||||||||||||||||||||||||||||||||||||||||||||||||||||||
Sbjct  3070  ACCAGTCAGCCTCTCTTCGCCTTTGAGTGGAGAGATCCAGAGATGGGAATCTCAGGACAA  3129

Query  2880  TTGACCTGGACCAGACTCCCACAGGGTTTCAAAAACAGTCCCACCCTGTTTGATGAGGCA  2939
             ||||||||||||||||||||||||||||||||||||||||||||||||||||||||||||
Sbjct  3130  CTGACCTGGACCAGACTCCCACAGGGTTTCAAAAACAGTCCCACCCTGTTTGATGAGGCA  3189

Query  2940  CTGCACAGAGACCTAGCAGACTTTCCGGATCCAGCACCCAGACTTGATCCTGCTACAGTAC  2999
             |||||||||||||||||||    |||||||||||||||||||||||||||||||||||||
Sbjct  3190  CTGCACAGAGACCTAGCAGATTTCCGGATCCAGCACCCAGACTTGATCCTGCTACAGTAC  3249

Query  3000  GTGGATGACTTACTGCTGCCGCCACTTCTGAGCTAGACTGCCAACAAGGTACTCGGGCC   3059
             |||||||||||||||||||||||||||||||||   ||||||||||  ||||||||||
Sbjct  3250  GTGGATGACTTACTGCTGCCGCCACTTCTGAGCAAGACTGCCAACGAGGTACTCGGGCC  3309

Query  3060  CTGTACAAACCCTAGGGAACCTCGGGTATCGGGCCTCGGCCAAGAAAGCCCAAATTTGC  3119
             ||  ||||||||||||||||||||||||||||||  ||||||||||||||||||||||
Sbjct  3310  CTATTACAAACCCTAGGGAACCTCGGGTATCGGGCCTCGGCCAAGAAAGCCCAAATTTGC  3369

Query  3120  CAGAAACAGGTCAAGTATCTGGGGTATCTCTAAAAGAGGGTCAGAGATGGCTGACTGAG  3179
             ||||||||||||||||||||||||||||||  |||||||||||||||||||||||||||
Sbjct  3370  CAGAAACAGGTCAAGTATCTGGGGTATCTCCTAAAAGAGGGACAGAGATGGCTGACTGAG  3429

Query  3180  GCCAGAAAAGAGACTGTGATGGGGCAGCCTACTCCGAAGACCCCTCGACAACTAAGGGAG  3239
             ||||||||||||||||||||||||||||||||||||||||||||||||||||||||||||
Sbjct  3430  GCCAGAAAAGAGACTGTGATGGGGCAGCCCACTCCGAAGACCCCTCGACAACTAAGGGAG  3489

Query  3240  TTCCTAGGGACGGCAGGCTTCTGTCGCCTCTGGATCCCTGGGTTTGCAGAAATGGCAGCC  3299
             ||||||||||||||||||||||||||||||||||||||||||||||||||||||||||||
Sbjct  3490  TTCCTAGGGACGGCAGGCTTCTGTCGCCTCTGGATCCCTGGGTTTGCAGAAATGGCAGCC  3549

Query  3300  CCCTTGTACCCTCTCACCAAAACGGGGACTCTGTTTAATTGGGGCCCAGACCAGCAAAAG  3359
             ||||||||||||||   |||||||||||||||||||||||||||||||||||  ||||||
Sbjct  3550  CCCTTGTACCCTCTTACCAAAACGGGGACTCTGTTTAATTGGGGCCCAGACCAGCAAAAG  3609

Query  3360  GCCTATCAAGAAATCAAGCAAGCTCTTCTAACTGCCCCAGCCCTGGGGTTGCAGATTTG  3419
             |||||||||||||||||  ||  ||||||||||||||||  |||||||||||||||||
Sbjct  3610  GCCTATCAAGAAATCAAACAGGCTCTTCTAACTGCCCCCGCCCTGGGATTGCAGATTTG  3669

Query  3420  ACTAAGCCCTTGAACTCTTTGTCGACGAGAAGCAGGGCTACGCCAAAGGTGTCCTAACG  3479
             ||||||||||||||||||||||||||||||||||||||||||||||||||||||||||
Sbjct  3670  ACTAAGCCCTTTGAACTCTTTGTCGACGAGAAGCAGGGCTACGCCAAAGGCGTCCTAACG  3729

Query  3480  CAAAAACTGGGACCTTGGCGTCGGCCGTGGCCTACCTGTCAAAAAGCTAGACCCAGTA   3539
             |||||||||||||||||||||||||||||||||||||||||||||||||||||||||
Sbjct  3730  CAAAAACTGGGACCTTGGCGTCGGCCTGTGGCCTACCTGTCCAAAAAGCTAGACCCAGTG  3789
```

FIGURE 5 (cont'd)

```
Query  3540  GCAGCTGGGTGGCCCCCTTGCCTACGGATGGTAGCAGCCATTGCCGTACTGACAAAGGAT  3599
             ||||||||||||||||||||||||||||||||||||||||||||||| ||||||||  ||
Sbjct  3790  GCAGCTGGGTGGCCCCCTTGCCTACGGATGGTAGCAGCCATTGCCGTTCTGACAAAAAAT  3849

Query  3600  GCAGGCAAGCTAACCATGGGACAGCCACTAGTCATTCTGGCCCCCCATGCAGTAGAGGCA  3659
             ||||||||||||||||| |||||||||||||||||||||||||||||||| ||||| |||
Sbjct  3850  GCAGGCAAGCTAACTATGGGACAGCCGCTAGTCATTCTGGCCCCCCATGCGGTAGAAGCA  3909

Query  3660  CTAGTCAAACAACCCCCCGACCGCTGGCTTTCCAACGCCCGGATGACTCACTATCAGGCC  3719
             || |||||||||||||| ||||| ||||||| ||||| |||||||| |||||||||||||
Sbjct  3910  CTGGTCAAACAACCCCCTGACCGTTGGCTATCCAATGCCCGCATGACCCACTATCAGGCA  3969

Query  3720  TTGCTTTTGGACACGGACCGGGTCCAGTTCGGACCGGTGGTAGCCCTGAACCCGGCTACG  3779
             |||| |||| || ||||||||||||||||||||||||||||| ||||| ||||||| ||
Sbjct  3970  ATGCTCCTGGATACAGACCGGGTTCAGTTCGGACCGGTGGTGGCCCTCAACCCGGCCACC  4029

Query  3780  CTGCTCCCACTGCCTGAGGAAGGGCTGCAACACA--ACTGCCTTGATATCCTGGCCGAAG  3837
             |||||||  || |  ||| ||  || ||  ||||    |||||| || || |||| || |
Sbjct  4030  CTGCTCCCCCTACCGGAA-AAGGAA-GCCCCCCATGACTGCCTCGAGATCTTGGCTGA-G  4086

Query  3838  CC-CACGGAACCCGACCCGACCTAACGGACCAGCCGC-TCCCAGACGCCGACCACACCTG  3895
             |  |||||||||| ||| |||| |||||||||||||| |  |||||||  ||| ||| ||
Sbjct  4087  ACGCACGGAACCAGACCGGACCTCACGGACCAGCC-CATCCCAGACGCTGATTACACTTG  4145

Query  3896  GTACACGGATGGAAGCAGTCT-CTTACAAGAGGGACAGCGTA-AGGCGGGAGCTGCGGTG  3953
             |||||| ||||||||| || | |||||||||||| || || |  ||  || || ||||||
Sbjct  4146  GTACACAGATGGAAGCAG-CTTCCTACAAGAAGGACAACGGACAG-CTGGAGCAGCGGTG  4203

Query  3954  ACCACCGAGACCGAGGTAATCTGGCTAAAGCCCTGCCAGCCGGGACATCCGCTCAGCGG  4013
             || || ||||||||||||||||||| |  || |||||  |||| |||| ||| || ||
Sbjct  4204  ACTACTGAGACCGAGGTAATCTGGGCGAGGGCTCTGCCGGCTGGAACATCCGCCCAACGA  4263

Query  4014  GCTGAACTGATAGCACTTACCCAGGCCCTAAAGATGCCAGAAGGTAAGAAGCTAAAACTT  4073
             ||   ||||||||||| ||||| ||||| |||||||| |||||| |||||| |||| |||
Sbjct  4264  GCCGAACTGATAGCACTCACCCAAGCCTTAAAGATGGCAGAAGGTAAGAAGCTAAATGTT  4323

Query  4074  TATACTGATAGCCGTTATGCTTTTGCTACTGCCCATATCCATGGAGAAATATACAGAAGG  4133
             || |||||||||| |||||||| ||||||| || ||||||||||||||||||||  |||
Sbjct  4324  TACACTGATAGCCGCTATGCCTTCGCCACGGCCCATGTCCATGGAGAAATATATAGGAGG  4383

Query  4134  CGTGGGTTGCTCACATCAGAAGGCAAAGAGATCAAAAATAAAGA-CGAGATCTTGGCCCT  4192
             || ||||||||| |||| |||||||| |||| ||||  ||| || |||| |||||| |||
Sbjct  4384  CGAGGGTTGCTGACCTCAGAAGGCAGAGAAATTAAAAACAA-GAACGAGATCTTGGCCTT  4442

Query  4193  ACTAAAAGCCCTCTTTCTGCCCAAAAGACTTAGCATAATCCATTGTCCAGGACATCAAAA  4252
             ||||||||| ||||||||||||||| |||||||| ||||| || ||||||||||||||||
Sbjct  4443  GCTAAAAGCTCTCTTTCTGCCCAAACGACTTAGTATAATTCACTGTCCAGGACATCAAAA  4502

Query  4253  GGGACACAGCGCCGAGGCTAGAGGCAACCGGATGGCTGACCAAGCGGCCCGAAAGGCAGC  4312
              ||  || || ||||||| ||||| ||||| || |||| ||||||||||| ||||||||
Sbjct  4503  AGGAAACAGTGCTGAGGCCAGAGGCAACCGTATGGCAGATCAAGCAGCCCGAGAGGCAGC  4562

Query  4313  CATCACAGAG-ACTCC-AGACACCTCTACCCTCCTCATAGAAAATTCATCACCC-TACAC  4369
             |||| | ||  || || ||| | ||||||||||||||||| | || ||||    ||||
Sbjct  4563  CATGA-AG-GCAGTTCTAGAAACCTCTACACTCCTCATAGAGGACTCAAC-CCCGTATAC  4619
```

FIGURE 5 (cont'd)

```
Query  4370  -C-TCAGAACATTTTCATTACACAGTGACTGATAT-AAAGGACCTAACC--AAGTTGCGG  4424
              | ||    ||||| ||||||||| ||  ||| |  ||| |||  ||         ||| |||
Sbjct  4620  GCCTCCC--CATTTCCATTACACCGAAACAGATCTCAAAAGAC-TA-CGGGAACT-GGGA  4674

Query  4425  GCCATTTATGATAAAACAAA-GAAGTATTGGGTC-TACCAAGGAAAACCTGTGATGCCTG  4482
              ||||  ||  ||   |  |   || | ||||||  ||| ||||  ||||||||||||  |
Sbjct  4675  GCCACCTACAATCAGACAAAAGGA-TATTGGGTCCTAC-AAGGCAAACCTGTGATGCCCG  4732

Query  4483  ACCAGTTTACT-TTTGAATTATTAGACTTTCTTCATCAG-CTGACTCACCTCAGCTTCTC  4540
              | ||||      |  ||  | ||   ||| || ||| || || | ||| ||  || |||
Sbjct  4733  ATCAGTCCG-TGTTTGAACTGTTAGACTCCCTACA-CAGACTCACCCATCTGAGCC-CTC  4789

Query  4541  AAAA-ATGAAGGCTCTCCTAGA--GAGAAGCCACAGTCCCTACTACATGCTGAACCGGGA  4597
              |||| ||||||| ||||| || ||   ||||||| | || ||||||||||||| ||||||||
Sbjct  4790  AAAAGATGAAGGCACTCCTCGACAGAGAAGA-A-AGCCCTACTACATGTTAAACCGGGA  4847

Query  4598  TC-GAAC-ACTCAAAAATATCACTGAGACCTGCAAAGCTTGTGCACAAGTCAACGCCAGC  4655
               | ||||  | ||   ||    ||||||||||||| || |||||| ||||| || ||||||
Sbjct  4848  -CACAACTA-TCCAGTATGTGACTGAGACCTGCACCGCCTGTGCCCAAGTAAATGCCAGC  4905

Query  4656  AA-GTCTGCCGTTAAA-CAGGGAA-CTAGGGTCCGCGGGCATCGGCCCGGCACTCATTGG  4712
              || | |    ||     |     ||  | ||||| |||||||| |||||  |||||||
Sbjct  4906  AAAGCCAAAA-TTGGGGCAGGGGTGCGAG--TACGCGGACATCGGCCAGGCACCCATTGG  4962

Query  4713  GA-GATCGATTTCACCGA-GATAAAGCCCGGATTGTATGGCTATAAATATCTTCTAGTTT  4770
              || | | |||||||| || ||   ||||||| ||| ||||| | ||| || |  ||||| |
Sbjct  4963  GAAGTT-CATTTCACGGAAC-TAAAGCCAGGACTGTATGGGTACAAGTACCTCCTAGTGT  5020

Query  4771  TTATAGATACCTTTCTGGCTGGATAGAAGCCTTCCCAACCAAGAAAGAAACCGCCAAGG  4830
              || |||| |||||| ||||||| || ||||| |||||| |||||     |||||  ||||||
Sbjct  5021  TTGTAGACACCTTCTCTGGCTGGGTAGAGGCATTCCCGACCAAGCGGGAAACTGCCAAGG  5080

Query  4831  TCGTAACCAAGAAGCTACTAGAGGAGATCTTCCCCAGGTTCGGCATGCCTCAGGTATTGG  4890
              ||||    ||||    ||||    |||| ||  ||  ||  || || || ||||| ||||||||
Sbjct  5081  TCGTGTCCAAAAAGCTGTTAGAAGACATTTTTCCGAGATTTGGAATGCCGCAGGTATTGG  5140

Query  4891  GAACTGACAATGGGCCTGCCTTCGTCTCCAAGGTGAGTCAGACAGTGGCCGATCTGTTGG  4950
              || |||| || |||||||||||||  || ||||  |||| |||| ||||||||||  |  |||
Sbjct  5141  GATCTGATAACGGGCCTGCCTTCGCCTCCCAGGTAAGTCAGTCAGTGGCCGATTTACTGG  5200

Query  4951  GGATTGATTGGAAATTACATTGTGCATACAGACCCCAAAGCTCAGGC               5010
              |||| ||||||||| |||||||||| | ||||||| ||||| ||||||
Sbjct  5201  GGATCGATTGGAAGTTACATTGTGCTTATAGACCCCAGAGTTCAGGACAGGTAGAAAGAA  5260

Query  5011              CATCAAGGAGACTTTAACTAAATTAACGCTTGCAACTGGCTCTAGAGACT  5070
              |||||||| || ||||||| || ||||||||||| ||||||||| ||| || ||||||||||
Sbjct  5261  TGAATAGAACAATTAAGGAGACTTTGACCAAATTAACGCTTGCATCTGGCACTAGAGACT  5320

Query  5071  GGGTG                        GTACCGAGCCCGCAACACGCCGGGCCCCATGGCC  5130
              ||||  ||||||||||||||          ||||||||| ||  || |  |||||  ||
Sbjct  5321  GGGTACTCCTACTCCCCTTAGCCCTCTACCGAGCCCGGAATACTCCGGGCCCCACGGAC  5380

Query  5131  TCACCCCATATGAGAT-CTTA                         AAACTTCCCTGACCCT  5189
              | || |  ||||| |  ||   |||||||||||||||||||  || || | ||| |||
Sbjct  5381  TGACTCCGTATGAAATTCTG-TATGGGGCACCCCCGCCCCTTGTCAATTTTCATGATCCT  5433
```

FIGURE 5 (cont'd)

```
Query  5190  GACATGACAAGAGTTA-CTAACAGCCCCCCTCTCCAAGCTCACTTACAGGCTCTCTACTT  5248
             || |||  ||| |||||  |||| ||  |||||||||||||||||||||||||  ||| |
Sbjct  5440  GAAATGTCAA-AGTTAACTAATAGTCCCTCTCTCCAAGCTCACTTACAGGCCCTCCAAGC  5498

Query  5249  AGTCCAGCACGAAGTCTGGA-GACCTCTGGCGGCAGCCTACCAAGAACAACTGGACC-GA  5306
             ||| |||  |||| ||||||  || ||||||  || || |  || ||  || ||   ||
Sbjct  5499  AGTACAACAAGAGGTCTGGAAG-CCGCTGGCCGCTGCTTATCAGGACCAGCTAGATCAG-  5556

Query  5307  CCGGTGGTACCTCACCC-TTACCGAGTCGGCGACACAGTGTGGGTCCGCCGACACCAGAC  5365
             || ||| |||| |||||  || ||| ||||  ||||||||| |||| |||||||||| ||||||
Sbjct  5557  CCAGTGATACCACACCCCTT-CCGTGTCGGTGACGCCGTGTGGGTACGCCGGCACCAGAC  5615

Query  5366  TAAGAACCTAGAACCTCGCTGGAAAGGACCTTACACAGTCCTGCTGACCACCCCCACCGC  5425
             |||||||||||||||||||||||||||||||  |||||||||||||||  |||||||||||||
Sbjct  5616  TAAGAACTTAGAACCTCGCTGGAAAGGACCCTACACCGTCCTGCTGACAACCCCCACCGC  5675

Query  5426  CCTCAAAGTAGACGGCATCGCAGCTTGGATACACGCCGCCCACGTGAAGGCTGCCGAC     5483
             ||||||||||||||||||| | || ||||||||||||||||  ||||| |||||  || |||
Sbjct  5676  TCTCAAAGTAGACGGCATCTCTGCGTGGATACACGCCGCTCACGTAAAGGCGGC-GAC     5732

.
.
.
.
.

Query  6436  GGGAACGGAAAATAGGCTGCTAAACTTAGTAGACGGAGCCTACCAAGTCCTCAACCTCAC  6495
             |||  ||||  | |  |||||||||| |||| |||||||||||||| ||||||||||||||
Sbjct  6603  GGG-ACGGGAGACAGGCTGCTAAACCTGGTAGAAGGAGCCTACCTAGCCCTCAACCTCAC  6661

Query  6496  CAGTCCTGACAAAACCAAGAGTGCTGGTTGTGTCTAGTACCGGGACCCCCTACTACGA  6555
             ||||||  ||||||||||||| ||||||| |||||||||||| ||||||||||||||||||
Sbjct  6662  CAGTCCCGACAAAACCCAAGAGTGCTGGCTGTGTCTAGTATCGGGACCCCCTACTACGA  6721

Query  6556  AGGGGTTGCCGTCCTGGGTACCTACTCCAAGCATACCTCTGCTCCAGCCAACTGCTCCGT  6615
             ||||| ||||||||||||||||  |||||||||||| || |||| |||||||||||||
Sbjct  6722  AGGGGTGGCCGTCCTAGGTACTTACTCCAACCATACCTCTGCCCCGGCTAACTGCTCCGT  6781

Query  6616  GGCCTCCCAACACAAGTGACCCTGTCGAAGTGACCGACAGGGACTCTGCATAGGAGC  6675
             | |||||||||||||||| |||||||||||||||| |||||||| |||||||||||||
Sbjct  6782  GACCTCCCAACACAAGCTGACCCTGTCCGAAGTGACCGGGCAGGGACTCTGCATAGGAGC  6841

Query  6676  AGTTCCCAAAACACATCAGGCCCTATGTAATACCACCCAGACA-A-GCAGTCGA-GGGTC  6732
             ||||||||||| ||||||||||||| |||||||||||||||| | ||  || ||| |||||
Sbjct  6842  AGTTCCCAAAACCCATCAGGCCCTGTGTAATACCACCCAGA-AGACG-AG-CGACGGGTC  6898

Query  6733  CTATTATCTAGT-TGC-CCCTACAGGTACCATGTGGGCTTGTAGTACCGGGCTTACTCCA  6790
             ||| |||  | |  |||  | ||  ||||||||| || |||||||||| || ||||||||| |||||
Sbjct  6899  CTACTATTTGGCCT-CTCCCGCCGGG-ACCATTGGGCTTGCAGCACCGGGCTCACTCCC  6956

Query  6791  TG-C-ATCTCCACCACCATACTGAACCTTA-CCACTGATTATTGTGTTCTTGTCGAACTC  6847
             || |  ||| ||  || |  |||  | |||   |||||||||||  ||||| || ||||||
Sbjct  6957  TGTCTATCT--ACTACTGTGCTTAAC-TTAACCACTGATTACTGTGTCCTGGTTGAACTC  7013
```

FIGURE 5 (cont'd)

```
Query  6848  TGGCCAAGAG-TCACCTATCATTCCCCCAGCTATGTTTACGGCCTGTTTGAGA-GATCCA  6905
             |||||||| || | ||||| || ||||| |  ||||||||  ||||  ||||| | ||   |
Sbjct  7014  TGGCCAA-AGGTAACCTACCACTCCCCTAATTATGTTTATGGCCAGTTTGAAAAGAA---A  7070

Query  6906  ACCGAC-ACAAAAGAGAACCGGTGTCGTTAACCCTGGCCCTATTATTGGGTGGACTAACC  6964
             ||  |  | |||||||| |||||||| |||||| ||||||||  | ||||| ||||| ||
Sbjct  7071  ACTAAATATAAAAGAGAGCCGGTGTCATTAACTCTGGCCCTGCTGTTGGGAGGACTTACT  7130

Query  6965  ATGGGGGAATTGCCGCTGGAATAGGAACAGGGACTACTGCTCTAATGGCCACTCAG-CA  7023
             ||||  || || || || || |||  | |||||||||||||||||| ||| |||||  || ||
Sbjct  7131  ATGGGCGGCATAGCTGCAGGAGTTGGAACAGGGACTACAGCCCTAGTGGCCAC-CAAACA  7189

Query  7024  ATTCCAGCAGCTCCAAGCCGC-AGTACAGG-ATGATCTCAGGGAGGTT-GAAAAATCAAT  7080
             |||| ||||||||||||||  ||  | | ||||  | || ||  || ||||||||| |
Sbjct  7190  ATTCGAGCAGCTCCAGGCAGCCA-TACATACA-GACCTTGGGGCC-TTAGAAAAATCAGT  7246

Query  7081  CTCTAACCTAGAAAAGTCTCTCACTTCCCTGTCTGAAGTTGTCCTACAGAATCGAAGGGG  7140
             |  |  |||||||||||||||| || ||  ||||||| || ||||||||||| || |||||
Sbjct  7247  CAGTGCCCTAGAAAAGTCTCTGACCTCGTTGTCTGAGGTGGTCCTACAGAACCGGAGGGG  7306

Query  7141  CCTAGA-CTTGTTATTTCTAAAAGAAGGAGGGCTGTGTGCTGCTCTAAAAGAAGAATGTT  7199
             |||| ||  | || |||||||||||||||||  |  ||||||||  ||||||||||||||| |
Sbjct  7307  ATTAGATCTACTG-TTCCTAAAAGAAGGAGGATTATGTGCTGCCCTAAAAGAAGAATGCT  7365

Query  7200  GCTTCTATGCGGACCACACAGGAC-TAGTGAGAGACAGCATGGCCAAAT-GAGAGAGAG  7257
             | ||  || |||||||||||||||| || | |||| ||||| |||||||| ||| | ||||| ||
Sbjct  7366  GTTTTTACGCGGACCACACTGG-CGTAGTAAGAGATAGCATGGC-AAAGCTAAGAGAAAG  7423

Query  7258  GCTTAATC-AGAGACAGAAACTGTTTGAGTCAACTCAAGCAXXXXXXXXXXXXXXXXXXX  7316
             | |||| | |||||||| |||  |||| ||| || ||| |||||  ||||||||||||||||||
Sbjct  7424  G-TTAAACCAGAGACAAAAATTGTTCGAATCAGGACAAGCGTGGTTTGAGGGACTGTTTA  7482

Query  7317  XXXATCCCCTTGGTTTACCACCTTGATATCTACCATTATGGGACCC-CTCATTGTACTC  7375
             ||||  ||||| ||||| || ||| ||||||||| |||||||||||| ||  || || |||||
Sbjct  7483  ACAGGTCCCCATGGTTCACGACCCTGATATCCACCATTATGGG-CCCTCTGATAGTACTT  7541

Query  7376  CTAATGATTTTGCTCTTCGGACCCTGCATTCTTAATCGATTAGTCCAATTGTTAAAGAC  7435
             || | || | |||||||||||||||| ||||| ||  || || ||||| ||||| ||||||
Sbjct  7542  TTATTAATCCTACTCTTCGGACCCTGTATTCTCAACCGCTTGGTCCAGTTTGTAAAAGAC  7601

Query  7436  AGGATATCAGTGGTCCAGGCTCTAGTTTTGACTCAACAATATCACCAGCTCAAGCCTATA  7495
             || || || || || || ||||| || ||| ||||| ||||| |||||||| || | |||
Sbjct  7602  AGAATTTCGGTAGTGCAGGCCCTGGTTCTGACCCAACAGTATCACCAACTCAAATCAATA  7661

Query  7496  GAGTAC-GA-GCCA-TAGA-TAA----AATAAAAGATTTTATTTAGTCTCCAGAAAAXXX  7547
             || | || | ||  | || | |||      |||||||||||||||| ||| |||||||| |||
Sbjct  7662  GA-TCCAGAAGA-AGTGGAATCACGTGAATAAAAGATTTTATTCAGTTTCCAGAAAGAGG  7719

Query  7548  XXXXAATGAAAXXXXXXXXTGTA-GGTTTGGCAAGCTAGCTTA-AGTAAXXXCATTTTG  7605
             |||||||||||||||||||| || || || ||| ||||| | |||||||||||||||||
Sbjct  7720  GGGGAATGAAAGACCCCACCA-TAAGGCTTAGCACGCTAGCT-ACAGTAACGCCATTTTG  7777

Query  7606  CAAGGCATGGAAAAATAC-ATAACTGAGAA-T-AGAGAAGTT-CA-G-A---TC-AAGGTC  7656
             |||||||||||||||| ||| | | ||||| | ||| ||||| || | |   | ||  |
Sbjct  7778  CAAGGCATGGAAAAGTACCAGAGCTGAGTTCTCA-A-AAGTTACAAGGAAGTTTAAT-TA  7834
```

FIGURE 5 (cont'd)

```
Query  7657  AGGAACA-GA-TGGA-A-CAGCTGA-ATATGGGCCAAACAGGATATCTGTGGTAAG-CAG  7710
             | ||| | |  || | | ||  |||  | | |||||||||||||||||||| || || ||
Sbjct  7835  AAGAATAAGGCTGAATAACA-CTGGGACAGGGGCCAAACAGGATATCTGTAGTCAGGCA-  7892

Query  7711  TTCCTG--CCCCGGCTCAGGGCCAAGAACAGATGG        7743
             ||||    ||||||||||||||||||||||||||
Sbjct  7893  --CCTGGGCCCCGGCTCAGGGCCAAGAACAGATGG        7925

.
.
.

Query  8069  GCGCCAGTCCTCCGATTGACTGAGTCGGCCGGGTACCCGTGTAT-CCAATAAACCCTCTT  8127
             ||||||||| |||||| ||| |||||||| ||||||||||||| | |||||||| ||||
Sbjct     1  GCGCCAGTCATCCGATAGACTGAGTCGCCCGGGTACCCGTGT-TCCCAATAAAGCCTTTT   59

Query  8128  GCAG-TTGCATCCGACTTGTGGTCTCGCTGTTCCTTGGGAGGGTCTCCTCTGAGTGATTG  8186
             || | ||||||||||  ||| ||   |||  ||||  |||| ||||| | ||||||||||
Sbjct    60  GCTGTTTGCATCCGAAGCGTGGCCTCGCTGTTCCTTGGGAGGGTCTCCTCAGAGTGATTG  119

Query  8187  ACTACCC-GTCAGCGGGGGTCTTTCATTTGGGGCTCGTCCGGGAT-CGGGAGACCCCTG  8244
             |||||||    ||| |||||||||||||||||||||||||| ||| | | ||||||||| |
Sbjct   120  ACTACCCAG-C-TCGGGGGTCTTTCATTTGGGGCTCGTCCGGGATTCGG-AGACCCCCG  176

Query  8245  CCAGGGACCACCGACCCACCACCGGGAGGTAAGCTGGCC    8284
             ||||||||||||||||||||||  ||||||||||| ||||
Sbjct   177  CCCAGGGACCACCGACCCACCGTCGGGAGGTAAGCCGGCC  216

.
.
.

Query  7757  GGGCCAAACAGGATATCTGTGGT-AAGCAGTTCCT--GCCCGGTTAGGGCCAAGAACA  7813
             |||||||||||||||||||||| || | |||  ||   ||||||| |||||||||||||
Sbjct  7864  GGGCCAAACAGGATATCTGTAGTCAGGCA---CCTGGGCCCCGGCTCAGGGCCAAGAACA  7920

Query  7814  GATGGTCCCCAGATGCGGTCCAGCCCT--CAGCAGTTTCTACAGAA--CC-ATCAGATGT  7868
             ||||| ||||   |  |  || || ||    ||||||  ||| |    || ||||| ||
Sbjct  7921  GATGGTCCTCAGATAAAG-CGAAAC-TAACAACAGTTTCTGGA-AAGTCCCACCTCA-GT  7976

Query  7869  TTCCAGGGTGCCCCAAG-GACCTG-AAATGACCCTGTGCCTTATTTGAACTAACCAATCA  7926
             |||  ||  | ||||||  ||||    ||| |||   |||||||||||| |||||||||
Sbjct  7977  TTCAAGT-T-CCCCAAAAGACCGGGAAAT-ACCCCAAGCCTTATTTAAACTAACCAATCA  8033

Query  7927  GTTCGCTTCTCGCTTCTGTTCGCGCGCTTCT-GCTCCCC-G----AGCTCAATAAAGAG  7980
             | ||||||||| ||||||| |||||||| |||  ||| | ||||||   ||| | |||| ||
Sbjct  8034  GCTCGCTTCTCGCTTCTGTACCCGCGCTTTTTGCTCCCCAGTCCTAGCCCTATAAAAAAG  8093

Query  7981  CCC-AC-AACCCCTCACTCGGGGCGCCAGTCCTCCGATTGACTGAGTCGGCCGGGTACCC  8038
             |   || || ||||||| ||||||||||||||||||| ||| ||||||| ||||||||||
Sbjct  8094  GGGTAAGAACTCCACACTCGGCGCGCCAGTCATCCGATAGACTGAGTCGCCCGGGTACCC  8153

Query  8039  GTGTATCC-AATAAACCCTCTTGCAGTT-GCA     8068
             |||| ||| |||||| ||| ||| ||| |||
Sbjct  8154  GTGT-TCCCAATAAAGCCTTTTGCTGTTTGCA     8184
```

FIGURE 5 (cont'd)

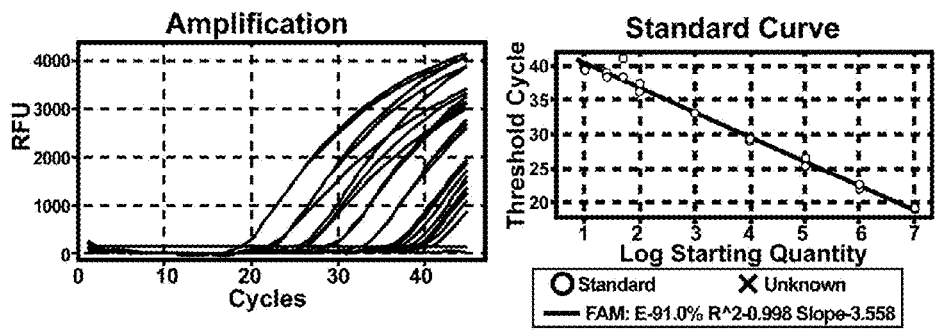
FIGURE 6
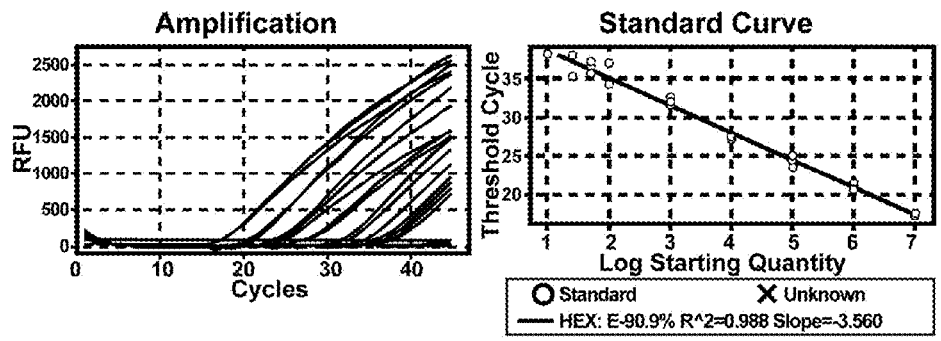
FIGURE 7
XMRV-gag
Standards
| 1-Stage qPCR_pUC57 XMRV gag Plasmid Standards ||||
|---|---|---|---|
| pUC57 XMRV gag Input Copies/Reaction | N Rows | Mean Ct | Standard Deviation |
| 1E0 | 2 | 34.88 | 0.23 |
| 1E1 | 3 | 30.37 | 0.16 |
| 1E2 | 3 | 27.07 | 0.03 |
| 1E3 | 3 | 23.27 | 0.14 |
| 1E4 | 3 | 20.39 | 0.09 |
| 1E5 | 3 | 16.63 | 0.03 |
| 1E6 | 3 | 14.43 | 0.07 |
| 1E7 | 3 | 12.51 | 0.04 |
FIGURE 8A Controls

| 1-Stage qPCR_XMRV gag Controls | | | | |
|---|---|---|---|---|
| Controls | N Rows | Mean Ct | Standard Deviation | Mean Copies/Reaction |
| 22Rv1 Pos | 3 | 14.63 | 0.03 | 870088.25 |
| h.blood Neg | 3 | ND | ND | ND |
| NTC | 3 | ND | ND | ND |

FIGURE 8B

Experimental (in human blood gDNA)

| 1-Stage qPCR_pUC57-XMRV gag Spiked Human Blood gDNA | | | | | | |
|---|---|---|---|---|---|---|
| Sample (human blood gDNA) | pUC57-XMRV gag | N Rows | Mean Ct | Standard Deviation | Copies/ reaction | %Recovery of Copies/reaction |
| Neat | 1E0 | 3 | 34.31 | 0.42 | 0.58 | 58.00 |
| | 1E1 | 3 | 31.04 | 0.15 | 6.09 | 60.90 |
| | 1E2 | 3 | 27.56 | 0.14 | 75.23 | 75.23 |
| | 1E3 | 3 | 23.83 | 0.11 | 1120.42 | 112.04 |
| | 1E4 | 3 | 21.46 | 0.1 | 6206.85 | 62.07 |
| | 1E5 | 3 | 17.48 | 0.19 | 110994.26 | 110.99 |
| | 1E6 | 3 | 15.23 | 0.08 | 564101.99 | 56.41 |
| | 1E7 | 3 | 12.91 | 0.07 | 3026602.41 | 30.27 |

FIGURE 8C

XMRV-env

Standards

| 1-Stage qPCR_pET28b XMRV env Plasmid Standards | | | |
|---|---|---|---|
| pET28b XMRV env Input Copies/Reaction | N Rows | Mean Ct | Standard Deviation |
| 1E0 | 3 | 33.68 | 0.98 |
| 1E1 | 3 | 29.56 | 0.13 |
| 1E2 | 3 | 26.5 | 0.08 |
| 1E3 | 3 | 23.31 | 0.09 |
| 1E4 | 3 | 20.1 | 0.12 |
| 1E5 | 3 | 16.42 | 0.06 |
| 1E6 | 3 | 14.41 | 0.05 |
| 1E7 | 3 | 12.07 | 0.02 |

FIGURE 9A

Controls

| 1-Stage qPCR_XMRV env Controls | | | | |
|---|---|---|---|---|
| Controls | N Rows | Mean Ct | Standard Deviation | Mean Copies/Reaction |
| 22Rv1 Pos | 3 | 14.98 | 0.06 | 582422.25 |
| h.blood Neg | 3 | ND | ND | ND |
| NTC | 3 | ND | ND | ND |

FIGURE 9B

Experimental (in human blood gDNA)

| 1-Stage qPCR_ pET28b-XMRV env Spiked Human Blood gDNA | | | | | | |
|---|---|---|---|---|---|---|
| Sample (human blood gDNA) | pET28b XMRV env | N Rows | Mean Ct | Standard Deviation | Copies/ reaction | %Recovery of Copies/reaction |
| Neat | 1E0 | 3 | 33.44 | 0.51 | 0.68 | 68.00 |
| | 1E1 | 3 | 30.12 | 0.07 | 7.62 | 76.20 |
| | 1E2 | 3 | 26.97 | 0.07 | 79.21 | 79.21 |
| | 1E3 | 3 | 23.82 | 0.13 | 825.75 | 82.58 |
| | 1E4 | 3 | 20.51 | 0.08 | 9641.13 | 96.41 |
| | 1E5 | 3 | 16.89 | 0.1 | 141843.44 | 141.84 |
| | 1E6 | 3 | 14.85 | 0.04 | 643411.76 | 64.34 |
| | 1E7 | 3 | 12.23 | 0.07 | 4494825.98 | 44.95 |

FIGURE 9C

XMRV pol2 Standards

| 1-Stage qPCR_pAZ3-emd pol2 Plasmid Standards | | | |
|---|---|---|---|
| pAZ3-emd pol2 Input Copies/Reaction | N Rows | Mean Ct | Standard Deviation |
| 1E0 | 3 | 35.15 | 1 of 3 Detected |
| 1E1 | 3 | 33.15 | 1.15 |
| 1E2 | 3 | 28.99 | 0.1 |
| 1E3 | 3 | 26.36 | 0.11 |
| 1E4 | 3 | 23.36 | 0.08 |
| 1E5 | 3 | 20.73 | 0.14 |
| 1E6 | 3 | 17.57 | 0.1 |

FIGURE 10A

Controls

| 1-Stage qPCR_XMRV pol2 Controls | | | | |
|---|---|---|---|---|
| Controls | N Rows | Mean Ct | Standard Deviation | Mean Copies/Reaction |
| 22Rv1 Pos | 3 | 14.62 | 0.08 | 9341829.77 |
| h.blood Neg | 3 | ND | ND | ND |

FIGURE 10B

Experimental (in human blood gDNA)

| 1-Stage qPCR_pAZ3-emd pol2 Spiked Human Blood gDNA | | | | | | |
|---|---|---|---|---|---|---|
| Sample (human blood gDNA) | pAZ3-emd pol2 | N Rows | Mean Ct | Standard Deviation | Copies/ reaction | %Recovery of Copies/reaction |
| Neat | 1E0 | 3 | 34.46 | 0.1 | 2.21 | 221.00 |
| | 1E1 | 3 | 34.13 | 0.91 | 3.3 | 33.00 |
| | 1E2 | 3 | 29.74 | 0.24 | 84.01 | 84.01 |
| | 1E3 | 3 | 26.69 | 0.06 | 866.55 | 86.66 |
| | 1E4 | 3 | 23.97 | 0.05 | 7011.98 | 70.12 |
| | 1E5 | 3 | 20.98 | 0.07 | 70064.46 | 70.06 |
| | 1E6 | 3 | 17.67 | 0.02 | 885681.45 | 88.57 |

FIGURE 10C

0-Stage vs. 1-Stage qPCR Protocols
XMRV-Gag
pUC57 XMRV gag_Standards

| pUC57 XMRV gag_Standards ||||  |
|---|---|---|---|---|
| pUC57 XMRV gag | Protocol Stage | N Rows | Mean Ct | Standard Deviation |
| 1E0 | 0-stage | 3 | 37.03 | 0.02 |
|  | 1-stage | 3 | 35.15 | 1.42 |
| 1E1 | 0-stage | 3 | 33.76 | 0.16 |
|  | 1-stage | 3 | 30.83 | 0.1 |
| 1E2 | 0-stage | 3 | 30.41 | 0.06 |
|  | 1-stage | 3 | 27.45 | 0.14 |
| 1E3 | 0-stage | 3 | 26.32 | 0.1 |
|  | 1-stage | 3 | 23.32 | 0.08 |
| 1E4 | 0-stage | 3 | 23.94 | 0.07 |
|  | 1-stage | 3 | 20.87 | 0.09 |
| 1E5 | 0-stage | 3 | 20.13 | 0.02 |
|  | 1-stage | 3 | 17.13 | 0.06 |
| 1E6 | 0-stage | 3 | 17.17 | 0.03 |
|  | 1-stage | 3 | 14.47 | 0.09 |
| 1E7 | 0-stage | 3 | 15.66 | 0.05 |
|  | 1-stage | 3 | 12.71 | 0.02 |

FIGURE 11A pUC57 XMRV gag spike-ins into 001 Human Blood gDNA

| pUC57 XMRV gag spike-ins into 001 Human Blood gDNA | | | | | |
|---|---|---|---|---|---|
| pUC57 XMRV gag/001 gDNA | Protocol Stage | N Rows | Mean Ct | Standard Deviation | Detected Copies/reaction |
| 1E0 | 0-stage | 3 | 36.64 | 0.94 | 1.07 |
| 1E0 | 1-stage | 3 | 34.02 | 0.52 | 1.1 |
| 1E1 | 0-stage | 3 | 32.96 | 0.18 | 13.97 |
| 1E1 | 1-stage | 3 | 29.53 | 0.69 | 27.73 |
| 1E2 | 0-stage | 3 | 30.23 | 0.08 | 101.91 |
| 1E2 | 1-stage | 3 | 27.26 | 0.13 | 127.75 |
| 1E3 | 0-stage | 3 | 26.5 | 0.08 | 1553.29 |
| 1E3 | 1-stage | 3 | 23.52 | 0.08 | 1826.01 |
| 001 Blood gDNA_Naive | 0-stage | 3 | ND | ND | ND |
| 001 Blood gDNA_Naive | 1-stage | 3 | ND | ND | ND |

FIGURE 11B

XMRV-Env
pET28b XMRV env_Standards

| pET28b XMRV env_Standards ||||| 
|---|---|---|---|---|
| pET28b XMRV env | Protocol Stage | N Rows | Mean Ct | Standard Deviation |
| 1E0 | 0-stage | 3 | 36.08 | 0.17 |
|  | 1-stage | 3 | 32.9 | 0.63 |
| 1E1 | 0-stage | 3 | 32.34 | 0.21 |
|  | 1-stage | 3 | 29.8 | 0.36 |
| 1E2 | 0-stage | 3 | 28.82 | 0.16 |
|  | 1-stage | 3 | 26.59 | 0.11 |
| 1E3 | 0-stage | 3 | 25.7 | 0.05 |
|  | 1-stage | 3 | 23.53 | 0.07 |
| 1E4 | 0-stage | 3 | 22.4 | 0.05 |
|  | 1-stage | 3 | 20.22 | 0.04 |
| 1E5 | 0-stage | 3 | 18.66 | 0.09 |
|  | 1-stage | 3 | 16.5 | 0.07 |
| 1E6 | 0-stage | 3 | 16.56 | 0.15 |
|  | 1-stage | 3 | 14.14 | 0.07 |
| 1E7 | 0-stage | 3 | 14.35 | 0.1 |
|  | 1-stage | 3 | 12.11 | 0.05 |

FIGURE 12A pET28b XMRV env spike-ins into 001 Human Blood gDNA

| pET28b XMRV env spike-ins into 001 Human Blood gDNA ||||||
|---|---|---|---|---|---|
| pET28b XMRV env /CA gDNA | Protocol Stage | N Rows | Mean Ct | Standard Deviation | Detected Copies/reaction |
| 1E0 | 0-stage | 3 | 36.42 | 0.74 | 0.51 |
|  | 1-stage | 3 | 34.71 | 0.47 | 0.23 |
| 1E1 | 0-stage | 3 | 33.49 | 0.79 | 4.53 |
|  | 1-stage | 3 | 30.43 | 0.27 | 5.59 |
| 1E2 | 0-stage | 3 | 29.88 | 0.1 | 56.34 |
|  | 1-stage | 3 | 27.08 | 0.04 | 68.29 |
| 1E3 | 0-stage | 3 | 25.86 | 0.3 | 1078.16 |
|  | 1-stage | 3 | 23.16 | 0.08 | 1301.04 |
| 001 Blood gDNA_Naive | 0-stage | 3 | ND | ND | ND |
|  | 1-stage | 3 | ND | ND | ND |

FIGURE 12B

XMRV-Pol2 pAZ3-emd pol2_Standards

| pAZ3-emd pol2_Standards | | | | |
|---|---|---|---|---|
| pAZ3-emd pol2 | Protocol Stage | N Rows | Mean Ct | Standard Deviation |
| 1E0 | 0-stage | 3 | ND | ND |
| | 1-stage | 3 | 36.06 | 1 of 3 Detected |
| 1E1 | 0-stage | 3 | 36.01 | 0.3 |
| | 1-stage | 3 | 33.09 | 0.15 |
| 1E2 | 0-stage | 3 | 32.75 | 0.16 |
| | 1-stage | 3 | 29.99 | 0.2 |
| 1E3 | 0-stage | 3 | 29.79 | 0.13 |
| | 1-stage | 3 | 26.56 | 0.04 |
| 1E4 | 0-stage | 3 | 26.7 | 0.09 |
| | 1-stage | 3 | 23.47 | 0.05 |
| 1E5 | 0-stage | 3 | 23.93 | 0.06 |
| | 1-stage | 3 | 20.57 | 0.09 |
| 1E6 | 0-stage | 3 | 20.99 | 0.14 |
| | 1-stage | 3 | 17.75 | 0.16 |

FIGURE 13A pAZ3-emd pol2 spike-ins into 001 Human Blood gDNA

| pAZ3-emd pol2 spike-ins into 001 Human Blood gDNA | | | | | |
|---|---|---|---|---|---|
| pAZ3-emd pol2 /001 gDNA | Protocol Stage | N Rows | Mean Ct | Standard Deviation | Detected Copies/reaction |
| 1E0 | 0-stage | 3 | ND | ND | ND |
| | 1-stage | 3 | 35.05 | 1 of 3 Detected | 2.09 |
| 1E1 | 0-stage | 3 | 36.74 | 0.73 | 5.44 |
| | 1-stage | 3 | 33.63 | 1.22 | 7.38 |
| 1E2 | 0-stage | 3 | 32.65 | 0.01 | 114.29 |
| | 1-stage | 3 | 29.52 | 0.18 | 130.53 |
| 1E3 | 0-stage | 3 | 30.06 | 0.21 | 847.39 |
| | 1-stage | 3 | 27.18 | 0.08 | 746.81 |
| 001 Blood gDNA_Naive | 0-stage | 3 | 37.49 | 1 of 3 Detected | 2.72 |
| | 1-stage | 3 | ND | ND | ND |

FIGURE 13B

|  | Spike-In Copy # | MLV ||||| Env2 |||||
|---|---|---|---|---|---|---|---|---|---|---|---|
| Sample | | Mean Ct | Std Dev | N | % CV | Copy # | Mean Ct | Std Dev | N | % CV | Copy # |
| 100 ng Frozen Fresh + | 7980 | 26.05 | 0.065 | 3 | 0.25% | 2660 | 25.05 | 0.119 | 3 | 0.47% | 3568 |
| 100 ng FFPE + | 4856 | 27.12 | 0.434 | 3 | 1.60% | 1301 | 24.28 | 0.408 | 3 | 1.68% | 6229 |
| 100 ng FFPE - | ------ | 27.48 | 1.060 | 3 | 3.86% | 1141 | 25.39 | 0.676 | 3 | 2.66% | 3029 |

FIGURE 14

| Input Copies/reaction | Standards | N Rows | Mean Ct | Standard Deviation | %CV |
|---|---|---|---|---|---|
| 1.00E+00 | XMRV env | 3 | . | . | . |
| | XMRV gag | 2 | . | . | . |
| | XMRV pol2 | 3 | . | . | . |
| 1.00E+01 | XMRV env | 3 | 32.92 | 0.77 | 2.35 |
| | XMRV gag | 2 | 30.83 | 0.28 | 0.89 |
| | XMRV pol2 | 3 | 33.63 | 0.69 | 2.06 |
| 1.00E+02 | XMRV env | 3 | 29.43 | 0.19 | 0.66 |
| | XMRV gag | 2 | 30.83 | 0.28 | 0.89 |
| | XMRV pol2 | 3 | 30.04 | 0.05 | 0.17 |
| 1.00E+03 | XMRV env | 3 | 26.58 | 0.11 | 0.4 |
| | XMRV gag | 2 | 27.6 | 0.33 | 1.18 |
| | XMRV pol2 | 3 | 26.61 | 0.2 | 0.75 |
| 1.00E+04 | XMRV env | 3 | 23.4 | 0.06 | 0.24 |
| | XMRV gag | 2 | 24.3 | 0.09 | 0.38 |
| | XMRV pol2 | 3 | 23.41 | 0.07 | 0.31 |
| 1.00E+05 | XMRV env | 3 | 20.56 | 0.04 | 0.2 |
| | XMRV gag | 2 | 21.45 | 0.13 | 0.59 |
| | XMRV pol2 | 3 | 20.86 | 0.24 | 1.13 |
| 22Rv1 gDNA_5 ng_Pos | XMRV env | 3 | 19.28 | 0.09 | 0.47 |
| | XMRV gag | 3 | 20.39 | 0.1 | 0.47 |
| | XMRV pol2 | 3 | 19.71 | 0.18 | 0.91 |
| qPCR NTC | XMRV env | 3 | . | . | . |
| | XMRV gag | 3 | . | . | . |
| | XMRV pol2 | 3 | . | . | . |
| RT NTC | XMRV env | 3 | . | . | . |
| | XMRV gag | 2 | . | . | . |
| | XMRV pol2 | 3 | . | . | . |

FIGURE 15

RETROVIRUS DETECTION

CROSS REFERENCE TO RELATED APPLICATIONS

This application is a U.S. National Stage Application filed under 35 U.S.C §371 and claims priority to International Application No. PCT/US 11/44296, filed Jul. 16, 2011, which claims priority under 35 U.S.C. 119 to U.S. Provisional Application Ser. No. 61/365,297, filed Jul. 16, 2010; 61/386,941, filed Sep. 27, 2010; and 61/391,360, filed Oct. 8, 2010, the disclosures of which are incorporated herein by reference.

TECHNICAL FIELD

The invention relates to methods and compositions useful for the detection of retroviruses in a subject or sample.

BACKGROUND

Xenotropic murine leukemia virus-related virus (XMRV) is a recently discovered human gammaretrovirus that resembles a xenotropic MLV, but that is distinguishable from xenotropic MLV in the sequence in its envelope (Urisman et al., PLOS pathogens 2(3):e25, 2006; and Dong et al. PNAS 104:1655, 2007). All isolates so far examined are highly homologous to each other (>98% sequence identity) and allow the distinction from xenotropic MLV. The reason for this sequence conservation is not currently understood. The original infectious clone is called XMRV VP62 (GenBank accession no. EF185282).

XMRV was originally described in association with prostate cancer and further connections have been suggested (R. Schlaberg et al. PNAS 2009, doi_10.1073_pnas. 0906922106), with 6-23% of prostate cancer patients testing positive. In addition, V. C. Lombardi et al. (Science 2009 doi10.1126/science. 1179052) showed a possible association with chronic fatigue syndrome, with 67% of patients testing positive, compared to 3.7% of normals. Overall estimates of the prevalence in the general population from investigators in the USA range from 2-4%. However several recent studies in Europe have failed to detect XMRV in similar frequencies or similar associations (Fischer et al. Journal of Clinical Virology 43: 277-283 2008; Hohn et al. Retrovirology 6:92 2009; FJM van Kuppeveld et al., BMJ 340: c1018, 2010). Fischer et al. found 1 of 105 prostate cancer patients and 1 of 70 control subjects to be XMRV positive in a German study. Hohn et al. screened 589 prostate cancer patients in Germany without detecting a single positive. Van Kuppeveld et al. also failed to detect any DNA or RNA positives in 32 chronic fatigue patients or in 42 matched controls in Holland. Recently another paper from Fischer et al. (Emerg Infect Dis. 2010) showed about 10% positivity in RNA derived from sputum of 162 immunosuppressed patients and 2-3% positivity in sputum RNA from 168 normal patients in a German study. The assays did not appear to be different and no explanation was offered for the discrepancies.

The inconsistency of results calls into question the reliability of the current testing methods, in particular in DNA amplification. Following the lead of Lombardi et al. all investigators so far have used nested PCR using XMRV sequence based primers, followed by running the sample on a gel and looking for a visible band. This method is known to be variable in sensitivity and depend on the quality of nucleic acid samples. Detection of XMRV RNA has also been described mainly using the method of Dong et al. PNAS 2007, based on that of Urisman et al. 2006. In this assay RNA is prepared from tissue and/or blood, reverse transcribed to cDNA and the cDNA examined by QPCR with XMRV specific primers. As noted this led to inconsistent results (Enserink et al., Science 329:18-19, 2010). Claims of various sensitivities have been made for such tests, but it is not possible to verify any of these and the assays appear to be incompletely characterized.

A PCR based diagnostic screening assay for XMRV in human blood has been recently developed (www[.]vipdx-.com), using nested PCR and gel detection of the amplification product (Lombardi et al.), with an estimated sensitivity for the nested DNA PCR around 600 proviral copies/ test. In addition the report of Lombardi et al. do not show complete concordance of gag and env detection, with positives in gag and negatives for env observed in some subjects. This was attributed to variability in the assay. In all of the assays developed so far great care has been taken to use primers that will differentiate MLV from XMRV, so that only XMRV is detected. Therefore there is a great need for a reliable and validated assay for XMRV DNA and RNA in accessible samples from volunteers or patients in order to determine the real frequencies of positivity and whether there is linkage to disease. In addition a reliable blood screening assay is not available. Recent data suggest that detection of XMRV in many cases is caused by artifacts (Paprotka T., Science, 333, 97-101, 2011) or contamination with mouse DNA (Robinson M J. et al., Retrovirology, 7:108 doi: 10.1186/1742-4690-7-108, 2010).

Furthermore, gene therapy vectors based upon MLV are being used including replication competent MLV-based vectors. For example, a replicating retrovirus based on amphotropic MLV and carrying an extra cytosine deaminase gene as a therapeutic agent for cancer including primary brain cancer leading to glioblastoma multiforme (GBM) (Tai et al., Mol. Ther., 12:842-851 2005; http:(//)oba.od.nih.gov/oba/RAC/meetings/Jun2009/976_Aghi.pdf; WO2010036986) having been used. An exemplary vector is being developed by Tocagen Inc. (San Diego, Calif.) and is referred to as Toca 511 (clinical trials.gov trial# NCT01156584). Subsequent to Toca 511 administration, patients are dosed with 5-fluorocytosine that is converted in situ to 5-fluorouracil, a potent anticancer compound. As the virus is generally only able to replicate in the tumor, this results in a very specific anti-cancer effect. In order to determine whether there is replication outside the tumor, for safety and/or for correlation with efficacy assays for detection of proviral DNA in the blood and MLV RNA in the plasma are needed. FDA currently requires follow-up on patients undergoing such investigational therapies with an integrating viral vector for 15 years post-treatment (Guidance for Industry—Supplemental Guidance on Testing for Replication Competent Retrovirus in Retroviral Vector Based Gene Therapy Products and During Follow-up of Patients in Clinical Trials Using Retroviral Vectors: FDA Center for Biologics Evaluation and Research November 2006; http://www.fda.gov/BiologicsBloodVaccines/GuidanceComplianceRegulatoryInformation/Guidances/CellularandGeneTherapy/ucm072961.htm). Assays are needed to accomplish this and a generally accepted marker for risk of disease and disease progression in viral diseases in general and retroviral diseases in particular is the levels over time of virus in the blood or in blood cells (Gurunathan S, Habib R E, et al. Vaccine. 2009; 27:1997-2015; Low A., Okeoma C M. et al. Virology 2009; 385: 455-463). On the other hand, replication of the virus in the tumor may leak into the periphery and blood stream and so assays that monitor the appearance and levels of viral sequence in the blood as DNA or RNA can be used to determine whether there is an effective treatment and whether there is a need to modify the treatment protocol, for example to readminister the viral vector or to use adjuvants (such as steroids) that will facilitate the viral replication in the tumor.

SUMMARY

The disclosure provides oligonucleotide primers and probes for amplification and detection of MLV-related polynucleotides in a sample, tissue or subject. In one embodiment, the disclosure provides primers that can amplify multiple strains of MLV and XMRV and probe that can detect either or both of MLV or XMRV. In another embodiment, the disclosure provides primers and probes for monitoring subject undergoing treatment with a replication competent retrovirus expressing a heterologous gene such as cytosine deaminase. In this embodiment, the "companion" diagnostic is used to insure efficacy, expression, spread and long term infection of a vector used in such treatment.

The disclosure thus provides an isolated oligonucleotide consisting of a sequence selected from the group consisting of: SEQ ID NO:1, 2, 3, 4, 5, 6, 7, 8, 9, 10, 11, 12, 13, 14, 15, 16, 17, 18, 19, 20, or 21 or any sequence set forth in Table 1 and oligonucleotides that are at least 95% identical to any of the foregoing and can hybridize to an MLV-related polynucleotide. In some embodiment, the primers and probes may differ from the foregoing or listed sequences in table 1 by 1-10 nucleotides at either the 5' and/or 3' end. In another embodiment, a primer pair consisting of SEQ ID NO: 1 and 2 and sequence that are at least 95% identical to SEQ ID NO: 1 and 2 and hybridize to an MLV-related polynucleotide. In yet another embodiment, a primer pair consisting of SEQ ID NO:4 and 5 and sequence that are at least 95% identical to SEQ ID NO:4 and 5 and hybridize to an MLV-related polynucleotide. In yet another embodiment, a primer pair consisting of SEQ ID NO:7 and 8 and sequence that are at least 95% identical to SEQ ID NO:7 and 8 and hybridize to an MLV-related polynucleotide. In yet another embodiment, a primer pair consisting of SEQ ID NO: 10 and 11 and sequence that are at least 95% identical to SEQ ID NO: 10 and 11 and hybridize to an MLV-related polynucleotide. In yet another embodiment, a primer pair consisting of SEQ ID NO: 13 and 14 and sequence that are at least 95% identical to SEQ ID NO: 13 and 14 and hybridize to an MLV-related polynucleotide. In yet another embodiment, a primer pair consisting of SEQ ID NO: 16 and 17 and sequence that are at least 95% identical to SEQ ID NO:16 and 17 and hybridize to an MLV-related polynucleotide. In yet another embodiment, a primer pair consisting of SEQ ID NO:19 and 20 and sequence that are at least 95% identical to SEQ ID NO:19 and 20 and hybridize to an MLV-related polynucleotide. In yet another embodiment, the oligonucleotide comprises a primer chose from regions of homology between XMRV and MLV.

The disclosure also provides a method of determining viral content in a subject about to undergo or undergoing a retroviral gene delivery therapy using an MLV-related virus, comprising: obtaining a sample from the subject; contacting the sample with one or more primer pairs as set forth above under conditions suitable for nucleic acid amplification to obtain amplified products; contacting the sample with a one or more probes that hydridizes to the amplified product; detecting a hybridized product; indicating that the subject has viral content comprising an MLV-related virus. In one embodiment, the MLV-related virus is a recombinant retroviral vector used in gene delivery. In another embodiment, the MLV-related virus is an XMRV virus. In yet another embodiment, the method is carried out prior to delivery of a MLV-related retroviral vector for gene delivery. In yet another embodiment, the method is carried out following delivery of a MLV-related retroviral vector for gene delivery. In another embodiment, the MLV-related virus comprises a 5' LTR, gag, pol, env genes, a regulatory domain 3' of the env gene linked to a heterologous polynucleotide to be delivered and a 3' LTR and a promoter for expression in mammalian cells in the 5'LTR. In another embodiment, the regulatory domain is an internal ribosome entry site (IRES). In yet another embodiment, the heterologous polynucleotide encodes a polypeptide having cytosine deaminase activity. In embodiments and described above, the method monitors the spread of the MLV-related retroviral vector. In another embodiment, the method is carried out routinely over the course years.

The disclosure also provides a method for detecting the presence of a viral agent in a sample comprising: measuring the amount of a polynucleotide in a sample using a quantitative polymerase chain reaction or other amplification process comprising oligonucleotide primer/probe combinations selected from the group consisting of: (i) SEQ ID NO: 1, 2 and 3; (ii) SEQ ID NO: 4, 5 and 6; (iii) SEQ ID NO: 7, 8 and 9; (iv) SEQ ID NO: 10, 11 and 12; and (v) primer pairs according to claim 9 and corresponding probes that have at least 95% identity to both XMRV and MLV. In one embodiment, the polynucleotide is DNA or RNA.

In various embodiments above, the quantitating and amplification are performed by quantitative polymerase chain reaction, e.g., RT-qPCR. In any of the foregoing methods the measuring detects a single copy of a viral agent related nucleic acid. In any of the foregoing embodiments, the sample can be a mammalian tissue (e.g., blood). In any of the foregoing embodiments a viral agent to be detected can be a gene therapy vector. In one embodiment, the gene therapy vector is a replication-competent vector. In another embodiment, the method is performed prior to a therapeutic regimen comprising a gene therapy vector treatment. In yet another embodiment, the method is performed subsequent to a therapeutic regimen comprising gene therapy vector on a subject. The method can be performed to monitor the dosage of a therapeutic regimen comprising a gene therapy vector in a subject. In yet another embodiment, the gene therapy vector comprises a replication competent MLV vector. In yet another embodiment, the method is performed prior to a therapeutic regimen comprising a gene therapy vector. In one embodiment, the method is performed subsequent to a therapeutic regimen comprising a gene therapy vector. In yet another embodiment, the method is performed to monitor the dosage of a therapeutic regimen comprising a gene therapy vector.

The disclosure also provides kits for carrying out any of the foregoing methods and comprising any of the oligonucleotides compositions of the disclosure (e.g., SEQ ID NO:1-21, Table 1).

The disclosure also provides a method for detecting <100 copies of MLV related DNA in a sample extracted from fixed histopathological sections. The disclosure also provides a method for detecting <100 copies of MLV related RNA in a sample extracted from fixed histopathological sections.

The disclosure also provides a method that detects both MLV and XMRV and variants thereof. In other embodiment, the method detects only MLV related virus and does not detect XMRV. In certain embodiment, the method detects XMRV gag and MLV gag. In yet other embodiment, the method detects XMRV pol and MLV pol. The disclosure provides methods that detects XMRV Env and MLV Env. The disclosure also provides methods for detecting either XMRV or MLV related virus in plasma or serum from a mammalian host.

The disclosure provides a method of selectively detecting MLV related viruses in humans and which does not detect XMRV comprising primers selected from the group consisting of: SEQ ID NO: 10 and 11; SEQ ID NO: 13 and 14; SEQ ID NO: 16 and 17; SEQ ID NO: 19 and 20; sequences at least 95% identical to the foregoing; and combination thereof, using the methods described herein.

The disclosure also provides a method of determining whether a human subject is at risk of having prostate cancer or chronic fatigue syndrome comprising utilizing primer pairs and probes as set forth in SEQ ID NOs: 1, 2, 3, 4, 5, 6, 7, 8, 9, 10, 11, 12, 13 or 14 or primer/probes as set forth in Table 1, to amplify polynucleotides in a sample from the subject, wherein the presence of an amplified product is indicative of a risk of prostate cancer or chronic fatigue syndrome.

The disclosure also provides a method of screening a blood supply or tissue bank for infection by an MLV, MLV-variant or XMRV comprising performing an amplification reaction on the blood supply or tissue bank utilizing primers as set forth in SEQ ID NO:4, 5, 7, 8, 10, 11, 13, 14, or any of the primers in Table 1, and detecting an amplified product.

The disclosure is directed to the detection of xenotropic murine leukemia virus related virus (XMRV) or other retroviruses related to murine leukemia viruses that can be present in human tissue blood or serum. In particular, the disclosure relates to sensitive reliable quantitative PCR assays for the detection of XMRV provirus in DNA from blood of human and animal subjects and for the sensitive and reliable detection of XMRV RNA (potentially from viral particles) from plasma or serum of human and animal subject by reverse transcription (RT) and polymerase chain reaction. In one embodiment, the quantitative assay is a TaqMan® assay using the primers and probes constructed based on the genome of the XMRV virus. In contrast to other techniques using XMRV specific primer/probe sets and avoiding primer/probe sets with homology to MLV, the disclosure constructed PCR based assays that detect MLV related viruses that may or may not be XMRV in human samples, by using MLV specific qPCR primers and probes, that also detect XMRV. Such assays are useful in combination with assays for MLV sequences that are not homologous to XMRV to determine if recombination has occurred in patients treated with replication competent retroviruses, who may also be positive for XMRV. The disclosure further relates to a diagnostic kit that comprises nucleic acid molecules for the detection of the XMRV and MLV related viruses. In addition, for detection of MLV vectors when monitoring of patients treated with MLV related vectors, diagnostic kits that detect the transgene carried by the MLV vector are also disclosed.

The details of one or more embodiments of the disclosure are set forth in the accompanying drawings and the description below. Other features, objects, and advantages will be apparent from the description and drawings, and from the claims.

BRIEF DESCRIPTION OF DRAWINGS

FIG. 5 shows a BLAST nucleic acid sequence comparison of the sequence of XMRV (VP62, NCBI ref. NC_007815.1, Sbjct; SEQ ID NO:27) and MoMLV (NCBI ref. NC_001501.1, Query; SEQ ID NO:26), showing sequences of 20 or more nucleotides that are exactly homologous (underlined/highlighted).

FIG. 6 shows XMRV gag standard in pUC57-XMRV gag plasmid DNA amplification curves from 1E0 to 1E7.

FIG. 7 shows XMRV env standard in pET28b-XMRV env plasmid DNA amplification curves from 1E0 to 1E7.

FIG. 8A-C shows a) 1-Stage qPCR Protocol: pUC57-XMRV gag plasmid standard targeted with XMRV gag primer/probe set. pUC57-XMRV gag plasmid DNA in TE was targeted with XMRV gag primers and a 1-stage qPCR protocol was performed. The mean Ct and standard deviation was calculated; b) shows 1-Stage qPCR Protocol: Controls targeted with XMRV gag primer/probe set. 22Rv1 gDNA positive control, naive human blood gDNA negative control and NTC were targeted with the XMRV gag primer/probe set and a 1-stage qPCR protocol was performed. The mean Ct, standard deviation and copies/reaction were calculated. 'ND' means 'non-detected'; c) shows 1-Stage qPCR Protocol: Spiked human blood gDNA targeted with XMRV gag primer/probe set. Neat human blood gDNA was spiked with 8 log concentrations of pUC57-XMRV gag plasmid DNA (1E0 to 1E8 copies/reaction). The samples were targeted with the XMRV gag primer/probe set and a 1-stage qPCR protocol was performed. The mean Ct, standard deviation, copies/reaction and % recovery of the input copies/reaction were determined (the % recovery was determined by using the following equation: detected copies/reaction divided by the input copies/reaction times 100).

FIG. 9A-C shows a) 1-Stage qPCR Protocol: pET28b-XMRV env plasmid standard targeted with XMRV env primer/probe set. pET28b-XMRV env plasmid DNA in TE was targeted with XMRV env primers and a 1-stage qPCR protocol was performed. The mean Ct and standard deviation was calculated; b) shows 1-Stage qPCR Protocol: Controls targeted with XMRV env primer/probe set. 22Rv1 gDNA positive control, naive human blood gDNA negative control and NTC were targeted with the XMRV env primer/probe set and a 1-stage qPCR protocol was performed. The mean Ct, standard deviation and copies/reaction were calculated. 'ND' means 'non-detected'; c) shows 1-Stage qPCR Protocol: Spiked human blood gDNA targeted with XMRV env primer/probe set. Neat human blood gDNA was spiked with 8 log concentrations of pET28b-XMRV env plasmid DNA (1E0 to 1E8 copies/reaction). The samples were targeted with the XMRV env primer/probe set and a 1-stage qPCR protocol was performed. The mean Ct, standard deviation, copies/reaction and % recovery of the input copies/reaction were determined (the % recovery was determined by using the following equation: detected copies/reaction divided by the input copies/reaction times 100).

FIG. 10A-C shows a) 1-Stage qPCR Protocol: pAZ3-emd pol2 plasmid standard targeted with XMRV pol2 primer/probe set. pAZ3-emd pol2 plasmid DNA in TE was targeted with XMRV pol2 primers and a 1-stage qPCR protocol was performed. The mean Ct and standard deviation was calculated; b) shows 1-Stage qPCR Protocol: Controls targeted with XMRV pol2 primer/probe set. 22Rv1 gDNA positive control, and naive human blood gDNA negative control were targeted with the XMRV pol2 primer/probe set and a 1-stage qPCR protocol was performed. The mean Ct, standard deviation and copies/reaction were calculated. 'ND' means 'non-detected'; c) shows 1-Stage qPCR Protocol: Spiked human blood gDNA targeted with XMRV pol2 primer/probe set. Neat human blood gDNA was spiked with 8 log concentrations of pAZ3-emd pol2 plasmid DNA (1E0 to 1E8 copies/reaction). The samples were targeted with the XMRV pol2 primer/probe set and a 1-stage qPCR protocol was performed. The mean Ct, standard deviation, copies/reaction and % recovery of the input copies/reaction were determined (the % recovery was determined by using the following equation: detected copies/reaction divided by the input copies/reaction times 100).

FIG. 11A-B shows a) 0-Stage vs. 1-Stage qPCR Protocols: pUC57 XMRV gag Standards. A 0-stage and a 1-stage qPCR protocol were performed targeting the pUC57 XMRV gag plasmid using XMRV gag primers. 'pUC57 XMRV gag' means the number of pUC57 XMRV gag copies spiked into a single qPCR reaction; b) shows 0-Stage vs. 1-Stage qPCR Protocols: pUC57 XMRV gag spike-ins into CA Human Blood gDNA. A 0-stage and a 1-stage qPCR protocol were performed targeting pUC57 XMRV gag spike-ins into CA human blood gDNA and using XMRV gag primers. 'pUC57 XMRV gag/001 gDNA' means the number of pUC57 XMRV gag copies spiked into donor 001 gDNA in a single qPCR reaction; '001' means 'donor #001'; 'ND' means 'non-detected'.

FIG. 12A-B shows a) 0-Stage vs. 1-Stage qPCR Protocols: pET28b XMRV env Standards. A 0-stage and a 1-stage qPCR protocol were performed targeting the pET28b XMRV env plasmid using XMRV env primers. 'pET28b XMRV env' means the number of pET28b XMRV env copies spiked into a single qPCR reaction; b) shows 0-Stage vs. 1-Stage qPCR Protocols: pET28b XMRV env spike-ins into 001 Human Blood gDNA. A 0-stage and a 1-stage qPCR protocol were performed targeting pET28b XMRV env spike-ins into 001 human blood gDNA and using XMRV env primers. 'pET28b XMRV env/001 gDNA' means the number of pET28b XMRV env copies spiked into donor 001 gDNA in a single qPCR reaction; '001' means 'donor #001'; 'ND' means 'non-detected'.

FIG. 13A-B shows a) 0-Stage vs. 1-Stage qPCR Protocols: pAZ3-emd pol2 standards. A 0-stage and a 1-stage qPCR protocol were performed targeting the pAZ3-emd pol2 plasmid using XMRV pol2 primers. 'pAZ3-emd pol2' means the number pAZ3-emd pol2 copies spiked into a single qPCR reaction; 'ND' means 'non-detected'; b) Shows 0-Stage vs. 1-Stage qPCR Protocols: pAZ3-emd pol2 spike-ins into 001 Human Blood gDNA. A 0-stage and a 1-stage qPCR protocol were performed targeting pAZ3-emd pol2 spike-ins into 001 human blood gDNA and using XMRV pol2 primers. 'pAZ3-emd pol2/001 gDNA' means the number of pAZ3-emd pol2 copies spiked into donor 001 gDNA in a single qPCR reaction; '001' means 'donor #001'; 'ND' means 'non-detected'.

FIG. 14 shows detection of MLV using MLV and ENV2 primer sets from formalin fixed paraffin embedded tissue (FFPE) infected with MLV. Paz3-emd spike in was added to either 100 ng fresh tumor sample that was frozen or added to 100 ng of a FFPE DNA tumor sample. qPCR was performed with the MLV and ENV2 primer sets.

FIG. 15 shows detection of XMRV in whole blood by RTPCR using XMRV specific primer sets XMRV gag, XMRV pol2, XMRV env.

DETAILED DESCRIPTION

Figure 1:
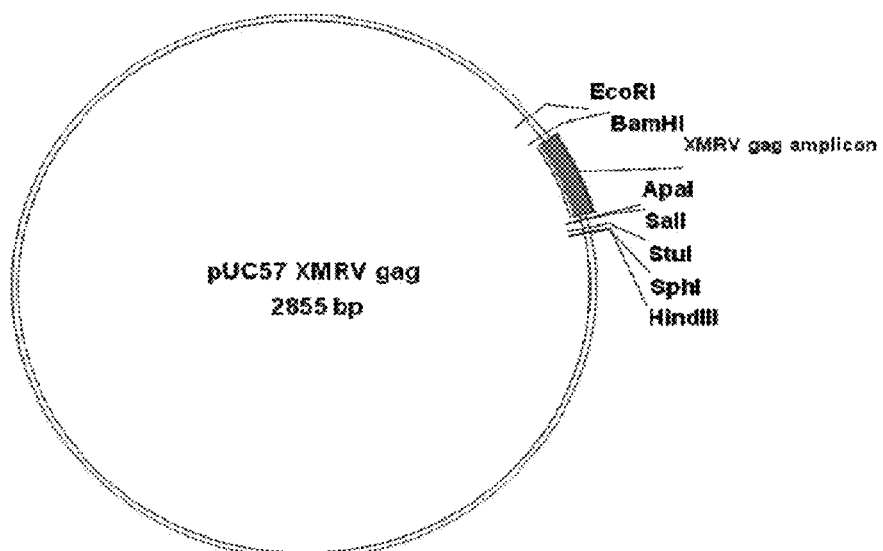
FIG. 1 shows XMRV gag standard in pUC57-XMRV gag plasmid DNA. The insert corresponds to nucleotides 628 to 764 of the XMRV VP62 clone sequence (NC_007815). The derived sequence is synthesized by BioBasic Inc and inserted into pUC57 backone at SmaI site between BamHI and ApaI sites.
Figure 2:
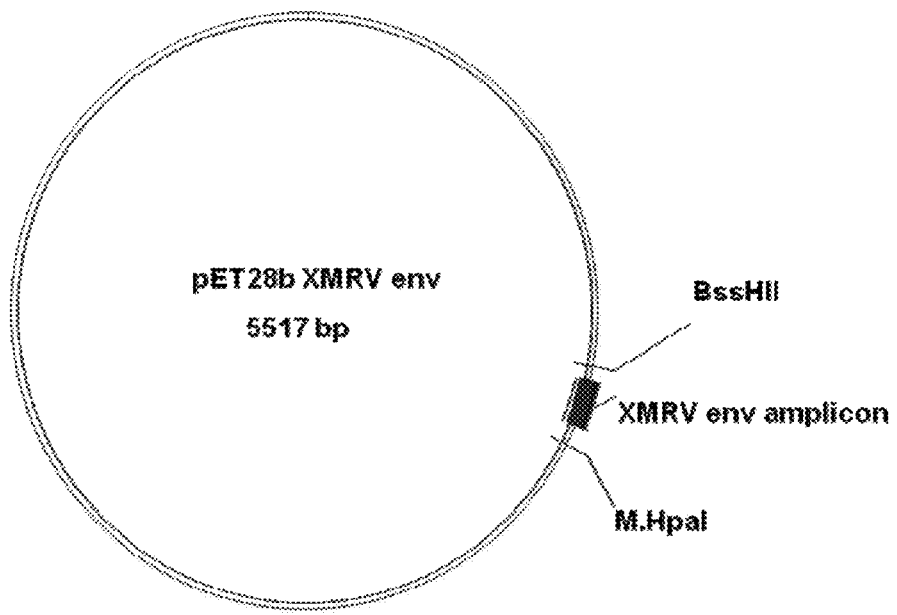
FIG. 2 shows XMRV env standard sequence in pET28b-XMRV env plasmid DNA. The insert corresponds to nucleotides 6252 to 6391 of the XMRV VP62 clone sequence (NC_007815). The derived sequence is synthesized by BioBasic Inc and inserted into pET28b+ backone at EcoRV site between BssHI and HpaI sites.
Figure 3:
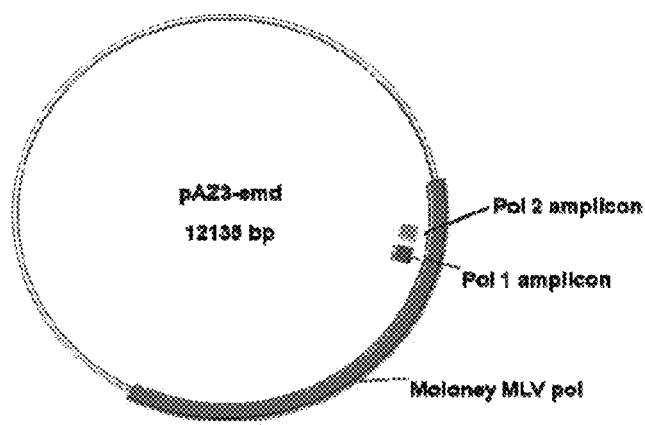
FIG. 3 shows the MLV pol1 and pol2 standard sequences in pAZ3-emd plasmid DNA which encodes an ecotropic Moloney MLV gag-pol, amphotropic env and IRES-GF-Pemd cassette downstream of the env (Logg et al. J. Virol. 75:6989-6998, 2001.
Figure 4:
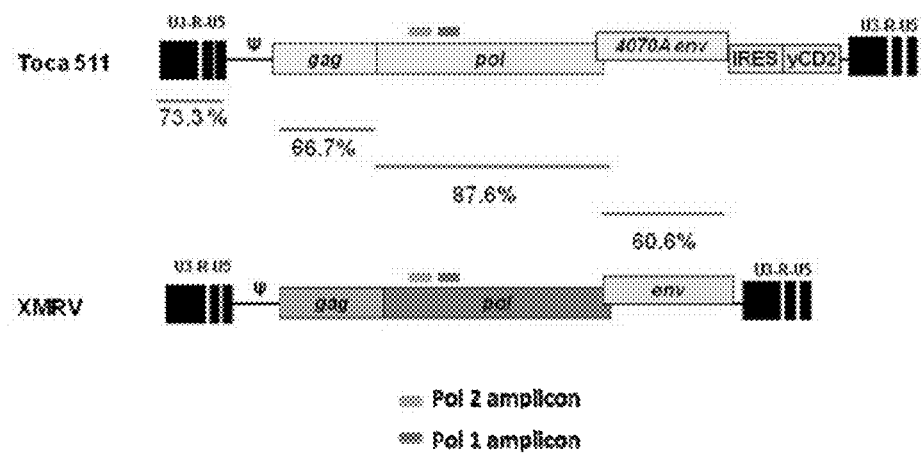
FIG. 4 shows a comparison of the sequences of Toca 511 (the proviral form) used to treat GBM patients and an XMRV provirus (VP 62, NCBI Reference Sequence NC_007815.1), noting the overall homology of the LTR, gag, pol and envelope regions. Also shown are the regions of the pol1 and pol2 amplicons. The MLV pol1 and pol2 standard sequences in pAZ3-emd plasmid DNA.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Unless defined otherwise, all technical and scientific terms used herein have the same meaning as commonly understood to one of ordinary skill in the art to which this disclosure belongs. Although any methods and reagents similar or equivalent to those described herein can be used in the practice of the disclosed methods and compositions, the exemplary methods and materials are now described.

As used herein and in the appended claims, the singular forms "a," "and," and "the" include plural referents unless the context clearly dictates otherwise. Thus, for example, reference to "an oligonucleotide" includes a plurality of such oligonucleotides and reference to "the polynucleotide" includes reference to one or more polynucleotides known to those skilled in the art, and so forth.

The detection of XMRV or MLV related retroviruses by nucleic acid amplification techniques in human or animal tissues, blood or plasma/serum is of use for determining prostate cancer and risk thereof, chronic fatigue system and risk thereof, contamination of blood supply and tissue donation material and in following the status of subjects undergoing therapy with an MLV derived therapeutic virus comprising a heterologous genetic sequence such as, for example, an engineered retroviral replicatog virus based on amphotropic MLV (e.g., Toca 511). For example, the methods and compositions of the disclosure can be used to monitor therapy with an retroviral vector comprising sequences with substantial identity to MLV, in determining if recombination takes place between the therapeutic vector and XMRV or other MLV related natural infections, and for determining if a subject carries XMRV or another MLV related naturally occurring virus. Such assays are also useful for screening the blood supply to exclude subjects that are positive for XMRV or other MLV related retroviruses. Such assays also can be used to determine levels of MLV related virus over time, and provide information when it would be useful to start administering antiretroviral therapies that are also active against MLV such as, for example, AZT (Sakuma et al., Virology, 2009; Powell et al., J. Virol., 73:8813-8816, 1999; G. B. Beck-Engeser, PNAS, 2009). Such assays when used with histopathology samples can be used to determine the presence or absence of XMRV or other MLV related retroviruses in a patients stored sample or to determine the epidemiology of the XMRV or MLV related virus. Such assays can also be used to monitor patients to whom therapeutic vectors based on replicating MLV vectors have been administered. These measurements can be used to track the safety of the therapy over time (e.g., to 15 years and beyond) as high persistent levels (greater than 30,000, 100,000 or 300,000 copies/microgram) of MLV in genomic DNA or greater than 30,000 100,000 or 300,000 RNA copies/ml plasma) or increasing levels of these over time, can be used as a signal to more closely monitor for diseases that could be secondary to a therapy using an gene therapy vector comprising MLV or MLV-related sequences, such as leukemia or to start antiretroviral therapy. However, these measurements can also be used to judge the extent of replication of the MLV or MLV-related vector in a target tissue (i.e., efficacy or susceptibility to successful treatment) because of the possibility of "spill" into the circulatory system. Other uses of these assays for clinical monitoring will be apparent to those skilled in the art.

Engineered retroviral vectors that can be monitored include those set forth below:

```
RCR Vector - pAC-yCD2
                                                           (SEQ ID NO: 22)
    tagttattaa tagtaatcaa ttacggggtc attagttcat agcccatata tggagttccg cgttacataa cttacggtaa atggcccgcc tggctgaccg cccaacgacc cccgcccatt gacgtcaata atgacgtatg ttcccatagt aacgccaata gggactttcc attgacgtca atgggtggag tatttacggt aaactgccca cttggcagta catcaagtgt atcatatgcc aagtacgccc cctattgacg tcaatgacgg taaatggccc gcctggcatt atgcccagta catgacctta tgggactttc ctacttggca gtacatctac gtattagtca tcgctattac catggtgatg cggttttggc agtacatcaa tgggcgtgga tagcggtttg actcacgggg atttccaagt ctccacccca ttgacgtcaa tgggagtttg ttttggcacc aaaatcaacg ggactttcca aaatgtcgta acaactccgc cccattgacg caaatgggcg gtaggcgtgt acggtgggag gtctatataa gcagagctgg tttagtgaac cggcgccagt cctccgattg actgagtcgc ccgggtaccc gtgtatccaa taaaccctct tgcagttgca tccgacttgt ggtctcgctg ttccttggga gggtctcctc tgagtgattg actacccgtc agcggggtc tttcatttgg gggctcgtcc gggatcggga gacccctgcc cagggaccac cgacccacca ccgggaggta agctggccag caacttatct gtgtctgtcc gattgtctag tgtctatgac tgattttatg cgcctgcgtc ggtactagtt agctaactag ctctgtatct ggcggacccg tggtggaact gacgagttcg gaacacccgg ccgcaaccct gggagacgtc ccagggactt cgggggccgt ttttgtggcc cgacctgagt ccaaaaatcc cgatcgtttt ggactctttg gtgcaccccc cttagaggag ggatatgtgg ttctggtagg agacgagaac ctaaaacagt tcccgcctcc gtctgaattt ttgctttcgg tttgggaccg aagccgcgcc gcgcgtcttg tctgctgcag catcgttctg tgttgtctct gtctgactgt gtttctgtat ttgtctgaga atatgggcca gactgttacc actcccttaa gtttgacctt aggtcactgg aaagatgtcg agcggatcgc tcacaaccag tcggtagatg tcaagaagag acgttgggtt accttctgct ctgcagaatg gccaacccttt aacgtcggat ggccgcgaga cggcacctttt aaccgagacc tcatcaccca ggttaagatc aaggtctttt cacctggccc gcatggacac ccagaccagg tcccctacat cgtgacctgg gaagccttgg cttttgaccc ccctccctgg gtcaagccct ttgtacaccc taagcctccg cctcctcttc ctccatccgc ccgtctctc cccttgaac ctcctcgttc gaccccgcct cgatcctccc tttatccagc cctcactcct tctctaggcg ccaaacctaa acctcaagtt ctttctgaca gtgggggggcc gctcatcgac ctacttacag
```

-continued

```
aagaccccc    gccttatagg    gacccaagac    caccccttc    cgacagggac    ggaaatggtg gagaagcgac    ccctgcggga    gaggcaccgg    acccctcccc    aatggcatct    cgcctacgtg ggagacggga    gcccctgtg     gccgactcca    ctacctcgca    ggcattcccc    ctccgcgcag gaggaaacgg    acagcttcaa    tactggccgt    tctcctcttc    tgacctttac    aactggaaaa ataataaccc    ttcttttct     gaagatccag    gtaaactgac    agctctgatc    gagtctgttc tcatcaccca    tcagcccacc    tgggacgact    gtcagcagct    gttggggact    ctgctgaccg gagaagaaaa    acaacgggtg    ctcttagagg    ctagaaaggc    ggtgcggggc    gatgatgggc gccccactca    actgcccaat    gaagtcgatg    ccgcttttcc    cctcgagcgc    ccagactggg attacaccac    ccaggcaggt    aggaaccacc    tagtccacta    tcgccagttg    ctcctagcgg gtctccaaaa    cgcgggcaga    agccccacca    atttggccaa    ggtaaaagga    ataacacaag gcccaatga    gtctccctcg     gccttcctag    agagacttaa    ggaagcctat    cgcaggtaca ctccttatga    ccctgaggac    ccagggcaag    aaactaatgt    gtctatgtct    ttcatttggc agtctgcccc    agacattggg    agaaagttag    agaggttaga    agatttaaaa    aacaagacgc ttggagattt    ggttagagag    gcagaaaaga    tctttaataa    acgagaaacc    ccggaagaaa gagaggaacg    tatcaggaga    gaaacagagg    aaaaagaaga    acgccgtagg    acagaggatg agcagaaaga    gaaagaaaga    gatcgtagga    gacatagaga    gatgagcaag    ctattggcca ctgtcgttag    tggacagaaa    caggatagac    agggaggaga    acgaaggagg    tcccaactcg atcgcgacca    gtgtgcctac    tgcaaagaaa    aggggcactg    ggctaaagat    tgtcccaaga aaccacgagg    acctcgggga    ccaagacccc    agacctccct    cctgacccta    gatgactagg gaggtcaggg    tcaggagccc    cccctgaac    ccaggataac     cctcaaagtc    ggggggcaac ccgtcacctt    cctggtagat    actggggccc    aacactccgt    gctgacccaa    aatcctggac ccctaagtga    taagtctgcc    tgggtccaag    gggctactgg    aggaaagcgg    tatcgctgga ccacggatcg    caaagtacat    ctagctaccg    gtaaggtcac    ccactctttc    ctccatgtac cagactgtcc    ctatcctctg    ttaggaagag    atttgctgac    taaactaaaa    gcccaaatcc actttgaggg    atcaggagcc    caggttatgg    gaccaatggg    gcagcccctg    caagtgttga ccctaaatat    agaagatgag    catcggctac    atgagacctc    aaaagagcca    gatgtttctc tagggtccac    atggctgtct    gattttcctc    aggcctgggc    ggaaaccggg    ggcatgggac tggcagttcg    ccaagctcct    ctgatcatac    ctctgaaagc    aacctctacc    cccgtgtcca taaaacaata    cccatgtca    caagaagcca     gactggggat    caagcccac     atacagagac tgttggacca    gggaatactg    gtaccctgcc    agtcccctg     gaacacgccc    ctgctacccg ttaagaaacc    agggactaat    gattataggc    ctgtccagga    tctgagagaa    gtcaacaagc gggtggaaga    catccacccc    accgtgccca    acccttacaa    cctcttgagc    gggctcccac cgtcccacca    gtggtacact    gtgcttgatt    taaaggatgc    cttttctgc     ctgagactcc accccaccag    tcagcctctc    ttcgcctttg    agtggagaga    tccagagatg    ggaatctcag gacaattgac    ctggaccaga    ctcccacagg    gtttcaaaaa    cagtcccacc    ctgtttgatg aggcactgca    cagagaccta    gcagacttcc    ggatccagca    cccagacttg    atcctgctac agtacgtgga    tgacttactg    ctggccgcca    cttctgagct    agactgccaa    caaggtactc gggccctgtt    acaaaccta    gggaacctcg     ggtatcgggc    ctcggccaag    aaagcccaaa tttgccagaa    acaggtcaag    tatctggggt    atcttctaaa    agagggtcag    agatggctga ctgaggccag    aaaagagact    gtgatggggc    agcctactcc    gaagacccct    cgacaactaa gggagttcct    agggacggca    ggcttctgtc    gcctctggat    ccctgggttt    gcagaaatgg
```

```
cagcccccctt gtaccctctc accaaaacgg ggactctgtt taattggggc ccagaccaac aaaaggccta tcaagaaatc aagcaagctc ttctaactgc cccagccctg gggttgccag atttgactaa gcccttttgaa ctctttgtcg acgagaagca gggctacgcc aaaggtgtcc taacgcaaaa actgggacct tggcgtcggc cggtggccta cctgtccaaa aagctagacc cagtagcagc tgggtggccc ccttgcctac ggatggtagc agccattgcc gtactgacaa aggatgcagg caagctaacc atgggacagc cactagtcat tctggccccc catgcagtag aggcactagt caaacaaccc cccgaccgct ggctttccaa cgcccggatg actcactatc aggccttgct tttggacacg gaccgggtcc agttcggacc ggtggtagcc ctgaacccgg ctacgctgct cccactgcct gaggaagggc tgcaacacaa ctgccttgat atcctggccg aagcccacgg aacccgaccc gacctaacgg accagccgct cccagacgcc gaccacacct ggtacacgga tggaagcagt ctcttacaag agggacagcg taaggcggga gctgcggtga ccaccgagac cgaggtaatc tgggctaaag ccctgccagc cgggacatcc gctcagcggg ctgaactgat agcactcacc caggccctaa agatggcaga aggtaagaag ctaaatgttt atactgatag ccgttatgct tttgctactg cccatatcca tggagaaata tacagaaggc gtgggttgct cacatcagaa ggcaaagaga tcaaaaataa agacgagatc ttggccctac taaaagccct ctttctgccc aaaagactta gcataatcca ttgtccagga catcaaaagg gacacagcgc cgaggctaga ggcaaccgga tggctgacca gcggcccga aaggcagcca tcacagagac tccagacacc tctaccctcc tcatagaaaa ttcatcaccc tacacctcag aacattttca ttacacagtg actgatataa aggacctaac caagttgggg gccatttatg ataaaacaaa gaagtattgg gtctaccaag gaaaacctgt gatgcctgac cagtttactt ttgaattatt agactttctt catcagctga ctcacctcag cttctcaaaa atgaaggctc tcctagagag aagccacagt ccctactaca tgctgaaccg ggatcgaaca ctcaaaaata tcactgagac ctgcaaagct tgtgcacaag tcaacgccag caagtctgcc gttaaacagg gaactagggt ccgcgggcat cggcccggca ctcattggga gatcgatttc accgagataa agcccggatt gtatggctat aaatatcttc tagtttttat agatacctttt tctggctgga tagaagcctt cccaaccaag aaagaaaccg ccaaggtcgt aaccaagaag ctactagagg agatcttccc caggttcggc atgcctcagg tattgggaac tgacaatggg cctgccttcg tctccaaggt gagtcagaca gtggccgatc tgttggggat tgattggaaa ttacattgtg catacagacc ccaaagctca ggccaggtag aaagaatgaa tagaaccatc aaggagactt taactaaatt aacgcttgca actggctcta gagactgggt gctcctactc cccttagccc tgtaccgagc ccgcaacacg ccgggccccc atggcctcac cccatatgag atcttatatg gggcaccccc gccccttgta aacttccctg accctgacat gacaagagtt actaacagcc cctctctcca agctcactta caggctctct acttagtcca gcacgaagtc tggagacctc tggcggcagc ctaccaagaa caactggacc gaccggtggt acctcaccct taccgagtcg gcgacacagt gtgggtccgc cgacaccaga ctaagaacct agaacctcgc tggaaaggac cttacacagt cctgctgacc accccaccg ccctcaaagt agacggcatc gcagcttgga tacacgccgc ccacgtgaag gctgccgacc ccggggtgg accatcctct agactgacat ggcgcgttca acgctctcaa aaccccctca agataagatt aacccgtgga agcccttaat agtcatggga gtcctgttag gagtagggat ggcagagagc cccatcagg tctttaatgt aacctggaga gtcaccaacc tgatgactgg gcgtaccgcc aatgccacct ccctcctggg aactgtacaa gatgccttcc caaaattata ttttgatcta tgtgatctgg tcggagagga
```

-continued

```
gtgggaccct tcagaccagg aaccgtatgt cgggtatggc tgcaagtacc ccgcagggag acagcggacc cggacttttg acttttacgt gtgccctggg cataccgtaa agtcggggtg tgggggacca ggagagggct actgtggtaa atgggggtgt gaaaccaccg gacaggctta ctggaagccc acatcatcgt gggacctaat ctcccttaag cgcggtaaca ccccctggga cacgggatgc tctaaagttg cctgtggccc ctgctacgac ctctccaaag tatccaattc cttccaaggg gctactcgag ggggcagatg caaccctcta gtcctagaat tcactgatgc aggaaaaaag gctaactggg acgggcccaa atcgtgggga ctgagactgt accggacagg aacagatcct attaccatgt tctccctgac ccggcaggtc cttaatgtgg gaccccgagt ccccatagg cccaacccag tattacccga ccaaagactc ccttcctcac aatagagat tgtaccggct ccacagccac ctagcccct caataccagt tacccccctt ccactaccag tacaccctca acctcccta caagtccaag tgtcccacag ccaccccag gaactggaga tagactacta gctctagtca aaggagccta tcaggcgctt aacctcacca atcccgacaa gacccaagaa tgttggctgt gcttagtgtc gggacctcct tattacgaag gagtagcggt cgtgggcact taccaatc attccaccgc tccggccaac tgtacggcca cttcccaaca taagcttacc ctatctgaag tgacaggaca gggcctatgc atgggggcag tacctaaaac tcaccaggcc ttatgtaaca ccacccaaag cgccggctca ggatcctact accttgcagc acccgccgga acaatgtggg cttgcagcac tggattgact ccctgcttgt ccaccacggt gctcaatcta accacagatt attgtgtatt agttgaactc tggcccagag taatttacca ctcccccgat tatatgtatg gtcagcttga acagcgtacc aaatataaaa gagagccagt atcattgacc ctggcccttc tactaggagg attaaccatg ggagggattg cagctggaat agggacgggg accactgcct taattaaaac ccagcagttt gagcagcttc atgccgctat ccagacagac ctcaacgaag tcgaaaagtc aattaccaac ctagaaaagt cactgacctc gttgtctgaa gtagtcctac agaaccgcag aggcctagat tgctattcc taaaggaggg aggtctctgc gcagccctaa aagaagaatg ttgttttttat gcagaccaca cggggctagt gagagacagc atggccaaat taagagaaag gcttaatcag agacaaaaac tatttgagac aggccaagga tggttcgaag ggctgtttaa tagatccccc tggtttacca ccttaatctc caccatcatg ggacctctaa tagtactctt actgatctta ctctttggac cttgcattct caatcgattg gtccaatttg ttaaagacag gatctcagtg gtccaggctc tggttttgac tcagcaatat caccagctaa aacccataga gtacgagcca tgaacgcgtt actggccgaa gccgcttgga ataaggccgg tgtgcgtttg tctatatgtt attttccacc atattgccgt cttttggcaa tgtgagggcc cggaaacctg gccctgtctt cttgacgagc attcctaggg gtctttcccc tctcgccaaa ggaatgcaag gtctgttgaa tgtcgtgaag aagcagttc ctctggaagc ttcttgaaga caaacaacgt ctgtagcgac cctttgcagg cagcggaacc ccccacctgg cgacaggtgc ctctgcggcc aaaagccacg tgtataagat acacctgcaa aggcggcaca accccagtgc cacgttgtga gttggatagt tgtggaaaga gtcaaatggc tctcctcaag cgtattcaac aaggggctga aggatgccca gaaggtaccc cattgtatgg gatctgatct ggggcctcgg tgcacatgct ttacatgtgt ttagtcgagg ttaaaaaaac gtctaggccc cccgaaccac ggggacgtgg ttttcctttg aaaaacacga ttataaatgg tgaccggcgg catggcctcc aagtgggatc aaaagggcat ggatatcgct tacgaggagg ccctgctggg ctacaaggag ggcggcgtgc ctatcggcgg ctgtctgatc aacaacaagg acggcagtgt gctgggcagg ggccacaaca tgaggttcca gaagggctcc gccacccctg
```

-continued

```
acggcgagat ctccaccctg gagaactgtg gcaggctgga gggcaaggtg tacaaggaca ccacccgtgta caccaccctg tcccttgtg acatgtgtac cggcgctatc atcatgtacg gcatccctag gtgtgtgatc ggcgagaacg tgaacttcaa gtccaagggc gagaagtacc tgcaaaccag gggccacgag gtggtggttg ttgacgatga gaggtgtaag aagctgatga agcagttcat cgacgagagg cctcaggact ggttcgagga tatcggcgag taagcggccg cagataaaat aaaagatttt atttagtctc cagaaaaagg ggggaatgaa agaccccacc tgtaggtttg gcaagctagc ttaagtaacg ccattttgca aggcatggaa aaatacataa ctgagaatag agaagttcag atcaaggtca ggaacagatg gaacagctga atatgggcca aacaggatat ctgtggtaag cagttcctgc cccggctcag ggccaagaac agatggaaca gctgaatatg ggccaaacag gatatctgtg gtaagcagtt cctgcccggg ctcagggcca agaacagatg gtccccagat gcggtccagc cctcagcagt ttctagagaa ccatcagatg tttccagggt gccccaagga cctgaaatga ccctgtgcct tatttgaact aaccaatcag ttcgcttctc gcttctgttc gcgcgcttct gctccccgag ctcaataaaa gagcccacaa cccctcactc ggggcgccag tcctccgatt gactgagtcg cccgggtacc cgtgtatcca ataaaccctc ttgcagttgc atccgacttg tggtctcgct gttccttggg agggtctcct ctgagtgatt gactacccgt cagcgggggt ctttcattac atgtgagcaa aaggccagca aaaggccagg aaccgtaaaa aggccgcgtt gctggcgttt ttccataggc tccgcccccc tgacgagcat cacaaaaatc gacgctcaag tcagaggtgg cgaaacccga caggactata aagataccag gcgtttcccc ctggaagctc cctcgtgcgc tctcctgttc cgaccctgcc gcttaccgga tacctgtccg cctttctccc ttcgggaagc gtggcgcttt ctcaatgctc acgctgtagg tatctcagtt cggtgtaggt cgttcgctcc aagctgggct gtgtgcacga accccccgtt cagcccgacc gctgcgcctt atccggtaac tatcgtcttg agtccaaccc ggtaagacac gacttatcgc cactggcagc agccactggt aacaggatta gcagagcgag gtatgtaggc ggtgctacag agttcttgaa gtggtggcct aactacggct acactagaag gacagtattt ggtatctgcg ctctgctgaa gccagttacc ttcggaaaaa gagttggtag ctcttgatcc ggcaaacaaa ccaccgctgg tagcggtggt ttttttgttt gcaagcagca gattacgcgc agaaaaaaag gatctcaaga agatcctttg atcttttcta cggggtctga cgctcagtgg aacgaaaact cacgttaagg gattttggtc atgagattat caaaaaggat cttcacctag atcctttaa attaaaaatg aagttttaaa tcaatctaaa gtatatatga gtaaacttgg tctgacagtt accaatgctt aatcagtgag gcacctatct cagcgatctg tctatttcgt tcatccatag ttgcctgact ccccgtcgtg tagataacta cgatacggga gggcttacca tctggcccca gtgctgcaat gataccgcga gacccacgct caccggctcc agatttatca gcaataaacc agccagccgg aagggccgag cgcagaagtg gtcctgcaac tttatccgcc tccatccagt ctattaattg ttgccgggaa gctagagtaa gtagttcgcc agttaatagt ttgcgcaacg ttgttgccat tgctgcaggc atcgtggtgt cacgctcgtc gtttggtatg gcttcattca gctccggttc ccaacgatca aggcgagtta catgatcccc catgttgtgc aaaaaagcgg ttagctcctt cggtcctccg atcgttgtca gaagtaagtt ggccgcagtg ttatcactca tggttatggc agcactgcat aattctctta ctgtcatgcc atccgtaaga tgcttttctg tgactggtga gtactcaacc aagtcattct gagaatagtg tatgcggcga ccgagttgct cttgcccggc gtcaacacgg ataataccg cgccacatag cagaacttta aaagtgctca tcattggaaa acgttcttcg ggcgaaaac tctcaaggat
```

-continued

```
cttaccgctg ttgagatcca gttcgatgta acccactcgt gcacccaact gatcttcagc atcttttact ttcaccagcg tttctgggtg agcaaaaaca ggaaggcaaa atgccgcaaa aaagggaata agggcgacac ggaaatgttg aatactcata ctcttccttt ttcaatatta ttgaagcatt tatcagggtt attgtctcat gagcggatac atatttgaat gtatttagaa aaataaacaa atagggggttc cgcgcacatt tccccgaaaa gtgccacctg acgtctaaga aaccattatt atcatgacat taacctataa aaataggcgt atcacgaggc cctttcgtct tcaagaattc at
```

RCR Vector - pAC-yCD (SEQ ID NO: 23)
```
tagttattaa tagtaatcaa ttacggggtc attagttcat agcccatata tggagttccg cgttacataa cttacggtaa atggcccgcc tggctgaccg cccaacgacc cccgcccatt gacgtcaata atgacgtatg ttcccatagt aacgccaata gggactttcc attgacgtca atgggtggag tatttacggt aaactgccca cttggcagta catcaagtgt atcatatgcc aagtacgccc cctattgacg tcaatgacgg taaatggccc gcctggcatt atgcccagta catgacctta tgggactttc ctacttggca gtacatctac gtattagtca tcgctattac catggtgatg cggttttggc agtacatcaa tgggcgtgga tagcggtttg actcacgggg atttccaagt ctccacccca ttgacgtcaa tgggagtttg ttttggcacc aaaatcaacg ggactttcca aaatgtcgta acaactccgc cccattgacg caaatgggcg gtaggcgtgt acggtgggag gtctatataa gcagagctgg tttagtgaac cggcgccagt cctccgattg actgagtcgc ccgggtaccc gtgtatccaa taaaccctct tgcagttgca tccgacttgt ggtctcgctg ttccttggga gggtctcctc tgagtgattg actacccgtc agcgggggtc tttcatttgg gggctcgtcc gggatcggga gacccctgcc cagggaccac cgacccacca ccgggaggta agctggccag caacttatct gtgtctgtcc gattgtctag tgtctatgac tgattttatg cgcctgcgtc ggtactagtt agctaactag ctctgtatct ggcggacccg tggtggaact gacgagttcg gaacacccgg ccgcaaccct gggagacgtc ccagggactt cggggggccgt ttttgtggcc cgacctgagt ccaaaaatcc cgatcgtttt ggactctttg gtgcaccccc cttagaggag ggatatgtgg ttctggtagg agacgagaac ctaaaacagt tcccgcctcc gtctgaattt ttgctttcgg tttgggaccg aagccgcgcc gcgcgtcttg tctgctgcag catcgttctg tgttgtctct gtctgactgt gtttctgtat ttgtctgaga atatgggcca gactgttacc actcccttaa gtttgacctt aggtcactgg aaagatgtcg agcggatcgc tcacaaccag tcggtagatg tcaagaagag acgttgggtt accttctgct ctgcagaatg gccaaccttt aacgtcggat ggccgcgaga cggcaccttt aaccgagacc tcatcaccca ggttaagatc aaggtctttt cacctggccc gcatggacac ccagaccagg tccctacat cgtgacctgg gaagccttgg cttttgaccc cctccctgg gtcaagccct ttgtacaccc taagcctccg cctcctcttc ctccatccgc cccgtctctc cccttgaac ctcctcgttc gaccccgcct cgatcctccc tttatccagc cctcactcct tctctaggcg ccaaacctaa acctcaagtt ctttctgaca gtggggggcc gctcatcgac ctacttacag aagaccccc gccttatagg gacccaagac caccccttc cgacagggac ggaaatggtg gagaagcgac ccctgcggga gaggcaccgg acccctcccc aatggcatct cgcctacgtg ggagacggga gccccctgtg gccgactcca ctacctcgca ggcattcccc ctccgcgcag gaggaaacgg acagcttcaa tactggccgt tctcctcttc tgacctttac aactggaaaa ataataaccc ttcttttttct gaagatccag gtaaactgac agctctgatc gagtctgttc
```

-continued

```
tcatcaccca tcagcccacc tgggacgact gtcagcagct gttggggact ctgctgaccg gagaagaaaa acaacgggtg ctcttagagg ctagaaaggc ggtgcggggc gatgatgggc gccccactca actgcccaat gaagtcgatg ccgcttttcc cctcgagcgc ccagactggg attacaccac ccaggcaggt aggaaccacc tagtccacta tcgccagttg ctcctagcgg gtctccaaaa cgcgggcaga agccccacca atttggccaa ggtaaaagga ataacacaag ggcccaatga gtctccctcg gccttcctag agagacttaa ggaagcctat cgcaggtaca ctccttatga ccctgaggac ccagggcaag aaactaatgt gtctatgtct ttcatttggc agtctgcccc agacattggg agaaagttag agaggttaga agatttaaaa aacaagacgc ttggagattt ggttagagag gcagaaaaga tctttaataa acgagaaacc ccggaagaaa gagaggaacg tatcaggaga gaaacagagg aaaagaaga acgccgtagg acagaggatg agcagaaaga gaaagaaaga gatcgtagga gacatagaga gatgagcaag ctattggcca ctgtcgttag tggacagaaa caggatagaa agggaggaga acgaaggagg tcccaactcg atcgcgacca gtgtgcctac tgcaaagaaa aggggcactg ggctaaagat tgtcccaaga aaccacgagg acctcgggga ccaagacccc agacctccct cctgacccta gatgactagg gaggtcaggg tcaggagccc cccctgaac ccaggataac cctcaaagtc gggggcaac ccgtcacctt cctggtagat actggggccc aacactccgt gctgacccaa atcctggac ccctaagtga taagtctgcc tgggtccaag gggctactgg aggaaagcgg tatcgctgga ccacggatcg caaagtacat ctagctaccg gtaaggtcac ccactctttc ctccatgtac cagactgtcc ctatcctctg ttaggaagag atttgctgac taaactaaaa gcccaaatcc actttgaggg atcaggagcc caggttatgg gaccaatggg gcagcccctg caagtgttga ccctaaaatat agaagatgag catcggctac atgagacctc aaaagagcca gatgtttctc tagggtccac atggctgtct gatttttcctc aggcctgggc ggaaaccggg ggcatgggac tggcagttcg ccaagctcct ctgatcatac ctctgaaagc aacctctacc cccgtgtcca taaaacaata ccccatgtca caagaagcca gactggggat caagccccac atacagagac tgttggacca gggaatactg gtaccctgcc agtcccctg gaacacgccc ctgctacccg ttaagaaacc agggactaat gattataggc ctgtccagga tctgagagaa gtcaacaagc gggtggaaga catccacccc accgtgccca acccttacaa cctcttgagc gggctcccac cgtcccacca gtggtacact gtgcttgatt taaaggatgc cttttttctgc ctgagactcc accccaccag tcagcctctc ttcgcctttg agtggagaga tccagagatg ggaatctcag gacaattgac ctggaccaga ctcccacagg gtttcaaaaa cagtcccacc ctgtttgatg aggcactgca cagagaccta gcagacttcc ggatccagca cccagacttg atcctgctac agtacgtgga tgacttactg ctggccgcca cttctgagct agactgccaa caaggtactc gggccctgtt acaaaccta gggaaactcg ggtatcgggc ctcggccaag aaagcccaaa tttgccagaa acaggtcaag tatctggggt atcttctaaa agagggtcag agatggctga ctgaggccag aaaagagact gtgatggggc agcctactcc gaagacccct cgacaactaa gggagttcct agggacggca ggcttctgtc gcctctggat ccctgggttt gcagaaatgg cagccccctt gtaccctctc accaaaacgg ggactctgtt taattggggc ccagaccaac aaaaggccta tcaagaaatc aagcaagctc ttctaactgc cccagccctg ggttgccag atttgactaa gcccttttgaa ctctttgtcg acgagaagca gggctacgcc aaaggtgtcc taacgcaaaa actgggacct tggcgtcggc cggtggccta cctgtccaaa aagctagacc cagtagcagc tgggtggccc ccttgcctac ggatggtagc agccattgcc gtactgacaa
```

-continued

```
aggatgcagg caagctaacc atgggacagc cactagtcat tctggccccc catgcagtag aggcactagt caaacaaccc cccgaccgct ggctttccaa cgcccggatg actcactatc aggccttgct tttggacacg gaccgggtcc agttcggacc ggtggtagcc ctgaacccgg ctacgctgct cccactgcct gaggaagggc tgcaacacaa ctgccttgat atcctggccg aagcccacgg aacccgaccc gacctaacgg accagccgct cccagacgcc gaccacacct ggtacacgga tggaagcagt ctcttacaag agggacagcg taaggcggga gctgcggtga ccaccgagac cgaggtaatc tgggctaaag ccctgccagc cgggacatcc gctcagcggg ctgaactgat agcactcacc caggccctaa agatggcaga aggtaagaag ctaaatgttt atactgatag ccgttatgct tttgctactg cccatatcca tggagaaata tacagaaggc gtgggttgct cacatcagaa ggcaaagaga tcaaaaataa agacgagatc ttggccctac taaaagccct ctttctgccc aaaagactta gcataatcca ttgtccagga catcaaaagg gacacagcgc cgaggctaga ggcaaccgga tggctgacca gcggcccga aaggcagcca tcacagagac tccagacacc tctaccctcc tcatagaaaa ttcatcaccc tacacctcag aacattttca ttacacagtg actgatataa aggacctaac caagttgggg gccatttatg ataaaacaaa gaagtattgg gtctaccaag gaaaacctgt gatgcctgac cagtttactt ttgaattatt agactttctt catcagctga ctcacctcag cttctcaaaa atgaaggctc tcctagagag aagccacagt ccctactaca tgctgaaccg ggatcgaaca ctcaaaaata tcactgagac ctgcaaagct tgtgcacaag tcaacgccag caagtctgcc gttaaacagg gaactagggt ccgcgggcat cggcccggca ctcattggga gatcgatttc accgagataa agcccggatt gtatggctat aaatatcttc tagtttttat agatacctt tctggctgga tagaagcctt cccaaccaag aaagaaaccg ccaaggtcgt aaccaagaag ctactagagg agatcttccc caggttcggc atgcctcagg tattgggaac tgacaatggg cctgccttcg tctccaaggt gagtcagaca gtggccgatc tgttgggat tgattggaaa ttacattgtg catacagacc ccaaagctca ggccaggtag aaagaatgaa tagaaccatc aaggagactt taactaaatt aacgcttgca actggctcta gagactgggg gctcctactc cccttagccc tgtaccgagc ccgcaacacg ccgggccccc atggcctcac cccatatgag atcttatatg gggcaccccc gccccttgta aacttccctg accctgacat gacaagagtt actaacagcc cctctctcca agctcactta caggctctct acttagtcca gcacgaagtc tggagacctc tggcggcagc ctaccaagaa caactggacc gaccggtggt acctcaccct taccgagtcg gcgacacagt gtgggtccgc cgacaccaga ctaagaacct agaacctcgc tggaaaggac cttacacagt cctgctgacc acccccaccg ccctcaaagt agacggcatc gcagcttgga tacacgccgc ccacgtgaag gctgccgacc ccggggtgg accatcctct agactgacat ggcgcgttca acgctctcaa aacccccctca agataagatt aacccgtgga agcccttaat agtcatggga gtcctgttag gagtagggat ggcagagagc ccccatcagg tctttaatgt aacctggaga gtcaccaacc tgatgactgg gcgtaccgcc aatgccacct ccctcctggg aactgtacaa gatgccttcc caaaattata ttttgatcta tgtgatctgg tcggagagga gtgggaccct tcagaccagg aaccgtatgt cgggtatggc tgcaagtacc ccgcagggag acagcggacc cggactttg acttttacgt gtgccctggg cataccgtaa agtcggggtg tgggggacca ggagagggct actgtggtaa atgggggtgt gaaaccaccg gacaggctta ctggaagccc acatcatcgt gggacctaat ctcccttaag cgcggtaaca cccctgggga cacgggatgc tctaaagttg cctgtggccc ctgctacgac ctctccaaag tatccaattc
```

-continued

```
cttccaaggg gctactcgag gggggcagatg caaccctcta gtcctagaat tcactgatgc aggaaaaaag gctaactggg acgggcccaa atcgtgggga ctgagactgt accggacagg aacagatcct attaccatgt tctccctgac ccggcaggtc cttaatgtgg gaccccgagt ccccataggg cccaacccag tattacccga ccaaagactc ccttcctcac caatagagat tgtaccggct ccacagccac ctagcccccct caataccagt taccccccctt ccactaccag tacaccctca acctcccta caagtccaag tgtcccacag ccaccccag gaactggaga tagactacta gctctagtca aaggagccta tcaggcgctt aacctcacca atcccgacaa gacccaagaa tgttggctgt gcttagtgtc gggacctcct tattacgaag gagtagcggt cgtgggcact tataccaatc attccaccgc tccggccaac tgtacggcca cttcccaaca taagcttacc ctatctgaag tgacaggaca gggcctatgc atgggggcag tacctaaaac tcaccaggcc ttatgtaaca ccacccaaag cgccggctca ggatcctact accttgcagc acccgccgga acaatgtggg cttgcagcac tggattgact ccctgcttgt ccaccacggt gctcaatcta accacagatt attgtgtatt agttgaactc tggcccagag taatttacca ctcccccgat tatatgtatg gtcagcttga acagcgtacc aaatataaaa gagagccagt atcattgacc ctggcccttc tactaggagg attaaccatg ggagggattg cagctggaat agggacgggg accactgcct taattaaaac ccagcagttt gagcagcttc atgccgctat ccagacagac ctcaacgaag tcgaaaagtc aattaccaac ctagaaaagt cactgacctc gttgtctgaa gtagtcctac agaaccgcag aggcctagat ttgctattcc taaggaggg aggtctctgc gcagccctaa aagaagaatg ttgtttttat gcagaccaca cggggctagt gagagacagc atggccaaat taagagaaag gcttaatcag agacaaaaac tatttgagac aggccaagga tggttcgaag ggctgtttaa tagatccccc tggtttacca ccttaatctc caccatcatg ggacctctaa tagtactctt actgatctta ctctttggac cttgcattct caatcgattg gtccaatttg ttaaagacag gatctcagtg gtccaggctc tggttttgac tcagcaatat caccagctaa aacccataga gtacgagcca tgaacgcgtt actggccgaa gccgcttgga ataaggccgg tgtgcgtttg tctatatgtt attttccacc atattgccgt cttttggcaa tgtgagggcc cggaaacctg gccctgtctt cttgacgagc attcctaggg gtctttcccc tctcgccaaa ggaatgcaag gtctgttgaa tgtcgtgaag aagcagttc ctctggaagc ttcttgaaga caaacaacgt ctgtagcgac cctttgcagg cagcggaacc ccccacctgg cgacaggtgc ctctgcggcc aaaagccacg tgtataagat acacctgcaa aggcggcaca accccagtgc cacgttgtga gttggatagt tgtggaaaga gtcaaatggc tctcctcaag cgtattcaac aaggggctga aggatgccca gaaggtaccc cattgtatgg gatctgatct ggggcctcgg tgcacatgct ttacatgtgt ttagtcgagg ttaaaaaaac gtctaggccc cccgaaccac ggggacgtgg ttttccttg aaaaacacga ttataaatgg tgacagggg aatggcaagc aagtgggatc agaagggtat ggacattgcc tatgaggagg cggccttagg ttacaaagag ggtggtgttc ctattggcgg atgtcttatc aataacaaag acggaagtgt tctcggtcgt ggtcacaaca tgagatttca aaagggatcc gccacactac atggtgagat ctccactttg gaaaactgtg ggagattaga gggcaaagtg tacaaagata ccactttgta tacgacgctg tctccatgcg acatgtgtac aggtgccatc atcatgtatg gtattccacg ctgtgttgtc ggtgagaacg ttaatttcaa agtaagggc gagaaatatt tacaaactag aggtcacgag gttgttgttg ttgacgatga gaggtgtaaa aagatcatga aacaatttat cgatgaaaga cctcaggatt ggtttgaaga tattggtgag taggcggccg
```

```
cagataaaat aaaagatttt atttagtctc cagaaaaagg ggggaatgaa agaccccacc tgtaggtttg gcaagctagc ttaagtaacg ccattttgca aggcatggaa aaatacataa ctgagaatag agaagttcag atcaaggtca ggaacagatg gaacagctga atatgggcca aacaggatat ctgtggtaag cagttcctgc cccggctcag ggccaagaac agatggaaca gctgaatatg ggccaaacag atatctgtg gtaagcagtt cctgccccgg ctcagggcca agaacagatg gtccccagat gcggtccagc cctcagcagt ttctagagaa ccatcagatg tttccagggt gccccaagga cctgaaatga ccctgtgcct tatttgaact aaccaatcag ttcgcttctc gcttctgttc gcgcgcttct gctccccgag ctcaataaaa gagcccacaa cccctcactc ggggcgccag tcctccgatt gactgagtcg cccgggtacc cgtgtatcca ataaaccctc ttgcagttgc atccgacttg tggtctcgct gttccttggg agggtctcct ctgagtgatt gactacccgt cagcggtgggt ctttcattac atgtgagcaa aaggccagca aaaggccagg aaccgtaaaa aggccgcgtt gctggcgttt ttccataggc tccgcccccc tgacgagcat cacaaaaatc gacgctcaag tcagaggtgg cgaaacccga caggactata aagataccag gcgtttcccc ctggaagctc cctcgtgcgc tctcctgttc cgaccctgcc gcttaccgga tacctgtccg cctttctccc ttcgggaagc gtggcgcttt ctcaatgctc acgctgtagg tatctcagtt cggtgtaggt cgttcgctcc aagctgggct gtgtgcacga accccccgtt cagcccgacc gctgcgcctt atccggtaac tatcgtcttg agtccaaccc ggtaagacac gacttatcgc cactggcagc agccactggt aacaggatta gcagagcgag gtatgtaggc ggtgctacag agttcttgaa gtggtggcct aactacggct acactagaag gacagtattt ggtatctgcg ctctgctgaa gccagttacc ttcggaaaaa gagttggtag ctcttgatcc ggcaaacaaa ccaccgctgg tagcggtggt ttttttgttt gcaagcagca gattacgcgc agaaaaaaag gatctcaaga agatcctttg atcttttcta cggggtctga cgctcagtgg aacgaaaact cacgttaagg gattttggtc atgagattat caaaaaggat cttcacctag atccttttaa attaaaaatg aagttttaaa tcaatctaaa gtatatatga gtaaacttgg tctgacagtt accaatgctt aatcagtgag gcacctatct cagcgatctg tctatttcgt tcatccatag ttgcctgact ccccgtcgtg tagataacta cgatacggga gggcttacca tctggcccca gtgctgcaat gataccgcga gacccacgct caccggctcc agatttatca gcaataaacc agccagccgg aagggccgag cgcagaagtg gtcctgcaac tttatccgcc tccatccagt ctattaattg ttgccgggaa gctagagtaa gtagttcgcc agttaatagt ttgcgcaacg ttgttgccat tgctgcaggc atcgtggtgt cacgctcgtc gtttggtatg gcttcattca gctccggttc ccaacgatca aggcgagtta catgatcccc catgttgtgc aaaaaagcgg ttagctcctt cggtcctccg atcgttgtca gaagtaagtt ggccgcagtg ttatcactca tggttatggc agcactgcat aattctctta ctgtcatgcc atccgtaaga tgcttttctg tgactggtga gtactcaacc aagtcattct gagaatagtg tatgcggcga ccgagttgct cttgcccggc gtcaacacgg ataataccg cgccacatag cagaacttta aaagtgctca tcattggaaa acgttcttcg gggcgaaaac tctcaaggat cttaccgctg ttgagatcca gttcgatgta acccactcgt gcacccaact gatcttcagc atcttttact ttcaccagcg tttctgggtg agcaaaaaca ggaaggcaaa atgccgcaaa aaagggaata agggcgacac ggaaatgttg aatactcata ctcttccttt ttcaatatta ttgaagcatt tatcagggtt attgtctcat gagcggatac atatttgaat gtatttagaa aaataaacaa ataggggttc cgcgcacatt tccccgaaaa gtgccacctg acgtctaaga
```

-continued aaccattatt atcatgacat taacctataa aaataggcgt atcacgaggc cctttcgtct tcaagaattc at RCR Vector - pACE-CD (SEQ ID NO: 24)

tagttattaa tagtaatcaa ttacggggtc attagttcat agcccatata tggagttccg cgttacataa cttacggtaa atggcccgcc tggctgaccg cccaacgacc cccgcccatt gacgtcaata atgacgtatg ttcccatagt aacgccaata gggactttcc attgacgtca atgggtggag tatttacggt aaactgccca cttggcagta catcaagtgt atcatatgcc aagtacgccc cctattgacg tcaatgacgg taaatggccc gcctggcatt atgcccagta catgaccttacca tgggactttc ctacttggca gtacatctac gtattagtca tcgctattac catggtgatg cggttttggc agtacatcaa tgggcgtgga tagcggtttg actcacgggg atttccaagt ctccacccca ttgacgtcaa tgggagtttg ttttggcacc aaaatcaacg ggactttcca aaatgtcgta acaactccgc cccattgacg caaatgggcg gtaggcgtgt acggtgggag gtctatataa gcagagctgg tttagtgaac cggcgccagt cctccgattg actgagtcgc ccgggtaccc gtgtatccaa taaaccctct tgcagttgca tccgacttgt ggtctcgctg ttccttggga gggtctcctc tgagtgattg actacccgtc agcgggggtc tttcatttgg gggctcgtcc gggatcggga ccccctgcc cagggaccac cgacccacca ccggaggta agctggccag caacttatct gtgtctgtcc gattgtctag tgtctatgac tgatttatg cgcctgcgtc ggtactagtt agctaactag ctctgtatct ggcggacccg tggtggaact gacgagttcg gaacacccgg ccgcaaccct gggagacgtc ccagggactt cggggggccgt ttttgtggcc cgacctgagt ccaaaaatcc cgatcgtttt ggactctttg gtgcaccccc cttagaggag ggatatgtgg ttctggtagg agacgagaac ctaaaacagt tccgcctcc gtctgaattt tgctttcgg tttgggaccg aagccgcgcc gcgcgtcttg tctgctgcag catcgttctg tgttgtctct gtctgactgt gtttctgtat ttgtctgaga atatgggcca gactgttacc actcccttaa gtttgacctt aggtcactgg aaagatgtcg agcggatcgc tcacaaccag tcggtagatg tcaagaagag acgttgggtt accttctgct ctgcagaatg gccaaccttt aacgtcggat ggccgcgaga cggcaccttt aaccgagacc tcatcaccca ggttaagatc aaggtctttt cacctggccc gcatggacac ccagaccagg tccctacat cgtgacctgg gaagccttgg ctttgaccc cctcctgg gtcaagccct ttgtacaccc taagcctccg cctcctcttc ctccatccgc cccgtctctc cccttgaac ctcctcgttc gaccccgcct cgatcctccc tttatccagc cctcactcct tctctaggcg ccaaacctaa acctcaagtt ctttctgaca gtgggggggcc gctcatcgac ctacttacag aagaccccccc gccttatagg gacccaagac caccccttc cgacagggac ggaaatggtg gagaagcgac ccctgcggga gaggcaccgg acccctcccc aatggcatct cgcctacgtg ggagacggga gccccctgtg gccgactcca ctacctcgca ggcattcccc ctccgcgcag gaggaaacgg acagcttcaa tactggccgt tctcctcttc tgacctttac aactggaaaa ataataaccc ttcttttct gaagatccag gtaaactgac agctctgatc gagtctgttc tcatcaccca tcagcccacc tgggacgact gtcagcagct gttggggact ctgctgaccg gagaagaaaa acaacgggtg ctcttagagg ctagaaaggc ggtgcgggc gatgatgggc gccccactca actgcccaat gaagtcgatg ccgcttttcc cctcgagcgc ccagactggg attacaccac caggcaggt aggaaccacc tagtccacta tcgccagttg ctcctagcgg gtctccaaaa cgcgggcaga agccccacca atttggccaa ggtaaaagga ataacacaag -continued

```
ggcccaatga gtctccctcg gccttcctag agagacttaa ggaagcctat cgcaggtaca ctccttatga ccctgaggac ccagggcaag aaactaatgt gtctatgtct ttcatttggc agtctgcccc agacattggg agaaagttag agaggttaga agatttaaaa aacaagacgc ttggagattt ggttagagag gcagaaaaga tctttaataa acgagaaacc ccggaagaaa gagaggaacg tatcaggaga gaaacagagg aaaagaaga acgccgtagg acagaggatg agcagaaaga gaaagaaaga gatcgtagga gacatagaga gatgagcaag ctattggcca ctgtcgttag tggacagaaa caggatagac agggaggaga acgaaggagg tcccaactcg atcgcgacca gtgtgcctac tgcaaagaaa aggggcactg ggctaaagat tgtcccaaga aaccacgagg acctcgggga ccaagacccc agacctcect cctgacccta gatgactagg gaggtcaggg tcaggagccc ccccctgaac ccaggataac cctcaaagtc ggggggcaac ccgtcacctt cctggtagat actggggccc aacactccgt gctgacccaa aatcctggac ccctaagtga taagtctgcc tgggtccaag gggctactgg aggaaagcgg tatcgctgga ccacggatcg caaagtacat ctagctaccg gtaaggtcac ccactctttc ctccatgtac cagactgtcc ctatcctctg ttaggaagag atttgctgac taaactaaaa gcccaaatcc actttgaggg atcaggagcc caggttatgg gaccaatggg gcagccctg caagtgttga ccctaaatat agaagatgag catcggctac atgagacctc aaaagagcca gatgtttctc tagggtccac atggctgtct gattttcctc aggcctgggc ggaaaccggg ggcatgggac tggcagttcg ccaagctcct ctgatcatac ctctgaaagc aacctctacc cccgtgtcca taaaacaata ccccatgtca caagaagcca gactggggat caagcccac atacagagac tgttggacca gggaatactg gtaccctgcc agtcccctg gaacacgccc ctgctacccg ttaagaaacc agggactaat gattataggc ctgtccagga tctgagagaa gtcaacaagc gggtggaaga catccacccc accgtgccca acccttacaa cctcttgagc gggctcccac cgtcccacca gtggtacact gtgcttgatt taaaggatgc cttttctgc ctgagactcc accccaccag tcagcctctc ttcgcctttg agtggagaga tccagagatg ggaatctcag gacaattgac ctggaccaga ctcccacagg gtttcaaaaa cagtcccacc ctgtttgatg aggcactgca cagagaccta gcagacttcc ggatccagca cccagacttg atcctgctac agtacgtgga tgacttactg ctggccgcca cttctgagct agactgccaa caaggtactc gggccctgtt acaaacccta gggaacctcg ggtatcgggc ctcggccaag aaagcccaaa tttgccagaa acaggtcaag tatctggggt atcttctaaa agagggtcag agatggctga ctgaggccag aaaagagact gtgatggggc agcctactcc gaagacccct cgacaactaa gggagttcct agggacggca ggcttctgtc gcctctggat ccctgggttt gcagaaatgg cagccccctt gtaccctctc accaaaacgg ggactctgtt taattggggc ccagaccaac aaaaggccta tcaagaaatc aagcaagctc ttctaactgc cccagccctg gggttgccag atttgactaa gcccttttgaa ctctttgtcg acgagaagca gggctacgcc aaaggtgtcc taacgcaaaa actgggacct tggcgtcggc cggtggccta cctgtccaaa agctagacc cagtagcagc tgggtggccc ccttgcctac ggatggtagc agccattgcc gtactgacaa aggatgcagg caagctaacc atgggacagc cactagtcat tctggccccc catgcagtag aggcactagt caaacaaccc cccgaccgct ggctttccaa cgcccggatg actcactatc aggccttgct tttggacacg gaccgggtcc agttcggacc ggtggtagcc ctgaacccgg ctacgctgct cccactgcct gaggaagggc tgcaacacaa ctgccttgat atcctggccg aagcccacgg aacccgaccc gacctaacgg accagccgct cccagacgcc gaccacacct
```

-continued

```
ggtacacgga tggaagcagt ctcttacaag agggacagcg taaggcggga gctgcggtga ccaccgagac cgaggtaatc tgggctaaag ccctgccagc cgggacatcc gctcagcggg ctgaactgat agcactcacc caggccctaa agatggcaga aggtaagaag ctaaatgttt atactgatag ccgttatgct tttgctactg cccatatcca tggagaaata tacagaaggc gtgggttgct cacatcagaa ggcaaagaga tcaaaaataa agacgagatc ttggccctac taaaagccct ctttctgccc aaaagactta gcataatcca ttgtccagga catcaaaagg gacacagcgc cgaggctaga ggcaaccgga tggctgacca agcggcccga aaggcagcca tcacagagac tccagacacc tctaccctcc tcatagaaaa ttcatcaccc tacacctcag aacattttca ttacacagtg actgatataa aggacctaac caagttgggg gccatttatg ataaaacaaa gaagtattgg gtctaccaag gaaaacctgt gatgcctgac cagtttactt ttgaattatt agactttctt catcagctga ctcacctcag cttctcaaaa atgaaggctc tcctagagag aagccacagt ccctactaca tgctgaaccg ggatcgaaca ctcaaaaata tcactgagac ctgcaaagct tgtgcacaag tcaacgccag caagtctgcc gttaaacagg gaactagggt ccgcgggcat cggcccggca ctcattggga gatcgatttc accgagataa agcccggatt gtatggctat aaatatcttc tagtttttat agatacctt tctggctgga tagaagcctt cccaaccaag aaagaaaccg ccaaggtcgt aaccaagaag ctactagagg agatcttccc caggttcggc atgcctcagg tattgggaac tgacaatggg cctgccttcg tctccaaggt gagtcagaca gtggccgatc tgttggggat tgattggaaa ttacattgtg catacagacc ccaaagctca ggccaggtag aaagaatgaa tagaaccatc aaggagactt taactaaatt aacgcttgca actggctcta gagactgggt gctcctactc cccttagccc tgtaccgagc ccgcaacacg ccgggccccc atggcctcac cccatatgag atcttatatg gggcaccccc gccccttgta aacttccctg accctgacat gacaagagtt actaacagcc cctctctcca agtcacttta caggctctct acttagtcca gcacgaagtc tggagacctc tggcggcagc ctaccaagaa caactggacc gaccggtggt acctcaccct taccgagtcg gcgacacagt gtgggtccgc cgacaccaga ctaagaacct agaacctcgc tggaaaggac cttacacagt cctgctgacc accccaccg ccctcaaagt agacggcatc gcagcttgga tacacgccgc ccacgtgaag gctgccgacc ccgggggtgg accatcctct agactgacat ggcgcgttca acgctctcaa aaccccctca agataagatt aacccgtgga agcccttaat agtcatggga gtcctgttag gagtagggat ggcagagagc ccccatcagg tctttaatgt aacctggaga gtcaccaacc tgatgactgg gcgtaccgcc aatgccacct ccctcctggg aactgtacaa gatgccttcc caaaattata ttttgatcta tgtgatctgg tcggagagga gtgggaccct tcagaccagg aaccgtatgt cgggtatggc tgcaagtacc ccgcagggag acagcggacc cggacttttg acttttacgt gtgccctggg cataccgtaa agtcggggtg tggggggacca ggagagggct actgtggtaa atgggggtgt gaaaccaccg gacaggctta ctggaagccc acatcatcgt gggacctaat ctcccttaag cgcggtaaca ccccctggga cacgggatgc tctaaagttg cctgtggccc ctgctacgac ctctccaaag tatccaattc cttccaaggg gctactcgag ggggcagatg caaccctcta gtcctagaat tcactgatgc aggaaaaaag gctaactggg acgggcccaa atcgtgggga ctgagactgt accggacagg aacagatcct attaccatgt tctccctgac ccggcaggtc cttaatgtgg gaccccgagt ccccataggg cccaacccag tattacccga ccaaagactc ccttcctcac caatagagat tgtaccggct ccacagccac ctagccccct caataccagt taccccccctt ccactaccag
```

-continued

```
tacaccctca acctcccta caagtccaag tgtcccacag ccaccccag gaactggaga tagactacta gctctagtca aaggagccta tcaggcgctt aacctcacca atcccgacaa gacccaagaa tgttggctgt gcttagtgtc gggacctcct tattacgaag gagtagcggt cgtgggcact tataccaatc attccaccgc tccggccaac tgtacggcca cttcccaaca taagcttacc ctatctgaag tgacaggaca gggcctatgc atgggggcag tacctaaaac tcaccaggcc ttatgtaaca ccacccaaag cgccggctca ggatcctact accttgcagc acccgccgga acaatgtggg cttgcagcac tggattgact ccctgcttgt ccaccacggt gctcaatcta accacagatt attgtgtatt agttgaactc tggcccagag taatttacca ctcccccgat tatatgtatg gtcagcttga acagcgtacc aaatataaaa gagagccagt atcattgacc ctggcccttc tactaggagg attaaccatg ggagggattg cagctggaat agggacgggg accactgcct taattaaaac ccagcagttt gagcagcttc atgccgctat ccagacagac ctcaacgaag tcgaaaagtc aattaccaac ctagaaaagt cactgacctc gttgtctgaa gtagtcctac agaaccgcag aggcctagat ttgctattcc taaaggaggg aggtctctgc gcagccctaa aagaagaatg ttgtttttat gcagaccaca cggggctagt gagagacagc atggccaaat taagagaaag gcttaatcag agacaaaaac tatttgagac aggccaagga tggttcgaag ggctgtttaa tagatccccc tggtttacca ccttaatctc caccatcatg ggacctctaa tagtactctt actgatctta ctctttggac cttgcattct caatcgatta gtccaatttg ttaaagacag gatatcagtg gtccaggctc tagttttgac tcaacaatat caccagctga agcctataga gtacgagcca tgacgtacgt tactggccga agccgcttgg aataaggccg gtgtgcgttt gtctatatgt tattttccac catattgccg tcttttggca atgtgagggc ccggaaacct ggccctgtct tcttgacgag cattcctagg ggtctttccc ctctcgccaa aggaatgcaa ggtctgttga atgtcgtgaa ggaagcagtt cctctggaag cttcttgaag acaaacaacg tctgtagcga cccttgcag gcagcggaac cccccacctg gcgacaggtg cctctgcggc caaaagccac gtgtataaga tacacctgca aaggcggcac aaccccagtg ccacgttgtg agttggatag ttgtggaaag agtcaaatgg ctctcctcaa gcgtattcaa caaggggctg aaggatgccc agaaggtacc ccattgtatg ggatctgatc tggggcctcg gtgcacatgc tttacatgtg tttagtcgag gttaaaaaaa cgtctaggcc ccccgaacca cggggacgtg gttttccttt gaaaaacacg ataataccat ggtgacaggg ggaatggcaa gcaagtggga tcagaagggt atggacattg cctatgagga ggcggcctta ggttacaaag agggtggtgt tcctattggc ggatgtctta tcaataacaa agacggaagt gttctcggtc gtggtcacaa catgagattt caaaagggat ccgccacact acatggtgag atctccactt tggaaaactg tgggagatta gagggcaaag tgtacaaaga taccactttg tatcgacgc tgtctccatg cgacatgtgt acaggtgcca tcatcatgta tggtattcca cgctgtgttg tcggtgagaa cgttaatttc aaaagtaagg gcgagaaata tttacaaact agaggtcacg aggttgttgt tgttgacgat gagaggtgta aaaagatcat gaaacaattt atcgatgaaa gacctcagga ttggtttgaa gatattggtg agtaggcggc cgcgccatag ataaaataaa agattttatt tagtctccag aaaaagggg gaatgaaaga ccccacctgt aggtttggca agctagctta agtaacgcca ttttgcaagg catgaaaaaa tacataactg agaatagaga agttcagatc aaggtcagga acagatggaa cagctgaata tgggccaaac aggatatctg tggtaagcag ttcctgcccc ggctcagggc caagaacaga tggaacagct gaatatgggc caaacaggat atctgtggta agcagttcct gccccggctc
```

```
agggccaaga acagatggtc cccagatgcg gtccagccct cagcagtttc tagagaacca tcagatgttt ccagggtgcc ccaaggacct gaaatgaccc tgtgccttgt ttaaactaac caatcagttc gcttctcgct tctgttcgcg cgcttctgct ccccgagctc aataaaagag cccacaaccc ctcactcggg gcgccagtcc tccgattgac tgagtcgccc gggtacccgt gtatccaata aaccctcttg cagttgcatc cgacttgtgg tctcgctgtt ccttgggagg gtctcctctg agtgattgac tacccgtcag cgggggtctt tcatttgggg gctcgtccgg gatcgggaga ccctgccca gggaccaccg acccaccacc gggaggtaag ctggctgcct cgcgcgtttc ggtgatgacg gtgaaaacct ctgacatgtg agcaaaaggc cagcaaaagg ccaggaaccg taaaaaggcc gcgttgctgg cgttttccca taggctccgc ccccctgacg agcatcacaa aaatcgacgc tcaagtcaga ggtggcgaaa cccgacagga ctataaagat accaggcgtt tccccctgga agctccctcg tgcgctctcc tgttccgacc ctgccgctta ccggatacct gtccgccttt ctcccttcgg gaagcgtggc gctttctcaa tgctcacgct gtaggtatct cagttcggtg taggtcgttc gctccaagct gggctgtgtg cacgaacccc ccgttcagcc cgaccgctgc gccttatccg gtaactatcg tcttgagtcc aacccggtaa gacacgactt atcgccactg gcagcagcca ctggtaacag gattagcaga gcgaggtatg taggcggtgc tacagagttc ttgaagtggt ggcctaacta cggctacact agaaggacag tatttggtat ctgcgctctg ctgaagccag ttaccttcgg aaaaagagtt ggtagctctt gatccggcaa acaaaccacc gctggtagcg gtggtttttt tgtttgcaag cagcagatta cgcgcagaaa aaaaggatct caagaagatc ctttgatctt ttctacgggg tctgacgctc agtggaacga aaactcacgt taagggattt tggtcatgag attatcaaaa aggatcttca cctagatcct tttaaattaa aaatgaagtt ttaaatcaat ctaaagtata tatgagtaaa cttggtctga cagttaccaa tgcttaatca gtgaggcacc tatctcagcg atctgtctat ttcgttcatc catagttgcc tgactccccg tcgtgtagat aactacgata cgggagggct taccatctgg ccccagtgct gcaatgatac cgcgagaccc acgctcaccg gctccagatt tatcagcaat aaaccagcca gccggaaggg ccgagcgcag aagtggtcct gcaactttat ccgcctccat ccagtctatt aattgttgcc gggaagctag agtaagtagt tcgccagtta atagtttgcg caacgttgtt gccattgctg caggcatcgt ggtgtcacgc tcgtcgtttg gtatggcttc attcagctcc ggttcccaac gatcaaggcg agttacatga tcccccatgt tgtgcaaaaa agcggttagc tccttcggtc ctccgatcgt tgtcagaagt aagttggccg cagtgttatc actcatggtt atggcagcac tgcataattc tcttactgtc atgccatccg taagatgctt ttctgtgact ggtgagtact caaccaagtc attctgagaa tagtgtatgc ggcgaccgag ttgctcttgc ccggcgtcaa cacgggataa taccgcgcca catagcagaa ctttaaaagt gctcatcatt ggaaaacgtt cttcggggcg aaaactctca aggatcttac cgctgttgag atcagttcg atgtaaccca ctcgtgcacc caactgatct tcagcatctt ttactttcac cagcgtttct gggtgagcaa aaacaggaag gcaaaatgcc gcaaaaaagg gaataagggc gacacggaaa tgttgaatac tcatactctt cctttttcaa tattattgaa gcatttatca gggttattgt ctcatgagcg gatacatatt tgaatgtatt tagaaaaata aacaaatagg ggttccgcgc acatttcccc gaaaagtgcc acctgacgtc taagaaacca ttattatcat gacattaacc tataaaaata ggcgtatcac gaggcccttt cgtcttcaag aattcat
```

RCR Vector - pAC3-yCD2

(SEQ ID NO: 25)

```
tagttattaa tagtaatcaa ttacggggtc attagttcat agcccatata tggagttccg
cgttacataa cttacggtaa atggcccgcc tggctgaccg cccaacgacc cccgcccatt
gacgtcaata atgacgtatg ttcccatagt aacgccaata gggactttcc attgacgtca
atgggtggag tatttacggt aaactgccca cttggcagta catcaagtgt atcatatgcc
aagtacgccc cctattgacg tcaatgacgg taaatggccc gcctggcatt atgcccagta
catgacctta tgggactttc ctacttggca gtacatctac gtattagtca tcgctattac
catggtgatg cggttttggc agtacatcaa tgggcgtgga tagcggtttg actcacgggg
atttccaagt ctccacccca ttgacgtcaa tgggagtttg ttttggcacc aaaatcaacg
ggactttcca aaatgtcgta acaactccgc cccattgacg caaatgggcg gtaggcgtgt
acggtgggag gtctatataa gcagagctgg tttagtgaac cggcgccagt cctccgattg
actgagtcgc ccgggtaccc gtgtatccaa taaaccctct tgcagttgca tccgacttgt
ggtctcgctg ttccttggga gggtctcctc tgagtgattg actacccgtc agcggggtc
tttcatttgg ggctcgtcc gggatcggga ccccctgcc cagggaccac cgacccacca
ccgggaggta agctggccag caacttatct gtgtctgtcc gattgtctag tgtctatgac
tgatttatg cgcctgcgtc ggtactagtt agctaactag ctctgtatct ggcggacccg
tggtggaact gacgagttcg gaacacccgg ccgcaaccct gggagacgtc ccagggactt
cggggggccgt ttttgtggcc cgacctgagt ccaaaaatcc cgatcgtttt ggactctttg
gtgcaccccc cttagaggag ggatatgtgg ttctggtagg agacgagaac ctaaaacagt
tcccgcctcc gtctgaattt ttgctttcgg tttgggaccg aagccgcgcc gcgcgtcttg
tctgctgcag catcgttctg tgttgtctct gtctgactgt gtttctgtat ttgtctgaaa
atatgggcca gactgttacc actcccttaa gtttgacctt aggtcactgg aaagatgtcg
agcggatcgc tcacaaccag tcggtagatg tcaagaagag acgttgggtt accttctgct
ctgcagaatg ccaacctttt aacgtcggat ggccgcgaga cggcacctt aaccgagacc
tcatcaccca ggttaagatc aaggtctttt cacctggccc gcatggacac ccagaccagg
tcccctacat cgtgacctgg gaagccttgg cttttgaccc ccctccctgg gtcaagccct
tgtacacccc taagcctccg cctcctcttc ctccatccgc cccgtctctc cccttgaac
ctcctcgttc gaccccgcct cgatcctccc tttatccagc cctcactcct tctctaggcg
ccaaacctaa acctcaagtt ctttctgaca gtggggggcc gctcatcgac ctacttacag
aagaccccc gccttatagg gacccaagac cacccccttc cgacagggac ggaaatggtg
gagaagcgac ccctgcggga gaggcaccgg acccctcccc aatggcatct cgcctacgtg
ggagacggga gccccctgtg gccgactcca ctacctcgca ggcattcccc ctccgcgcag
gaggaaacgg acagcttcaa tactggccgt tctcctcttc tgacctttac aactggaaaa
ataataaccc ttctttttct gaagatccag gtaaactgac agctctgatc gagtctgtcc
tcatcaccca tcagcccacc tgggacgact gtcagcagct gttggggact ctgctgaccg
gagaagaaaa acaacggtg ctcttagagg ctagaaaggc ggtgcgggc gatgatgggc
gccccactca actgcccaat gaagtcgatg ccgcttttcc cctcgagcgc cagactggg
attacaccac ccaggcaggt aggaaccacc tagtccacta cgccagttg ctcctagcgg
gtctccaaaa cgcggggcaga agccccacca atttggccaa ggtaaaagga ataacacaag
ggcccaatga gtcccctcg gccttcctag agagacttaa ggaagcctat cgcaggtaca
ctccttatga ccctgaggac ccagggcaag aaactaatgt gtctatgtct ttcatttggc
```

-continued

```
agtctgcccc agacattggg agaaagttag agaggttaga agatttaaaa aacaagacgc ttggagattt ggttagagag gcagaaaaga tctttaataa acgagaaacc ccggaagaaa gagaggaacg tatcaggaga gaaacagagg aaaaagaaga acgccgtagg acagaggatg agcagaaaga gaaagaaaga gatcgtagga gacatagaga gatgagcaag ctattggcca ctgtcgttag tggacagaaa caggatagac agggaggaga acgaaggagg tcccaactcg atcgcgacca gtgtgcctac tgcaaagaaa aggggcactg ggctaaagat tgtcccaaga aaccacgagg acctcgggga ccaagacccc agacctccct cctgacccta gatgactagg gaggtcaggg tcaggagccc ccccctgaac ccaggataac cctcaaagtc gggggggcaac ccgtcacctt cctggtagat actggggccc aacactccgt gctgacccaa aatcctggac ccctaagtga taagtctgcc tgggtccaag gggctactgg aggaaagcgg tatcgctgga ccacggatcg caaagtacat ctagctaccg gtaaggtcac ccactctttc ctccatgtac cagactgtcc ctatcctctg ttaggaagag atttgctgac taaactaaaa gcccaaatcc actttgaggg atcaggagcc caggttatgg gaccaatggg gcagccctg caagtgttga ccctaaatat agaagatgag tatcggctac atgagacctc aaaagagcca gatgtttctc tagggtccac atggctgtct gattttcctc aggcctgggc ggaaaccggg ggcatgggac tggcagttcg ccaagctcct ctgatcatac ctctgaaagc aacctctacc cccgtgtcca taaaacaata ccccatgtca caagaagcca gactggggat caagcccac atacagagac tgttggacca gggaatactg gtaccctgcc agtccccctg gaacacgccc ctgctacccg ttaagaaacc agggactaat gattataggc ctgtccagga tctgagagaa gtcaacaagc gggtggaaga catccacccc accgtgccca acccttacaa cctcttgagc gggctcccac cgtcccacca gtggtacact gtgcttgatt taaaggatgc ctttttctgc ctgagactcc accccaccag tcagcctctc ttcgcctttg agtggagaga tccagagatg ggaatctcag gacaattgac ctggaccaga ctcccacagg gtttcaaaaa cagtcccacc ctgtttgatg aggcactgca cagagaccta gcagacttcc ggatccagca cccagacttg atcctgctac agtacgtgga tgacttactg ctggccgcca cttctgagct agactgccaa caaggtactc gggccctgtt acaaacccta gggaacctcg ggtatcgggc ctcggccaag aaagcccaaa tttgccagaa acaggtcaag tatctggggt atcttctaaa agagggtcag agatggctga ctgaggccag aaaagagact gtgatggggc agcctactcc gaagacccct cgacaactaa gggagttcct agggacggca ggcttctgtc gcctctggat ccctgggttt gcagaaatgg cagccccctt gtaccctctc accaaaacgg ggactctgtt taattggggc ccagaccaac aaaaggccta tcaagaaatc aagcaagctc ttctaactgc cccagccctg gggttgccag atttgactaa gccctttgaa ctctttgtcg acgagaagca gggctacgcc aaaggtgtcc taacgcaaaa actgggaccrt tggcgtcggc cggtggccta cctgtccaaa aagctagacc cagtagcagc tgggtggccc ccttgcctac ggatggtagc agccattgcc gtactgacaa aggatgcagg caagctaacc atgggacagc cactagtcat tctggccccc catgcagtag aggcactagt caaacaaccc cccgaccgct ggctttccaa cgcccggatg actcactatc aggccttgct tttggacacg gaccgggtcc agttcggacc ggtggtagcc ctgaacccgg ctacgctgct cccactgcct gaggaagggc tgcaacacaa ctgccttgat atcctggccg aagcccacgg aacccgaccc gacctaacgg accagccgct cccagacgcc gaccacacct ggtacacgga tggaagcagt ctcttacaag agggacagcg taaggcggga gctgcggtga ccaccgagac cgaggtaatc tgggctaaag ccctgccagc cgggacatcc gctcagcggg
```

-continued

```
ctgaactgat agcactcacc caggcccotaa agatggcaga aggtaagaag ctaaatgttt atactgatag ccgttatgct tttgctactg cccatatcca tggagaaata tacagaaggc gtgggttgct cacatcagaa ggcaaagaga tcaaaaataa agacgagatc ttggccctac taaaagccct ctttctgccc aaaagactta gcataatcca ttgtccagga catcaaaagg gacacagcgc cgaggctaga ggcaaccgga tggctgacca agcggcccga aaggcagcca tcacagagac tccagacacc tctaccctcc tcatagaaaa ttcatcaccc tacacctcag aacattttca ttacacagtg actgatataa aggacctaac caagttgggg gccatttatg ataaaacaaa gaagtattgg gtctaccaag gaaaacctgt gatgcctgac cagtttactt ttgaattatt agactttctt catcagctga ctcacctcag cttctcaaaa atgaaggctc tcctagagag aagccacagt ccctactaca tgctgaaccg ggatcgaaca ctcaaaaata tcactgagac ctgcaaagct tgtgcacaag tcaacgccag caagtctgcc gttaaacagg gaactagggt ccgcgggcat cggcccggca ctcattggga gatcgatttc accgagataa agcccggatt gtatggctat aaatatcttc tagtttttat agatacctt tctggctgga tagaagcctt cccaaccaag aaagaaaccg ccaaggtcgt aaccaagaag ctactagagg agatcttccc caggttcggc atgcctcagg tattgggaac tgacaatggg cctgccttcg tctccaaggt gagtcagaca gtggccgatc tgttggggat tgattggaaa ttacattgtg catacagacc ccaaagctca ggccaggtag aaagaatgaa tagaaccatc aaggagactt taactaaatt aacgcttgca actggctcta gagactgggt gctcctactc cccttagccc tgtaccgagc ccgcaacacg ccgggccccc atggcctcac cccatatgag atcttatatg gggcaccccc gcccttgta aacttccctg accctgacat gacaagagtt actaacagcc cctctctcca agtcacttta caggctctct acttagtcca gcacgaagtc tggagacctc tggcggcagc ctaccaagaa caactggacc gaccggtggt acctcaccct taccgagtcg gcgacacagt gtgggtccgc cgacaccaga ctaagaacct agaacctcgc tggaaaggac cttacacagt cctgctgacc accccaccg ccctcaaagt agacggcatc gcagcttgga tacacgccgc ccacgtgaag gctgccgacc ccggggtgg accatcctct agactgacat ggcgcgttca acgctctcaa acccccctca agataagatt aacccgtgga agcccttaat agtcatggga gtcctgttag gagtagggat ggcagagagc ccccatcagg tctttaatgt aacctggaga gtcaccaacc tgatgactgg gcgtaccgcc aatgccacct ccctcctggg aactgtacaa gatgccttcc caaaattata ttttgatcta tgtgatctgg tcggagagga gtgggaccct tcagaccagg aaccgtatgt cgggtatggc tgcaagtacc ccgcagggag acagcggacc cggactttg acttttacgt gtgccctggg cataccgtaa agtcggggtg tggggaccca ggagagggct actgtggtaa atgggggtgt gaaaccaccg gacaggctta ctggaagccc acatcatcgt gggacctaat ctcccttaag cgcggtaaca ccccctggga cacgggatgc tctaaagttg cctgtggccc ctgctacgac ctctccaaag tatccaattc cttccaaggg gctactcgag ggggcagatg caaccctcta gtcctagaat tcactgatgc aggaaaaaag gctaactggg acgggcccaa atcgtgggga ctgagactgt accggacagg aacagatcct attaccatgt tctccctgac ccggcaggtc cttaatgtgg gaccccgagt ccccatagqg cccaacccag tattacccga ccaaagactc ccttcctcac caatagagat tgtaccggct ccacagccac ctagcccccct caataccagt tacccccctt ccactaccag tacaccctca acctccccta caagtccaag tgtcccacag ccacccccag gaactggaga tagactacta gctctagtca aaggagccta tcaggcgctt aaccctcacca atcccgacaa
```

-continued

```
gacccaagaa tgttggctgt gcttagtgtc gggacctcct tattacgaag gagtagcggt cgtgggcact tataccaatc attccaccgc tccggccaac tgtacggcca cttcccaaca taagcttacc ctatctgaag tgacaggaca gggcctatgc atgggggcag tacctaaaac tcaccaggcc ttatgtaaca ccacccaaag cgccggctca ggatcctact accttgcagc acccgccgga acaatgtggg cttgcagcac tggattgact ccctgcttgt ccaccacggt gctcaatcta accacagatt attgtgtatt agttgaactc tggcccagag taatttacca ctcccccgat tatatgtatg gtcagcttga acagcgtacc aaatataaaa gagagccagt atcattgacc ctggcccttc tactaggagg attaaccatg ggagggattg cagctggaat agggacgggg accactgcct taattaaaac ccagcagttt gagcagcttc atgccgctat ccagacagac ctcaacgaag tcgaaaagtc aattaccaac ctagaaaagt cactgacctc gttgtctgaa gtagtcctac agaaccgcag aggcctagat ttgctattcc taaaggaggg aggtctctgc gcagccctaa agaagaatg ttgtttttat gcagaccaca cggggctagt gagagacagc atggccaaat taagagaaag gcttaatcag agacaaaaac tatttgagac aggccaagga tggttcgaag ggctgtttaa tagatccccc tggtttacca ccttaatctc caccatcatg ggacctctaa tagtactctt actgatctta ctctttggac cttgcattct caatcgattg gtccaatttg ttaaagacag gatctcagtg gtccaggctc tggttttgac tcagcaatat caccagctaa aacccataga gtacgagcca tgaacgcgtt actggccgaa gccgcttgga ataaggccgg tgtgcgtttg tctatatgtt attttccacc atattgccgt cttttggcaa tgtgagggcc cggaaacctg gccctgtctt cttgacgagc attcctaggg gtctttcccc tctcgccaaa ggaatgcaag gtctgttgaa tgtcgtgaag gaagcagttc ctctggaagc ttcttgaaga caaacaacgt ctgtagcgac cctttgcagg cagcggaacc ccccacctgg cgacaggtgc ctctgcggcc aaaagccacg tgtataagat acacctgcaa aggcggcaca accccagtgc cacgttgtga gttggatagt tgtggaaaga gtcaaatggc tctcctcaag cgtattcaac aagggggctga aggatgccca gaaggtaccc cattgtatgg gatctgatct ggggcctcgg tgcacatgct ttacatgtgt ttagtcgagg ttaaaaaaac gtctaggccc cccgaaccac ggggacgtgg ttttcctttg aaaaacacga ttataaatgg tgaccggcgg catggcctcc aagtgggatc aaaagggcat ggatatcgct tacgaggagg ccctgctggg ctacaaggag ggcggcgtgc ctatcggcgg ctgtctgatc aacaacaagg acggcagtgt gctgggcagg ggccacaaca tgaggttcca gaagggctcc gccaccctgc acggcgagat ctccaccctg gagaactgtg gcaggctgga gggcaaggtg tacaaggaca ccaccctgta caccaccctg tcccttgtg acatgtgtac cggcgctatc atcatgtacg gcatccctag gtgtgtgatc ggcgagaacg tgaacttcaa gtccaagggc gagaagtacc tgcaaaccag gggccacgag gtggtggttg ttgacgatga gaggtgtaag aagctgatga agcagttcat cgacgagagg cctcaggact ggttcgagga tatcggcgag taagcggccg cagataaaat aaaagatttt atttagtctc cagaaaaagg ggggaatgaa agaccccacc tgtaggtttg gcaagctagc ttaagtaacg ccatttgca aggcatggaa aaatacataa ctgagaatag agaagttcag atcaaggtca ggaacagatg gaacagctga atatgggcca aacaggatat ctgtggtaag cagttcctgc cccggctcag ggccaagaac agatggaaca gctgaatatg gccaaacag gatatctgtg gtaagcagtt cctgccccgg ctcagggcca agaacagatg gtccccagat gcggtccagc cctcagcagt ttctagagaa ccatcagatg tttccagggt gccccaagga cctgaaatga ccctgtgcct tatttgaact aaccaatcag
```

-continued

```
ttcgcttctc gcttctgttc gcgcgcttct gctccccgag ctcaataaaa gagcccacaa cccctcactc ggggcgccag tcctccgatt gactgagtcg cccgggtacc cgtgtatcca ataaaccctc ttgcagttgc atccgacttg tggtctcgct gttccttggg agggtctcct ctgagtgatt gactacccgt cagcgggggt ctttcattac atgtgagcaa aaggccagca aaaggccagg aaccgtaaaa aggccgcgtt gctggcgttt ttccataggc tccgcccccc tgacgagcat cacaaaaatc gacgctcaag tcagaggtgg cgaaacccga caggactata aagataccag gcgtttcccc ctggaagctc cctcgtgcgc tctcctgttc cgaccctgcc gcttaccgga tacctgtccg cctttctccc ttcgggaagc gtggcgcttt ctcatagctc acgctgtagg tatctcagtt cggtgtaggt cgttcgctcc aagctgggct gtgtgcacga accccccgtt cagcccgacc gctgcgcctt atccggtaac tatcgtcttg agtccaaccc ggtaagacac gacttatcgc cactggcagc agccactggt aacaggatta gcagagcgag gtatgtaggc ggtgctacag agttcttgaa gtggtggcct aactacggct acactagaag gacagtattt ggtatctgcg ctctgctgaa gccagttacc ttcggaaaaa gagttggtag ctcttgatcc ggcaaacaaa ccaccgctgg tagcggtggt ttttttgttt gcaagcagca gattacgcgc agaaaaaaag gatctcaaga agatcctttg atcttttcta cggggtctga cgctcagtgg aacgaaaact cacgttaagg gattttggtc atgagattat caaaaaggat cttcacctag atcctttaa attaaaaatg aagtttaaa tcaatctaaa gtatatatga gtaaacttgg tctgacagtt accaatgctt aatcagtgag gcacctatct cagcgatctg tctatttcgt tcatccatag ttgcctgact cccgtcgtg tagataacta cgatacggga gggcttacca tctggcccca gtgctgcaat gataccgcga gacccacgct caccggctcc agatttatca gcaataaacc agccagccgg aagggccgag cgcagaagtg gtcctgcaac tttatccgcc tccatccagt ctattaattg ttgccgggaa gctagagtaa gtagttcgcc agttaatagt ttgcgcaacg ttgttgccat tgctgcaggc atcgtggtgt cacgctcgtc gtttggtatg gcttcattca gctccggttc ccaacgatca aggcgagtta catgatcccc catgttgtgc aaaaaagcgg ttagctcctt cggtcctccg atcgttgtca gaagtaagtt ggccgcagtg ttatcactca tggttatggc agcactgcat aattctctta ctgtcatgcc atccgtaaga tgcttttctg tgactggtga gtactcaacc aagtcattct gagaatagtg tatgcggcga ccgagttgct cttgcccggc gtcaacacgg gataataccg cgccacatag cagaacttta aaagtgctca tcattggaaa acgttcttcg gggcgaaaac tctcaaggat cttaccgctg ttgagatcca gttcgatgta acccactcgt gcacccaact gatcttcagc atctttact ttcaccagcg tttctgggtg agcaaaaaca ggaaggcaaa atgccgcaaa aaagggaata agggcgacac ggaaatgttg aatactcata ctcttccttt ttcaatatta ttgaagcatt tatcagggtt attgtctcat gagcggatac atatttgaat gtatttagaa aaataaacaa atagggttc cgcgcacatt tccccgaaaa gtgccacctg acgtctaaga aaccattatt atcatgacat taacctataa aaataggcgt atcacgaggc cctttcgtct tcaagaattc cat
```

Disclosed herein are assays for detection of target molecules, such as target nucleic acids comprising viral RNA or DNA, using a plurality of nucleic acid amplification techniques including, for example: NAAT (J. D. Fox, J. Clin. Virol. 40 Suppl. 1 S15-S23, 2007), PCR, RT-PCR, qPCR and RT-qPCR with "touchdown" modifications to improve sensitivity to single copy/assay; RNA transcription based assays (e.g. analogous to the HIV-1 Aptiva assay, see http://www.fda.gov/BiologicsBloodVaccines/BloodBlood-Products/ApprovedProducts/LicensedProductsBLAs/BloodDonorScreening/InfectiousDisease/ucm149922.htm); the "branched DNA" system (see, e.g., Anastassopoulou et al., Journal of Virological Methods, 91:67-74, 2001); and further variations in NAAT known to those of skill in the art.

Also disclosed are methods using NAAT on nucleic acid samples extracted from histologically fixed samples.

The assays provided by the disclosure may be used in many embodiments to detect sequence-specific nucleic acids. Disclosed herein are different embodiments of assays using amplification (e.g., PCR) and enzymatic degradation of RNA/DNA heteroduplexes.

Generally, the disclosure provides a method of identifying MLV-related viral polynucleotides in a subject or sample. The disclosure utilizes a combination of primers and probes having identity to conserved regions of MLV-related viruses. The primers are used to amplify target polynucleotides in the sample and probes are then used to visualize or detect the amplified products. Typically the probe is detectably labeled for detection (e.g., fluorescently labeled, luminescently labeled, enzyme conjugated, radionucleotide labeled and the like). One advantage of the disclosure is that the primer pairs can be used to amplify MLV-related polynucleotides in a sample such as MLV, XMRV or MLV and XMRV polynucleotides. This is advantageous for the detection of XMRV and naturally occurring variants thereof as well as for detecting MLV and naturally occurring variants thereof (including recombinantly engineered MLV vectors).

For example, a combination of primers and probes identified herein can be used to identify or detect XMRV in a sample, tissue or subject by using primer pairs having homology to MLV (e.g., primer pairs that share at least 95% sequence identity between and XMRV viral sequence and an MLV viral sequence) and a probe sequence that is specific for XMRV (e.g., the probe only hybridizes to an amplified product under highly stringent conditions). Primers that share such homology between XMRV and MLV are identified in FIG. 5.

One utility of this general method is to screen blood and tissue supplies for infection. XMRV has been suggested to be associated with prostate cancer and chronic fatigue syndrome. In another utility, a subject may be screened prior to undergoing treatment with a recombinant retroviral vector. By identifying subject that may have circulating viral polynucleotides in the tissue a risk of recombination between the inherent viral polynucleotide and the therapeutic viral polynucleotide may be managed.

In another general example, a combination of primers and probes identified herein can be used to identify or detect MLV or MLV-related polynucleotides in a sample, tissue or subject by using primer pairs having homology to MLV (e.g., primer pairs that share at least 95% sequence identity between and XMRV viral sequence and an MLV viral sequence) and a probe sequence that is specific for MLV (e.g., the probe only hybridizes to an amplified product under highly stringent conditions).

In another embodiment of the general methods described herein, the methods provide useful diagnostics for monitoring patients after delivery of a replication competent MLV-related viral vector. The method can be used to monitor a subject following delivery of the vector on a routine basis (e.g., weekly, monthly, yearly) for as long as a treating physician deems necessary.

As used herein "MLV-related virus" refers to a retrovirus comprising the general structure of an MLV virus (e.g., LTR-gag-pol-env-LTR) and having at least 60% identity to any of the following sequences set forth in the identified accession numbers (which are incorporated herein by reference in their entirety): Xenotropic murine leukemia virus isolate LAPC4, complete genome (8,657 bp linear DNA, JF908816.1 GI:336462519); Xenotropic murine leukemia virus isolate VCaP, complete genome (8,657 bp linear DNA, JF908815.1 GI:336462515); Murine leukemia virus N417, complete genome (8,189 bp linear RNA, HQ246218.1 GI:313762331); Moloney murine leukemia virus neuropathogenic variant ts1-92b, complete genome (8,332 bp linear DNA, AF462057.1 GI: 18448741); DG-75 Murine leukemia virus, complete genome (8,207 bp linear RNA, AF221065.1 GI: 11078528); Rauscher murine leukemia virus, complete genome (8,282 bp linear DNA, NC_001819.1 GI:9629514); Murine leukemia virus SL3-3, complete genome (8,377 bp linear RNA, AF169256.1 GI:5881088); Murine leukemia virus strain SRS 19-6 complete genome (8,256 bp linear DNA, AF019230.1 GI:4071074); Mus dunni endogenous virus complete genome (8,655 bp linear DNA, AF053745.1 GI:3309122); Moloney murine leukemia virus, complete genome (8,332 bp linear RNA, AF033811.1 GI:2801468); Murine type C retrovirus, complete genome (8,135 bp linear DNA, NC_001702.1 GI:9628654); Rauscher murine leukemia virus, complete genome (8,282 bp linear DNA, U94692.1 GI:2228757); Murine leukemia virus isolate NeRV, complete genome (8,273 bp linear RNA, DQ366149.1 GI:86651892); Murine leukemia virus serotype HEMV provirus, complete genome (8,546 bp linear DNA, AY818896.1 GI:55979252); Murine leukemia virus strain BM5eco, complete genome (8,281 bp linear DNA, AY252102.1 GI:30908470); Murine leukemia virus MCF1233, complete genome (8,196 bp linear DNA, U13766.1 GI:535516); MuLV (strain RadLV/VL3(T+L+)) RNA, complete genome (8,394 bp linear RNA, K03363.1 GI:332032); Mink cell focus-forming 247 MuLV env gene, 3' end and LTR (1,164 bp linear RNA, J02249.1 GI:332023); Friend murine leukemia virus, complete genome (8,282 bp linear RNA, M93134.1 GI:331898); Friend murine leukemia virus, complete genome (8,323 bp linear RNA, NC_001362.1 GI:9626096); Friend murine leukemia virus (F-MuLV) complete RNA genome (8,359 bp linear RNA, X02794.1 GI:61544); *Gallus gallus* MLV-related endogenous retrovirus, complete genome (9,133 bp linear DNA, DQ280312.2 GI:169805278); Friend murine leukemia virus genomic RNA, complete genome, clone:A8 (8,358 bp linear RNA, D88386.1 GI:2351211); PreXMRV-1 provirus, complete genome (8,197 bp linear DNA; NC_007815.2 GI:339276104); Xenotropic MuLV-related virus RKO, complete genome (8,172 bp linear DNA, JF274252.1 GI:338191621); XMRV complete proviral genome, isolate S-162 (8,562 bp linear DNA, FR872816.1 GI:336087897); PreXMRV-2 complete proviral genome (8,193 bp linear DNA, FR871850.1 GI:334849718); Xenotropic MuLV-related virus 22Rv1/CWR-R1 complete proviral genome (8,185 bp linear DNA, FN692043.2 GI:334717372); Xenotropic MuLV-related virus isolate xmlvl5, complete genome (8,176 bp linear RNA, HQ154630.1 GI:320091412); PreXMRV-1 complete proviral genome (8,197 bp linear DNA, FR871849.1 GI:334849715); Xenotropic MuLV-related virus VP62, complete genome (8,185 bp linear RNA, DQ399707.1 GI:88765817); Xenotropic MuLV-related virus VP42, complete genome (8,185 bp linear RNA, DQ241302.1 GI:82582299); Xenotropic MuLV-related virus VP35, complete genome (8,185 bp linear RNA, DQ241301.1 GI:82582295); Xenotropic MuLV-related virus VP62, complete genome (8,165 bp linear RNA, EF185282.1 GI: 121104176); Plasmid pAMS with hybrid amphotropic/Moloney murine leukemia virus, complete sequence (11,328 bp circular DNA, AF010170.1 GI:2281586); Amphotropic murine leukemia virus strain 1313, complete genome (8,217 bp linear DNA, AF411814.1

GI:28892668); Toca511, recombinant replication competent MLV comprising a polynucleotide encoding cytosine deaminase (see, e.g., SEQ ID NO:19, 20 and 22 of PCT/US2009/058512, incorporated herein by reference).

Any number of different alignment programs can be used to identified regions of identity between any combination of the foregoing MLV-related genomes. Other genomes will be readily identified by using a BLAST algorithm or other similar algorithm to identify sequences having homology/identity to the foregoing sequences.

In some embodiments the disclosure relates to a method of detecting MLV-related viruses including XMRV in a sample comprising contacting the sample with a nucleic acid sequence that hybridizes to all or a portion of XMRV nucleic acid sequence under conditions in which a hybridization complex can occur between the detecting nucleic acid sequence and the XMRV nucleic acid sequence. In a related embodiment, the XMRV specific primers are 95% or more identical to SEQ ID Nos:1 and 2, and the probe is 95% or more identical to SEQ ID NO:3 (XMRV gag). In a further related embodiment the XMRV specific primers are 95% or more identical to SEQ ID NOs:4 and 5 and the probe is 95% or more identical to SEQ ID NO:6 (XMRV env). In yet a further embodiment, the method uses a combination of primers and probes (e.g., SEQ ID NO:1, 2, 4 and 5 and probes comprising SEQ ID NO:3 and 6).

In another embodiment, the disclosure relates to a method of detecting XMRV or other MLV related nucleic acids in a sample by using primers and probes that are not specific to XMRV but rather are shared between XMRV and other related strains of MLV. In a related embodiment the MLV/XMRV specific primers are SEQ ID NOs:7 and 8 and the probe is SEQ ID NO:9 (Pol 2 primers and probe; other primers and probes are set forth in Table 1 below). In a further related embodiment, the MLV/XMRV specific primers are SEQ ID NOs: 10 and 11 and the probe is SEQ ID NO: 12 (pol1 primer and probe). In a further related embodiment, other sequences can be identified that are common to XMRV and MLV (see the BLAST sequence comparison of two genomes of XMRV and MLV, FIG. 5, where perfect sequence homologies of 20 or more bases are underlined/highlighted). Such homologous sequences (or shorter runs of homology down to 15 bases) can be used to select primers and probes. Alternatively, primers and probes can be chosen using programs that compare sequences and suggest common primers and probes. Such programs are usually designed to look for related genes in different species, and can be used to design QPCR reagents for molecules such as MLV and XMRV with significant but incomplete homology. An example of such a program is Primaclade http:(//)www.umsl.edu/services/kellogg/primaclade/FAQ.html.

An oligonucleotide probe or a primer refers to a nucleic acid molecule of between 8 and 2000 nucleotides in length, or is specified to be about 6 and 1000 nucleotides in length. More particularly, the length of these oligonucleotides can range from about 8, 10, 15, 20, or 30 to 100 nucleotides, but will typically be about 10 to 50 (e.g., 15 to 30 nucleotides). The appropriate length for oligonucleotides in assays of the disclosure under a particular set of conditions may be empirically determined by one of skill in the art. As used herein a primer or probe consisting of at least 95% identity to a reference sequence means that the sequence comprises a sequence that is the same number of oligonucleotides in length, but may differ in nucleotides by 5% from the reference sequence. In addition, a primer or probe consisting of at least 95% identity to a reference sequence and having from 1-10 additional or deleted nucleotides at the 5' and/or 3' end of the oligonucleotide means that the sequence differs by 1 to up to 20 nucleotides in length from the reference sequence and which also differs 5% or less in identity. Accordingly, any primer probe disclosed herein by consist of a reference sequence (e.g., SEQ ID NO:1-21 or sequences set forth in Table 1); can consist of a sequence that is 95% of greater in identity to a reference sequence (e.g., SEQ ID NO:1-21 or sequences set forth in Table 1); or can consist of a sequence that is at least 95% identical and has an additional 1-20 (e.g., 1, 2, 3, 4, 5, 6, 7, 8, 9 or 10 nucleotides at the 5' and/or 3' end of the reference sequence (e.g., SEQ ID NO: 1-21 or sequence set forth in Table 1).

Oligonucleotide primers and probes can be prepared by any suitable method, including direct chemical synthesis and a number of probe systems with derivatized oligonucleotides are available to hybridize to and to detect amplified product, normally by fluorescence change on binding to the probe target. The oligonucleotide primers and probes can contain conventional nucleotides, as well as any of a variety of analogs. For example, the term "nucleotide", as used herein, refers to a compound comprising a nucleotide base linked to the C-1' carbon of a sugar, such as ribose, arabinose, xylose, and pyranose, and sugar analogs thereof. The term nucleotide also encompasses nucleotide analogs. The sugar may be substituted or unsubstituted. Substituted ribose sugars include, but are not limited to, those riboses in which one or more of the carbon atoms, for example the 2'-carbon atom, is substituted with one or more of the same or different Cl, F, —R, —OR, —NR$_2$ or halogen groups, where each R is independently H, $C_1$-$C_6$ alkyl or $C_5$-$C_{14}$ aryl. Exemplary riboses include, but are not limited to, 2'-($C_1$-$C_6$)alkoxyribose, 2'-($C_5$-$C_{14}$)aryloxyribose, 2',3'-didehydroribose, 2'-deoxy-3'-haloribose, 2'-deoxy-3'-fluororibose, 2'-deoxy-3'-chlororibose, 2'-deoxy-3'-aminoribose, 2'-deoxy-3'-($C_1$-$C_6$) alkylribose, 2'-deoxy-3'-($C_1$-$C_6$)alkoxyribose and 2'-deoxy-3'-($C_5$-$C_{14}$)aryloxyribose, ribose, 2'-deoxyribose, 2',3'-dideoxyribose, 2'-haloribose, 2'-fluororibose, 2'-chlororibose, and 2'-alkylribose, e.g., 2'-O-methyl, 4'-α-anomeric nucleotides, 1'-α-anomeric nucleotides, 2'-4'- and 3'-4'-linked and other "locked" or "LNA", bicyclic sugar modifications (see, e.g., PCT published application nos. WO 98/22489, WO 98/39352; and WO 99/14226).

Modifications at the 2'- or 3'-position of ribose include, but are not limited to, hydrogen, hydroxy, methoxy, ethoxy, allyloxy, isopropoxy, butoxy, isobutoxy, methoxyethyl, alkoxy, phenoxy, azido, amino, alkylamino, fluoro, chloro and bromo. Nucleotides include, but are not limited to, the natural D optical isomer, as well as the L optical isomer forms (see, e.g., Garbesi (1993) Nucl. Acids Res. 21:4159-65; Fujimori (1990) J. Amer. Chem. Soc. 112:7435; Urata, (1993) Nucleic Acids Symposium Ser. No. 29:69-70). When the nucleotide base is purine, e.g. A or G, the ribose sugar is attached to the N9-position of the nucleotide base. When the nucleotide base is pyrimidine, e.g. C, T or U, the pentose sugar is attached to the Ni-position of the nucleotide base, except for pseudouridines, in which the pentose sugar is attached to the $C_5$ position of the uracil nucleotide base (see, e.g., Kornberg and Baker, (1992) DNA Replication, 2nd Ed., Freeman, San Francisco, Calif.). The 3' end of the probe can be functionalized with a capture or detectable label to assist in detection of a target polynucleotide or of a polymorphism.

Any of the oligonucleotides or nucleic acids of the disclosure can be labeled by incorporating a detectable label measurable by spectroscopic, photochemical, biochemical, immunochemical, or chemical means. For example, such labels can comprise radioactive substances (e.g., $^{32}$P, $^{35}$S, $^3$H, $^{125}$I), fluorescent dyes (e.g., 5-bromodesoxyuridin, fluorescein, acetylaminofluorene, digoxigenin), molecular quenchers (e.g. blackhole, molecular beacons), biotin, nanoparticles, and others know to those skilled in the art. Such oligonucleotides are typically labeled at their 3' and/or 5' ends.

A probe refers to a molecule which can detectably distinguish changes in gene expression or can distinguish between target molecules differing in structure. Detection can be accomplished in a variety of different ways depending on the type of probe used and the type of target molecule. Thus, for example, detection may be based on discrimination of activity levels of the target molecule, but typically is based on detection of specific binding. Examples of such specific binding include nucleic acid probe hybridization. Thus, for example, probes can include nucleic acid hybridization probes (including primers useful for polynucleotide amplification and/or detection). Thus, in one embodiment, the detection of the presence or absence of the at least one target polynucleotide involves contacting a biological sample with a probe or primer pair. Typically an oligonucleotide probe or primer pair, where the probe/primers hybridizes with a form of a target polynucleotide in the biological sample containing a complementary sequence, undergoes hybridization using hybridization selective conditions. Such an oligonucleotide probe can include one or more nucleic acid analogs, labels or other substituents or moieties so long as the base-pairing function is retained.

The disclosure provides methods and systems for identifying and quantifying the amount of a given nucleic acid sequence in a given sample, usually down to a single copy per sample. Furthermore, the methods and systems of the disclosure provide sequence specific detection useful for differentiating/identifying related genomic sequences and provide a detectable signal when the correct target sequence is present. The disclosure provides various embodiments of the invention.

Methods known in the art can be used to quantitatively measure the amount of a nucleic acid present in a sample. Examples of such methods include quantitative polymerase chain reaction (qPCR), and other NAAT technologies as described above.

In one embodiment, a method for detecting a specific viral polynucleotide is provided by the disclosure. Such a method can include the use of primers, probes, enzymes, and other reagents for the preparation, detection, and quantitation of a viral polynucleotide (e.g., by PCR, by Northern blot and the like). The primers listed in SEQ ID NOs: 1-12 are particularly suited for use in profiling using RT-PCR based on a viral polynucleotide. Although the disclosure provides particular primers and probes, those of skill in the art will readily recognize that additional probes and primers can be generated based upon the polynucleotide sequences provided by the disclosure (see, also, for example, FIG. 5). Referring to the primers and probes exemplified herein, a series of primers were designed to amplify portions of a murine retroviral (MLV) genome. The primer/probe sets listed in SEQ ID NOs: 1-12 were designed, selected, and tested accordingly (see Examples). Though a number of detection schemes for detecting amplicons are contemplated, as will be discussed in more detail below, one method for detection of polynucleotide amplicons is fluorescence spectroscopy, and therefore labels suited to fluorescence spectroscopy are desirable for detecting polynucleotide. In a related form of detection the amplicon polynucleotide is detected without a hybridization probe but directly with a fluorophore that binds DNA and fluoresces at a wavelength different from that of the free reagent. An example of such a fluorescent label is SYBR Green, though numerous related fluorescent molecules are known including, without limitation, DAPI, Cy3, Cy3.5, Cy5, CyS.5, Cy7, umbelliferone, fluorescein, fluorescein isothiocyanate (FITC), rhodamine, dichlorotriazinylamine fluorescein, dansyl chloride or phycoerythrin.

In one embodiment of the disclosure, an oligonucleotide primer pair is used to amplify a polynucleotide corresponding to the pol gene of a murine retrovirus. Primers comprising SEQ ID NOs:7 and 8 (forward and reverse primers, respectively) are used to amplify the region of the pol gene. The amplified region can then be detected using a probe (SEQ ID NO:9), which specifically hybridizes to the amplified polynucleotide. The probe can be labeled with any number of detectable labels as described herein.

The foregoing primers (SEQ ID NOs:7, 8 and 10, 11) with the appropriate probes (SEQ ID NOs:9 and 12, respectively) can be used to detect the presence of, for example, Murine Leukemia Virus (MLV) and Xenotropic Murine Retrovirus (XMRV). As described elsewhere herein identifying the presence of MLV and/or XMRV is useful for the determination of a therapeutic gene delivery and cancer treatment regimen.

In another embodiment of the disclosure, an oligonucleotide primer pair is used to amplify a polynucleotide corresponding to the gag gene of a XMRV. Primers comprising SEQ ID NOs: 1 and 2 (forward and reverse primers, respectively) are used to amplify the region of the gag gene of XMRV. The amplified region can then be detected using a probe (SEQ ID NO:3) which specifically hybridizes to the amplified polynucleotide. The probe can be labeled with any number of detectable labels as described herein. This combination of primers and probes is useful for specifically identifying the presence of an XMRV infection or contamination.

In another embodiment of the disclosure, an oligonucleotide primer pair is used to amplify a polynucleotide corresponding to the LTR of an MLV vector. Primers comprising SEQ ID NOs: 16 and 17 (forward and reverse primers, respectively) are used to amplify the region of the LTR of an MLV vector (e.g., Toca511). The amplified region can then be detected using a probe (SEQ ID NO: 18) which specifically hybridizes to the amplified polynucleotide. The probe can be labeled with any number of detectable labels as described herein. This combination of primers and probes is useful for specifically identifying the presence of a retroviral vector during gene delivery monitoring.

In another embodiment of the disclosure, an oligonucleotide primer pair is used to amplify a polynucleotide corresponding to a polynucleotide encoding a cytosine deaminase. Primers comprising SEQ ID NOs: 19 and 20 (forward and reverse primers, respectively) are used to amplify the region of the a cytosine deaminase delivered using an MLV vector (e.g., Toca511). The amplified region can then be detected using a probe (SEQ ID NO:21) which specifically hybridizes to the amplified polynucleotide. The probe can be labeled with any number of detectable labels as described herein. This combination of primers and probes is useful for specifically identifying the presence of a retroviral vector during gene delivery monitoring.

The primers (SEQ ID NOs: 1 and 2) and probe (SEQ ID NO:3) can be used to detect the presence of XMRV. As described elsewhere herein identifying the presence of XMRV is useful for the determination of a therapeutic gene delivery, cancer treatment regimen and blood supply screening.

In another embodiment of the disclosure, an oligonucleotide primer pair is used to amplify a polynucleotide corresponding to the env gene of a XMRV. Primers comprising SEQ ID NOs:4 and 5 (forward and reverse primers, respectively) are used to amplify the region of the env gene of XMRV. The amplified region can then be detected using a probe (SEQ ID NO:6) which specifically hybridizes to the amplified polynucleotide. The probe can be labeled with any number of detectable labels as described herein. This combination of primers and probes is useful for specifically identifying the presence of an XMRV infection or contamination.

The foregoing primers (SEQ ID NOs:4 and 5) and probe (SEQ ID NO:6) can be used to detect the presence of XMRV. As described elsewhere herein identifying the presence of XMRV is useful for the determination of a therapeutic gene delivery, cancer treatment regimen and screening the blood supply.

Any of the oligonucleotide primers and probes of the disclosure can be immobilized on a solid support. Solid supports are known to those skilled in the art and include the walls of wells of a reaction tray, test tubes, polystyrene beads, magnetic beads, nitrocellulose strips, membranes, microparticles such as latex particles, glass and the like. The solid support is not critical and can be selected by one skilled in the art. Thus, latex particles, microparticles, magnetic or non-magnetic beads, membranes, plastic tubes, walls of microtiter wells, glass or silicon chips and the like are all suitable examples. Suitable methods for immobilizing oligonucleotides on a solid phase include ionic, hydrophobic, covalent interactions and the like. The solid support can be chosen for its intrinsic ability to attract and immobilize the capture reagent. The oligonucleotide probes or primers of the disclosure can be attached to or immobilized on a solid support individually or in groups of about 2-10,000 distinct oligonucleotides of the disclosure to a single solid support.

A substrate comprising a plurality of oligonucleotide primers or probes of the disclosure may be used either for detecting or amplifying targeted sequences. The oligonucleotide probes and primers of the disclosure can be attached in contiguous regions or at random locations on the solid support. Alternatively the oligonucleotides of the disclosure may be attached in an ordered array wherein each oligonucleotide is attached to a distinct region of the solid support which does not overlap with the attachment site of any other oligonucleotide. Typically, such oligonucleotide arrays are "addressable" such that distinct locations are recorded and can be accessed as part of an assay procedure. The knowledge of the location of oligonucleotides on an array make "addressable" arrays useful in hybridization assays. For example, the oligonucleotide probes can be used in an oligonucleotide chip such as those marketed by Affymetrix and described in U.S. Pat. No. 5,143,854; PCT publications WO 90/15070 and 92/10092, the disclosures of which are incorporated herein by reference. These arrays can be produced using mechanical synthesis methods or light directed synthesis methods which incorporate a combination of photolithographic methods and solid phase oligonucleotide synthesis.

The immobilization of arrays of oligonucleotides on solid supports has been rendered possible by the development of a technology generally referred to as "Very Large Scale Immobilized Polymer Synthesis" in which probes are immobilized in a high density array on a solid surface of a chip (see, e.g., U.S. Pat. Nos. 5,143,854; and 5,412,087 and in PCT Publications WO 90/15070, WO 92/10092 and WO 95/11995, each of which are incorporated herein by reference), which describe methods for forming oligonucleotide arrays through techniques such as light-directed synthesis techniques.

In another embodiment, an array of oligonucleotides complementary to subsequences of the target gene (for example yeast cytosine deaminase (CD) or a version of CD optimized for expression in human cells) is used to determine the identity of the target, measure its amount and the like.

Hybridization techniques can also be used to identify the viral polynucleotides in a subject or sample and thereby determine or predict cross reactivity, chances of recombination or a treatment regimen using a gene delivery vector comprising a recombinant MLV vector. The hybridization reactions may be carried out in a solid support (e.g., membrane or chip) format, in which, for example, a probe (e.g., SEQ ID NO:3, 6 and/or 9) are immobilized on nitrocellulose or nylon membranes and probed with amplified preparations of nucleic acids obtained, for example, from PCR using primers comprising SEQ ID NO: 1, 2, 4, 5, 7, 8, 10, 11, 13 and/or 14 of the disclosure. Any of the known hybridization formats may be used, including Southern blots, slot blots, "reverse" dot blots, solution hybridization, solid support based sandwich hybridization, bead-based, silicon chip-based and microtiter well-based hybridization formats.

Hybridization of an oligonucleotide probe to a target polynucleotide may be performed with both entities in solution, or such hybridization may be performed when either the oligonucleotide or the target polynucleotide is covalently or noncovalently affixed to a solid support. Attachment to a solid support may be mediated, for example, by antibody-antigen interactions, poly-L-Lysine, streptavidin or avidin-biotin, salt bridges, hydrophobic interactions, chemical linkages, UV cross-linking baking, etc. Oligonucleotides may be synthesized directly on the solid support or attached to the solid support subsequent to synthesis. The solid support may be treated, coated or derivatized to facilitate the immobilization of the specific oligonucleotide.

Hybridization assays based on oligonucleotide arrays rely on the differences in hybridization stability of short oligonucleotides to perfectly matched and mismatched target variants. Each DNA chip can contain thousands to millions of individual synthetic DNA probes arranged in a grid-like pattern and miniaturized to the size of a dime or smaller. Such a chip may comprise oligonucleotides representative of both a wild-type and variant sequences.

Oligonucleotides of the disclosure can be designed to specifically hybridize to a target region of a polynucleotide. As used herein, specific hybridization means the oligonucleotide forms an anti-parallel double-stranded structure with the target region under certain hybridizing conditions, while failing to form such a structure when incubated with a different target polynucleotide or another region in the polynucleotide or with a polynucleotide lacking the desired locus under the same hybridizing conditions. Typically, the oligonucleotide specifically hybridizes to the target region under conventional high stringency conditions.

A nucleic acid molecule such as an oligonucleotide or polynucleotide is said to be a "perfect" or "complete" complement of another nucleic acid molecule if every nucleotide of one of the molecules is complementary to the nucleotide at the corresponding position of the other molecule. A nucleic acid molecule is "substantially complementary" to another molecule if it hybridizes to that molecule with sufficient stability to remain in a duplex form under conventional low-stringency conditions. Conventional hybridization conditions are described, for example, in Sambrook et al., Molecular Cloning, A Laboratory Manual, 2nd ed., Cold Spring Harbor Press, Cold Spring Harbor, N.Y. (1989), and in Haymes et al., Nucleic Acid Hybridization, A Practical Approach, IRL Press, Washington, D.C. (1985). While perfectly complementary oligonucleotides are used in most assays for detecting target polynucleotides or polymorphisms, departures from complete complementarity are contemplated where such departures do not prevent the molecule from specifically hybridizing to the target region. For example, an oligonucleotide primer may have a non-complementary fragment at its 5' or 3' end, with the remainder of the primer being complementary to the target region. Those of skill in the art are familiar with parameters that affect hybridization; such as temperature, probe or primer length and composition, buffer composition and salt concentration and can readily adjust these parameters to achieve specific hybridization of a nucleic acid to a target sequence.

A variety of hybridization conditions may be used in the disclosure, including high, moderate and low stringency conditions; see for example Maniatis et al., Molecular Cloning: A Laboratory Manual, 2d Edition, 1989, and Short Protocols in Molecular Biology, ed. Ausubel, et al., hereby incorporated by reference. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Acid Probes, "Overview of principles of hybridization and the strategy of nucleic acid assays" (1993). Generally, stringent conditions are selected to be about 5-10° C. lower than the thermal melting point (Tm) for the specific sequence at a defined ionic strength and pH. The Tm is the temperature (under defined ionic strength, pH and nucleic acid concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of helix destabilizing agents such as formamide. The hybridization conditions may also vary when a non-ionic backbone, i.e., PNA is used, as is known in the art. In addition, cross-linking agents may be added after target binding to cross-link, i.e., covalently attach, the two strands of the hybridization complex.

Methods and compositions of the disclosure are useful for diagnosing or determining the presence of contamination or infection in a sample or subject, respectively. Such tests can be performed using DNA or RNA samples collected from blood, cells, biopsies, tissue scrapings, tissue culture, or other cellular materials. As will be appreciated by those in the art, target polynucleotides can be obtained from samples including, but not limited to, bodily fluids (e.g., blood, urine, serum, lymph, saliva, anal and vaginal secretions, perspiration and semen) of virtually any organism, with mammalian samples common to the methods of the disclosure and human samples being typical. The sample may comprise individual cells, including primary cells (including bacteria) and cell lines including, but not limited to, tumor cells of all types (particularly melanoma, myeloid leukemia, carcinomas of the lung, breast, ovaries, colon, kidney, prostate, pancreas and testes); cardiomyocytes; endothelial cells; epithelial cells; lymphocytes (T-cell and B cell); mast cells; eosinophils; vascular intimal cells; hepatocytes; leukocytes including mononuclear leukocytes; stem cells such as haemopoetic, neural, skin, lung, kidney, liver and myocyte stem cells; osteoclasts; chondrocytes and other connective tissue cells; keratinocytes; melanocytes; liver cells; kidney cells; and adipocytes. Suitable cells also include known research cells, including, but not limited to, Jurkat T cells, NIH3T3 cells, CHO, Cos, 923, HeLa, SiHa, WI-38, Weri-1, MG-63, and the like (see the ATCC cell line catalog, hereby expressly incorporated by reference).

Other methods to amplify and identify viral infection or contamination by MLV or XMRV will be recognized in the art and can be utilized in combination with the primers and probes identified herein. For example, one of skill in the art will recognize that Branched DNA, Hybrid Capture Assays, PCR (including RT, nested, multiplex, Real Time), Nucleic acid sequence-based amplification, transcription mediated amplification, strand displacement amplification, Ligase Chain Reaction, Cleavase-invader technology and cycling probe technology can be used with the oligonucleotides of the disclosure.

A target polynucleotide (e.g., a virus polynucleotide or gene) may be amplified using any oligonucleotide-directed amplification method including, but not limited to, polymerase chain reaction (PCR) (U.S. Pat. No. 4,965,188), ligase chain reaction (LCR) (Barany et al., Proc. Natl. Acad. Sci. USA 88:189-93 (1991); WO 90/01069), and oligonucleotide ligation assay (OLA) (Landegren et al., Science 241: 1077-80 (1988)). Other known nucleic acid amplification procedures may be used to amplify the target region(s) including transcription-based amplification systems (U.S. Pat. No. 5,130,238; European Patent No. EP 329,822; U.S. Pat. No. 5,169,766; WO 89/06700) and isothermal methods (Walker et al., Proc. Natl. Acad. Sci. USA 89:392-6 (1992)).

Ligase Chain Reaction (LCR) techniques can be used and are particularly useful for detection of single or multiple (e.g., 1, 2, 3, 4, or 5) nucleotide differences between similar polynucleotides. LCR occurs only when the oligonucleotides are correctly base-paired. The Ligase Chain Reaction (LCR), which utilizes the thermostable Taq ligase for ligation amplification, is useful for interrogating loci of a gene. LCR differs from PCR because it amplifies the probe molecule rather than producing amplicon through polymerization of nucleotides. Two probes are used per each DNA strand and are ligated together to form a single probe. LCR uses both a DNA polymerase enzyme and a DNA ligase enzyme to drive the reaction. Like PCR, LCR requires a thermal cycler to drive the reaction and each cycle results in a doubling of the target nucleic acid molecule. LCR can have greater specificity than PCR. The elevated reaction temperatures permit the ligation reaction to be conducted with high stringency. Where a mismatch occurs, ligation cannot be accomplished. For example, a probe based upon a target polynucleotide is synthesized in two fragments and annealed to the template with possible difference at the boundary of the two primer fragments. A ligase ligates the two primers if they match exactly to the template sequence.

In one embodiment, the two hybridization probes are designed each with a target specific portion. The first hybridization probe is designed to be substantially complementary to a first target domain of a target polynucleotide (e.g., a polynucleotide fragment) and the second hybridization probe is substantially complementary to a second target domain of a target polynucleotide (e.g., a polynucleotide fragment). In general, each target specific sequence of a hybridization probe is at least about 5 nucleotides long, with sequences of about 15 to 30 being typical and 20 being especially common. In one embodiment, the first and second target domains are directly adjacent, e.g., they have no intervening nucleotides. In this embodiment, at least a first hybridization probe is hybridized to the first target domain and a second hybridization probe is hybridized to the second target domain. If perfect complementarity exists at the junction, a ligation structure is formed such that the two probes can be ligated together to form a ligated probe. If this complementarity does not exist (due to mismatch), no ligation structure is formed and the probes are not ligated together to an appreciable degree. This may be done using heat cycling, to allow the ligated probe to be denatured off the target polynucleotide such that it may serve as a template for further reactions. The method may also be done using three hybridization probes or hybridization probes that are separated by one or more nucleotides, if dNTPs and a polymerase are added (this is sometimes referred to as "Genetic Bit" analysis).

Quantitative PCR and digital PCR can be used to measure the level of a polynucleotide in a sample. Digital Polymerase Chain Reaction (digital PCR, dPCR or dePCR) can be used to directly quantify and clonally amplify nucleic acids including DNA, cDNA or RNA. Digital PCR amplifies nucleic acids by temperature cycling of a nucleic acid molecule with a DNA polymerase. The reaction is typically carried out in the dispersed phase of an emulsion capturing each individual nucleic acid molecule present in a sample within many separate chambers or regions prior to PCR amplification. A count of chambers containing detectable levels of PCR end-product is a direct measure of the absolute nucleic acids quantity.

Quantitative polymerase chain reaction (qPCR) is a modification of the polymerase chain reaction and real-time quantitative PCR are useful for measuring the amount of DNA after each cycle of PCR by use of fluorescent markers or other detectable labels. Quantitative PCR methods use the addition of a competitor RNA (for reverse-transcriptase PCR) or DNA in serial dilutions or co-amplification of an internal control to ensure that the amplification is stopped while in the exponential growth phase.

Modifications of PCR and PCR techniques are routine in the art and there are commercially available kits useful for PCR amplification.

A probe or primer of the disclosure can be associated with a detectable label. A signaling component can include any label that can be detected optically, electronically, radioactively and the like. A nucleic acid analog may serve as the signaling component. By "label" or "detectable label" is meant a moiety that allows detection. In one embodiment, the detection label is a primary label. A primary label is one that can be directly detected, such as a fluorophore. In general, labels fall into three classes: a) isotopic labels, which may be radioactive or heavy isotopes; b) magnetic, electrical, thermal labels; and c) colored or luminescent dyes. Common labels include chromophores or phosphors but are typically fluorescent dyes. Suitable dyes for use in the disclosure include, but are not limited to; fluorescent lanthamide complexes, including those of Europium and Terbium, fluorescein, rhodamine, tetramethylrhodamine, eosin, erythrosin, coumarin, methyl-coumarins, quantum dots (also referred to as "nanocrystals"), pyrene, Malacite green, stilbene, Lucifer Yellow, Cascade Blue™, Texas Red, Cy dyes (Cy3, Cy5, and the like), Alexa dyes, phycoerythin, bodipy, and others described in the 6th Edition of the Molecular Probes Handbook by Richard P. Haugland, hereby expressly incorporated by reference.

Such a detectable label may be a radioactive label or may be a luminescent, fluorescent of enzyme label. Indirect detection processes typically comprise probes covalently labeled with a hapten or ligand such as digoxigenin (DIG) or biotin. In one embodiment, following the hybridization step, the target-probe duplex is detected by an antibody- or streptavidin-enzyme complex. Enzymes commonly used in DNA diagnostics are horseradish peroxidase and alkaline phosphatase. Direct detection methods include the use of fluorophor-labeled oligonucleotides, lanthanide chelate-labeled oligonucleotides or oligonucleotide-enzyme conjugates. Examples of fluorophor labels are fluorescein, rhodamine and phthalocyanine dyes.

It will be understood that embodiments of the invention include probes having fluorescent dye molecules, fluorescent compounds, or other fluorescent moieties. A dye molecule may fluoresce, or be induced to fluoresce upon excitation by application of suitable excitation energy (e.g., electromagnetic energy of suitable wavelength), and may also absorb electromagnetic energy ("quench") emitted by another dye molecule or fluorescent moiety. Any suitable fluorescent dye molecule, compound or moiety may be used in the practice of the invention. For example, suitable fluorescent dyes, compounds, and other fluorescent moieties include fluorescein, 6-carboxyfluorescein (6-FAM), 2',4',1, 4,-tetrachlorofluorescein (TET), 2',4',5',7',1,4-hexachlorofluorescein (HEX), 2',7'-dimethoxy-4',5'-dichloro-6-carboxyrhodamine (JOE), 2'-chloro-5'-fluoro-7',8'-fused phenyl-1,4-dichloro-6-carboxyfluorescein (NED) and 2'-chloro-7'-phenyl-1,4-dichloro-6-carboxyfluorescein (VIC), cyanine dyes (e.g., Cy.sup.3, Cy.sup.5, Cy.sup.9, nitrothiazole blue (NTB)), Cys3, FAM™, tetramethyl-6-carboxyrhodamine (TAMRA), tetrapropano-6-carboxyrhodamine (ROX), dipyrromethene boron fluoride (Bodipy), dichloro-fluorescein, dichloro-rhodamine, fluorescein thiosemicarbazide (FTC), sulforhodamine 101 acid chloride (Texas Red), phycoerythrin, rhodamine, carboxytetramethylrhodamine, 4,6-diamidino-2-phenylindole (DAPI), an indopyras dye, pyrenyloxytrisulfonic acid (Cascade Blue), 514 carboxylic acid (Oregon Green), eosin, erythrosin, pyridyloxazole, benzoxadiazole, aminonapthalene, pyrene, maleimide, a coumarin, 4-fluoro-7-nitrobenofurazan (NBD), 4-amino-N-[3-(vinylsulfonyl)-phenyl]naphthalimide-3,6-disulfonate) (Lucifer Yellow), DABCYL, DABSYL, anthraquinone, malachite green, nitrothiazole, and nitroimidazole compounds, propidium iodide, porphyrins, lanthamide cryptates, lanthamide chelates, derivatives and analogs thereof (e.g., 5-carboxy isomers of fluorescein dyes), and other fluorescent dyes and fluorescent molecules and compounds.

An oligonucleotide according to the methods of the invention may be labeled at the 5' end or the 3' end of at least one subunit of the probe. In embodiments, oligonucleotides may be labeled at both the 5' end and the 3' end. Alternatively, at least one subunit of the probe may be labeled internally, having at least one, and, in embodiments, more than one, internal label. In embodiments, an oligonucleotide may be labeled at an end and may be labeled internally. The oligonucleotides themselves are synthesized using techniques that are also well known in the art. Methods for preparing oligonucleotides of specific sequence are known in the art, and include, for example, cloning and restriction digest analysis of appropriate sequences and direct chemical synthesis, including, for example, the phosphotriester method described by Narang et al., 1979, Methods in Enzymology, 68:190, the phosphodiester method disclosed by Brown et al., 1979, Methods in Enzymology, 68:109, the diethylphosphoramidate method disclosed in Beaucage et al., 1981, Tetrahedron Letters, 22:1859, and the solid support method disclosed in U.S. Pat. No. 4,458,066, or by other chemical methods using a commercial automated oligonucleotide synthesizer. Modified linkages also may be included, for example phosphorothioates.

Examples of detection modes contemplated for the disclosed methods include, but are not limited to, spectroscopic techniques, such as fluorescence and UV-Vis spectroscopy, scintillation counting, and mass spectroscopy. Complementary to these modes of detection, examples of labels for the purpose of detection and quantitation used in these methods include, but are not limited to, chromophoric labels, scintillation labels, and mass labels. The expression levels of polynucleotides and polypeptides measured using these methods may be normalized to a control established for the purpose of the targeted determination.

Label detection will be based upon the type of label used in the particular assay. Such detection methods are known in the art. For example, radioisotope detection can be performed by autoradiography, scintillation counting or phosphor imaging. For hapten or biotin labels, detection is with an antibody or streptavidin bound to a reporter enzyme such as horseradish peroxidase or alkaline phosphatase, which is then detected by enzymatic means. For fluorophor or lanthanide-chelate labels, fluorescent signals may be measured with spectrofluorimeters with or without time-resolved mode or using automated microtitre plate readers. With enzyme labels, detection is by color or dye deposition (p-nitropheny phosphate or 5-bromo-4-chloro-3-indolyl phosphate/nitroblue tetrazolium for alkaline phosphatase and 3,3'-diaminobenzidine-NiCl$_2$ for horseradish peroxidase), fluorescence (e.g., 4-methyl umbelliferyl phosphate for alkaline phosphatase) or chemiluminescence (the alkaline phosphatase dioxetane substrates LumiPhos 530 from Lumigen Inc., Detroit Mich., or AMPPD and CSPD from Tropix, Inc.). Chemiluminescent detection may be carried out with X-ray or polaroid film or by using single photon counting luminometers.

The methods, compositions, systems and devices disclosed herein find use in the identification and quantization of a target DNA or RNA polynucleotide in a sample, such as in a pool of sequences including one or more target sequences, which may be unrelated polynucleotides. Quantization of specific nucleic acid samples may be achieved by comparing the total signal (fluorescent or otherwise) obtained during the assay with a standard curve of known polynucleotide target concentrations. Specific examples of applications include the detection of pathogenic viruses through the detection of their biomolecules such as DNA or RNA which are indicative of the presence of said targets. Assays having features of the invention may be used to detect and identify the presence of specific DNA sequences and may be used in assays for diagnosis of many types of infection and disease.

These assays are suitable for use on cell lysates, and contaminated samples as well. Since many clinical samples are rich with contaminants, it is advantageous that the described assays herein work under these conditions. Although many methods are currently available for DNA extraction and purification from tissues, assays such as those disclosed herein (QIAGEN kits, etc.), which are proficient in analyzing and working with contaminated samples, are very valuable and increases the robustness of the assay. For clinical sample use with the disclosed assays, sample preparation kits may be used. For example, samples suspected of containing pathogenic DNA may be used. Exemplary kits and protocols that can be used include the QIAamp MinElute Virus Spin Kit provided by Qiagen. This kit allows DNA isolation from clinical samples in roughly 1 hour. Other methods for sample preparation are available from suppliers such as Promega.

Polynucleotides may be prepared from samples using known techniques. For example, the sample may be treated to lyse a cell comprising the target polynucleotide, using known lysis buffers, sonication techniques, electroporation, and the like. Many methods for cell lysis are common knowledge for those trained in the art.

The following Examples are provided to illustrate and do not limit the invention.

EXAMPLES

The following abbreviations and definitions will assist in understanding aspect of the disclosure and the assays performed.

Ct (Cycle Threshold): Cycle number (in qPCR) at which the fluorescence generated within a reaction well exceeds the defined threshold. The threshold is arbitrarily defined by the qPCR instrument manufacturer to reflect the point during the reaction at which a sufficient number of amplicons have accumulated.

gDNA (genomic DNA): Deoxyribonucleic acid that has been purified from tissue and/or cultured cells.

Percentage Coefficient of Variation (% CV): The coefficient of variation (CV) is a normalized measure of dispersion of a probability distribution. It is defined as the ratio of the standard deviation σ to the mean μ:

$$c_V = \frac{\sigma}{\mu}$$

Slope: The slope or gradient of a line describes its steepness, incline, or grade. An acceptable slope of the linear regression equation for the qPCR should be within the range of −3.00 to −3.7.

R-squared ($R^2$) Value (also known as the Pearson Correlation Coefficient): The correlation of the line, $R^2$, is a measure of how well the data fits the model and how well the data fits on a straight line. It is influenced by pipetting accuracy and by the range of the assay. An $R^2$ of ≥0.94 is acceptable.

qPCR Percentage Efficiency (% Efficiency): Amplification efficiency, E, is the efficiency of amplification at varying template concentrations and is calculated from the slope of the standard curve using the following formula:

$E=10^\wedge(-1/\text{slope})$

The % efficiency is the percent of template that was amplified in each cycle and is calculated using the following formula:

% Efficiency=$(E-1)\times 100\%$

The % efficiency should be between 85% and 115%.

LOD: Limit of detection

LLOQ: Lower limit of quantitation.

ND: Non-detected.

NA: Not applicable.

NTC (Non-template control): A series of reaction wells in a qPCR experiment that contains all the reagents necessary for amplification with elution buffer or water substituted for sample DNA.

qPCR: Real-time quantitative polymerase chain reaction.

Example 1: Design of Primer/Probe Sets

Two primer/probe sets were designed for XMRV specific qPCR:

1. XMRV gag
XMRV 628F
(SEQ ID NO: 1)
(5'-ACTACCCCTCTGAGTCTAACC-3')

XMRV764R
(SEQ ID NO: 2)
(5'-GGCCATCCTACATTGAAAGTTG-3')

XMRV gag probe
(SEQ ID NO: 3)
(5'-FAM-CGCATTGCATCCAACCAGTCTGTG-3'-BHQ)

Amplification curves are shown in FIG. 6.

2. XMRV env
XMRV 6252F
(SEQ ID NO: 4)
(5'-TTTGATTCCTCAGTGGGCTC-3')

XMRV6391R
(SEQ ID NO: 5)
(5'-CGATACAGTCTTAGTCCCCATG-3')

XMRV env probe
(SEQ ID NO: 6)
(5'-HEX-CCCTTTTACCCGCGTCAGTGAATTCT-3'-BHQ)

Two primer probe sets were designed for detection of all MLV related retroviruses. Amplification curves are shown in FIG. 7.

3. MLV Pol 1
pol-F
(SEQ ID NO: 7)
(5'-AACAAGCGGGTGGAAGACATC-3')

pol-R
(SEQ ID NO: 8)
(5'-CAAAGGCGAAGAGAGGCTGAC-3')

pol probe
(SEQ ID NO: 9)
(5'-HEX-CCCACCGTGCCCAACCCTTACAACC-3'-TAMRA)

4. MLV Pol 2
5' Pol2 Primer
(SEQ ID NO: 10)
(CAAGGGGCTACTGGAGGAAAG)

3' Pol2 Primer:
(SEQ ID NO: 11)
(CTTTCCTCCATGTACCAGACTG)

Pol2 Probe:
(SEQ ID NO: 12)
(5HEX/TATCGCTGGACCACGGATCGCAA/3BHQ_1)

Two primer probe sets were designed for detection of amphotropic MLV virus:

5. MLV Env2
5'Env2 primer:
(SEQ ID NO: 13)
5'-ACCCTCAACCGCCCCTACAAGT-3'

3'Env2 primer:
(SEQ ID NO: 14)
5'-GTTAAGCGCCTGATAGGCTC-3'

Env2 probe:
(SEQ ID NO: 15)
5'-/FAM/CCCCAAATGAAAGACCCCCGCTGACG/BHQ/-3'

6. MLV LTR:
5' Primer = MLV-U3-B:
(SEQ ID NO: 16)
AGC CCA CAA CCC CTC ACT C

3' Primer = 3-MLV-Psi:
(SEQ ID NO: 17)
TCT CCC GAT CCC GGA CGA

FAM Probe = MLV-U5-Psi:
(SEQ ID NO: 18)
FAM-CCCCAAATGAAAGACCCCCGCTGACG 3BHQ_1

One primer probe set was designed for detection of a cytosine deaminase (CD) gene.

7. CD:
5' yCD2 Primer:
(SEQ ID NO: 19)
(ATC ATC ATG TAC GGC ATC CCT AG)

3' yCD2 Primer:
(SEQ ID NO: 20)
(TGA ACT GCT TCA TCA GCT TCT TAC)

yCD2 Probe:
(SEQ ID NO: 21)
(5FAM/TCA TCG TCA ACA ACC ACC ACC TCG T/3BHQ_1)

Oligonucleotides for primer probe sets were ordered from IDT (Integrated DNA Technologies, Inc., San Diego, Calif.).

Example 2: Preparation of Genomic DNA from Blood and Other Tissues from Mammals Including Human and Canines for PCR Testing The XMRV (xenotropic murine leukemia virus-related virus) qPCR assay is performed to quantify DNA. Total DNA extraction from the specimens samples is generated by standard means such as the use of commercially available kits (QIAGEN DNA blood mini kit, QIAGEN DNA Tissue kit, Promega DNA Tissue Kit, Promega DNA Cell Kit). A quantitation curve is established with 8 non-zero samples comprising of serial dilutions of defined copy number of reference plasmid to generate a Ct value versus copy number correlation. Linear regression analysis generates an equation which is used to calculate the copy number in the sample. Quantitative curves generation are shown for XMRV gag (FIG. 8), XMRV env (FIG. 9), XMRV pol2 (FIG. 10).

Example 3: Preparation of Plasma from Humans and Dogs for RT-PCR Testing

Blood was collected in blood collection tubes, and serum or plasma prepared from the whole blood by conventional means. The XMRV (xenotropic murine leukemia virus-related virus) RT-PCR assay is performed to quantify RNA from biological samples, such as whole blood and plasma, without the need for RNA extraction. The assay employs a two-step amplification process with the initial step consisting of the distribution of 2 μL of experimental sample directly into a cDNA reaction mix. Following completion of the reverse transcriptase (RT) cDNA synthesis, a 2 μL aliquot is removed, transferred into a qPCR reaction mix and a qPCR protocol is performed. A quantitation curve is established with 6 non-zero samples comprising of serial dilutions of defined copy number of reference vector to generate a Ct value versus copy number correlation. Linear regression analysis generates an equation which is used to calculate the copy number in the sample. Quantitative curves generation are shown in FIG. 15.

Example 4: Standardization and Validation of QPCR DNA Assays

A series of experiments were performed as outlined below:
1) To optimize the cycling parameters of the quantitative PCR (qPCR) protocol for XMRV detection including primer and probe concentrations and annealing temperature.
2) To assess detection sensitivity in spiked human whole blood genomic DNA (gDNA) targeted with the XMRV env, XMRV gag and XMRV pol2 primer/probe sets using qPCR.
3) To assess the use of an additional set of three pre-cycling steps (defined as a stage) in the qPCR protocol with respect to detection sensitivity.
4) To assess for variance in XMRV detection sensitivity from independent sources of human whole blood.
5) To assess for recovery of 22Rv1 XMRV positive control spiked into human whole blood gDNA.

Assay Design a. Optimization of Cycling Parameters for the qPCR Protocol.

A matrix of primers and probe were made up in various concentration combinations and were used to target the appropriate XMRV plasmid (pUC57 XMRV gag, pET28b XMRV env or pAZ3-emd pol2) containing the gene of interest. The choice of optimal primer concentrations were made based on comparisons of Ct value, standard deviation and relative fluorescence units (RFU). SYBR Green was used for the primer concentration optimization qPCR assay and TaqMan was used for the probe concentration optimization assay. Annealing temperature optimization was carried out by performing a qPCR annealing temperature gradient ranging from 50° C. to 65° C. Plasmids specific for the gene of interest were targeted with the appropriate XMRV primer sets.

b. Detection Sensitivity in Human Whole Blood gDNA Spiked with Plasmid DNA and Targeted with XMRV Env, XMRV Gag or XMRV Pol2 Primer/Probe Sets Using qPCR.

Genomic DNA extracted from human whole blood was spiked with known copy numbers of plasmid DNA containing the gene of interest. Serial log dilutions of the spiked gDNA were made and qPCR was performed. The samples were targeted with XMRV env (FIG. 9), XMRV gag (FIG. 8) and XMRV pol2 (FIG. 10) primer/probe sets in single qPCR reactions.

c. Detection Sensitivity in Human Whole Blood gDNA Spiked with Plasmid DNA and Targeted with XMRV Env, XMRV Gag or XMRV Pol2 Primer/Probe Sets Using a One-Stage qPCR Protocol.

Human whole blood gDNA was spiked with known copy numbers of plasmid DNA containing the gene of interest. Serial log dilutions of the spiked gDNA were made and a modified version of the qPCR protocol was performed by adding a set of three pre-cycling steps (defined as a one-stage qPCR protocol) to the current qPCR protocol. The samples were targeted with XMRV env (FIG. 9), XMRV gag (FIG. 8) and XMRV pol2 (FIG. 10) primer/probe sets in single qPCR reactions.

d. Assessment of XMRV Detection Sensitivity from Human Whole Blood Sourced from Healthy Donors and Spiked with Plasmid DNA.

Genomic DNA from whole blood from healthy donors were used to spike in known copy numbers of plasmid DNA. Serial dilutions of the gDNA were made to generate 1E3, 1E2, 1E1 and 1E0 copies per reaction. A 0-stage and a 1-stage qPCR protocol were performed. The samples were targeted with XMRV env (FIG. 12), XMRV gag (FIG. 11) or XMRV pol2 (FIG. 13) primer/probe sets in single qPCR reactions.

e. 22Rv1 Positive Control Recovery Assessment Spiked into Human Whole Blood gDNA.

22Rv1 gDNA (positive for XMRV, E. C. Knouf et al. J. Virol 83:78353-7356 2009) was spiked into purified human whole blood gDNA (pre and post gDNA extraction) at increasing log dilutions (one human whole blood sample control and one TE sample were spiked pre-extraction with 500 ng of 22Rv1 gDNA to yield a final concentration of ~2.5 ng/μL). A 0-stage and a 1-stage qPCR protocol were performed with primers targeting the XMRV gag, XMRV env and XMRV pol sequences.

Optimizations (primer concentration and temperature) for Pol primer set were carried out.

Both XMRV gag and XMRV env primer sets are XMRV specific whereas the Pol primer sets detect both MLV and XMRV.

A qPCR protocol used for all 4 primer sets: BioRad Supermix65.prcl

| | | |
|---|---|---|
| Step 1: | 95° C. | 5 min |
| Step 2: | 95° C. | 15 sec |
| Step 3: | 65° C. | 30 sec [repeat step 2-3 44X more times] |

FIGS. 6 and 7 show results obtained by the methods and compositions disclosed above.

TaqqMan® Gold RT-PCR Kit and TaqMan® PCR universal master mix are obtained from PE Biosystems. RNAeasy® mini kit and QIAamp® viral RNA mini kit are obtained from Qiagen. Various cell culture materials and biological samples to be tested are obtained from vendors or subjects.

MLV recombinant isolates comprise the sequences set forth in International Application No. PCT/US09/58512 and published on Apr. 1, 2010 as publication no. WO 2010/036986.

Two primer/probe sets for the detection of XMRV were designed as set forth above. One forward primer (FP), one reverse primer (RP), and one probe were used for the detection of XMRV gag and XMRV env. A third set of primer/probe was used for the detection of XMRV and MLV using the primers above that amplify the pol region of XMRV and MLV.

The qPCR reaction mixture contains 900 nM primers (both forward and reverse) and 200 nM probe. Concentrations tested to be effective for detection include, 100, 200, 300, 400, 500, 600, 700, 800, 900 nM and any ratio between 1:1, 1:2, 1:3, 1:4 of primer concentrations. The activation of Taq polymerase is achieved at 95° C. for 5 minutes is followed by forty-four cycles of denaturation at 95° C. for 15 seconds and annealing and elongation at 65° C. for 30 seconds.

Example 5: Detection of MLV in Formalin Fixed Paraffin Embedded Tissue Samples

Tumors from mice were removed and divided into 2 equal parts. One part of the tumor was formalin-fixed, paraffin-embedded and the other part of the tumor was frozen at −80° C. The FFPE mouse tumor tissue was cut in half, with one half spiked-in with a known copy number amount of pAZ3-emd and the other half was not spiked-in. A known copy number amount of pAZ3-emd was spiked-in to the frozen fresh mouse tissue and pre-processing incubation buffer. The FFPE and frozen fresh mouse tissues were incubated at 56° C. overnight in a pre-processing incubation buffer containing proteinase K and dithiothreitol (DTT). The following day, the mouse tissue was processed on the Maxwell 16 instrument to extract out gDNA as per standard procedure. The extracted gDNA concentration was quantified on the Nanodrop 1000. The extracted DNA was tested for presence of MLV and env2 sequences by qPCR with the results shown in FIG. 14.

Example 6: XMRV/MLV RT-PCR Assay

The XMRV (xenotropic murine leukemia virus-related virus) RT-PCR assay is performed to quantify RNA from biological samples, such as whole blood and plasma, without the need for RNA extraction. The assay employs a two-step amplification process with the initial step consisting of the distribution of 2 µL of experimental sample directly into a cDNA reaction mix. Following completion of the reverse transcriptase (RT) cDNA synthesis, a 2 µL aliquot is removed, transferred into a qPCR reaction mix and a qPCR protocol is performed. A quantitation curve is established with 7 non-zero samples comprising of serial dilutions of defined copy number of reference vector to generate a Ct value versus copy number correlation. Linear regression analysis generates an equation which is used to calculate the copy number in the sample. (FIG. 15).

Four control samples and one reagent control are used for this assay and are run in parallel with all test samples. The two step reaction requires controls for both the RT procedure and the qPCR procedure. Therefore, a positive, a negative and a non-template control are included for the cDNA synthesis step and a positive, negative and non-template control are included for the qPCR portion of the process.

A negative matrix sample (i.e. whole blood) is spiked with a defined quantity of 22Rv1 viral vector (see description under 'Reference Standard'). This control is prepared fresh with each run to determine the efficiency of the cDNA generation in the RT step.

22Rv1 genomic DNA containing the integrated retroviral vector sequences of XMRV provides the best biophysical mimic of the actual amplification target to be screened in patient tissues.

A negative matrix sample (i.e. whole blood) is used as a negative RT control as it does not contain any detectable XMRV endogenous sequences. This control is prepared fresh with each run to verify that non-specific products are not generated during cDNA synthesis of the qRT step. Confirmation is obtained upon completion of the qPCR procedure. No amplification is expected.

DNA isolated from non-infected U-87 cell is used as a negative control as it does not contain any endogenous sequences detectable by the XMRV primer sets.

The 22Rv1 human prostate carcinoma epithelial cell line has been shown to produce high-titer of the human retrovirus XMRV. This cell line was bought from ATCC and propagated in RPMI-1640 Medium containing 10% FBS, Sodium Pyruvate and Glutamax. The cell line was passaged four times before obtaining the supernatant containing the viral vector. The supernatant was filtered through a 0.45 m filter and stored at −80° C.

Reference vector 22Rv1 was used to spike PBS for generating a quantitation curve. Known copy numbers of vector were serially diluted to generate a Ct value versus copy number correlation. Linear regression analysis generates an equation which was used to calculate the copy number in the sample. Copy number was determined by a titer analysis which measures the number of copies of the viral genome integrated into the genome of target cells (transduction units, TU). The copy number was measured in TU equivalents.

Several studies were conducted to determine the appropriate primer sets, the optimal concentration for the reactions and the optimal temperature for the cycling parameters. Specific primer sets were designed and tested for human derived material. The goal of these experiments was to identify primer sets that were XMRV specific and did not present background in test samples.

The following primer sets were identified for targeting genes specific for XMRV:

```
1. XMRV gag
XMRV 628F
                                          (SEQ ID NO: 1)
(5'-ACTACCCCTCTGAGTCTAACC-3')

XMRV764R
                                          (SEQ ID NO: 2)
(5'-GGCCATCCTACATTGAAAGTTG-3')

XMRV gag probe
                                          (SEQ ID NO: 3)
(5'-FAM-CGCATTGCATCCAACCAGTCTGTG-3'-BHQ)

2. XMRV env
XMRV 6252F
                                          (SEQ ID NO: 4)
(5'-TTTGATTCCTCAGTGGGCTC-3')

XMRV6391R
                                          (SEQ ID NO: 5)
(5'-CGATACAGTCTTAGTCCCCATG-3')

XMRV env probe
                                          (SEQ ID NO: 6)
(5'-HEX-CCCTTTTACCCGCGTCAGTGAATTCT-3'-BHQ)
```

Two primer probe sets were designed for detection of all MLV related retroviruses and XMRV.

```
3. MLV Pol 1
pol-F
                                          (SEQ ID NO: 7)
(5'-AACAAGCGGGTGGAAGACATC-3')

pol-R
                                          (SEQ ID NO: 8)
(5'-CAAAGGCGAAGAGAGGCTGAC-3')

pol probe
                                          (SEQ ID NO: 9)
(5'-HEX-CCCACCGTGCCCAACCCTTACAACC-3'-TAMRA)

4. MLV Pol 2
5' Pol2 Primer
                                          (SEQ ID NO: 10)
(CAAGGGGCTACTGGAGGAAAG)

3' Pol2 Primer:
                                          (SEQ ID NO: 11)
(CTTTCCTCCATGTACCAGACTG)

Pol2 Probe:
                                          (SEQ ID NO: 12)
(5HEX/TATCGCTGGACCACGGATCGCAA/3BHQ_1)
```

Two primer probe sets were designed for detection of amphotropic MLV virus.

```
5. MLV Env2
5'Env2 primer:
                                          (SEQ ID NO: 13)
5'-ACCCTCAACCGCCCCTACAAGT-3'

3'Env2 primer:
                                          (SEQ ID NO: 14)
5'-GTTAAGCGCCTGATAGGCTC-3'

Env2 probe:
                                          (SEQ ID NO: 15)
5'-/FAM/CCCCAAATGAAAGACCCCCGCTGACG/BHQ/-3'
```

-continued

6. MLV LTR
One primer probe set was designed for detection of MLV in the LTR sequence
5'MLVLTR primer:

(SEQ ID NO: 16)
AGC CCA CAA CCC CTC ACT C

3' MLVLTR primer
(SEQ ID NO: 17)
TCT CCC GAT CCC GGA CGA

MLVLTR probe:
(SEQ ID NO: 18)
FAM-CCCCAAATGAAAGACCCCCGCTGACG 3BHQ_1

7. Cytosine deaminase gene
One primer probe set was designed for detection of the Cytosine deaminase gene
5' yCD2 Primer:
(SEQ ID NO: 19)
(ATC ATC ATG TAC GGC ATC CCT AG)

3' yCD2 Primer:
(SEQ ID NO: 20)
(TGA ACT GCT TCA TCA GCT TCT TAC)

yCD2 Probe:
(SEQ ID NO: 21)
(5FAM/TCA TCG TCA ACA ACC ACC ACC TCG T/3BHQ_1).

Example 7: Monitoring of GBM Patients Treated with an MLV Vector

Figure 16A:
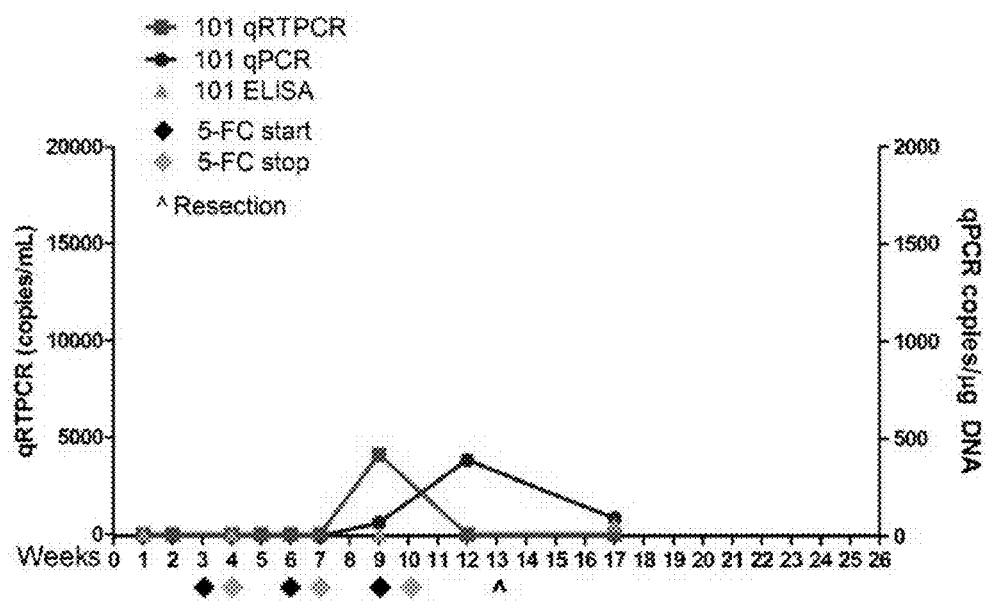
FIG. 16A-B shows the results of monitoring patients over time with assays described herein for provirus DNA (MLV-LTR primers and probes) in whole blood DNA, for viral RNA (by env RT-PCR) in the plasma, and for antiviral antibody responses in the plasma. These subjects (recurrent Glioblastoma multiforme (GBM) patients) were treated by intracranial injection of $2.6 \times 10^3$ TU/g brain of T5.0002 amphotropic MLV retrovirus encoding a modified yeast cytosine deaminase (WO2010036986, WO2010045002) followed by 5-fluorocytosine treatment courses at approximately 130 mg/kg/day. (A) patient 101; (B) patient 102.
Figure 16B:
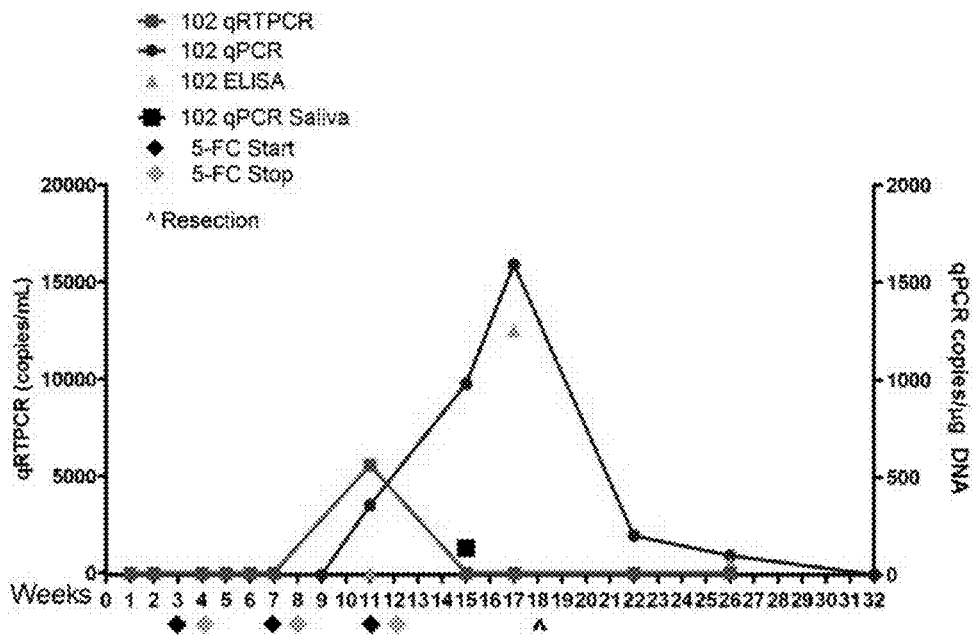

Open-label, ascending-dose trial of the safety and tolerability of increasing doses of Toca 511 administered to subjects with recurrent High Grade Glioma (including GBM) who have undergone surgery followed by adjuvant radiation and chemotherapy was carried out (see http[:]//clinicaltrials.gov/ct2/show/NCT01156584? term=tocagen&rank=1). Ascending doses of Toca 511(aka T5.0002) were prepared suitable for clinical use (WO2010148203) and delivered via stereotactic transcranial injection into the tumor. The starting dose was $2.6 \times 10^3$ TU/g. Subjects meeting all of the inclusion and none of the exclusion criteria received Toca 511 via stereotactic, transcranial injection into their tumor. Approximately three weeks (±1 week) later subjects underwent a baseline gadolinium-enhanced MRI (Gd-MRI) scan and then began treatment with oral 5-FC at approximately 130 mg/kg/day for 6 days. On the 4th, 5th or 6th day of dosing the trough 5-FC serum concentration was determined and the dose of 5-FC adjusted in subsequent cycles to maintain the trough concentration in the therapeutic range. If tolerated, these 6-day courses of 5-FC were repeated approximately every 4 weeks (±1 week) until institution of new antineoplastic treatment for tumor progression. Subjects undergo Gd-MRI scanning approximately every 8 weeks. Tumor response are assessed using the Macdonald criteria. A standard dose-escalation algorithm is being followed. Three subjects are evaluated at each of up to four dose levels of Toca 511 ($2.6 \times 10^3$, $9.5 \times 10^3$, $2.5 \times 10^4$, and the Maximum Feasible Dose [MFD], not to exceed $1 \times 10^5$ TU/g). So far three patients at the lowest dose level have been treated. Two patients 101 and 102 were monitored using qPCR testing of whole blood DNA (MLVLTR Primer probe set) and RT-qPCR using the MLV env2 primer-probe set. In addition, saliva an urine were monitored by DNA qPCR, and antibodies to the vector were measured (ref MLV ELISA Application?). These data are shown in FIG. 16.

Other primers useful in the methods and composition of the disclosure for detecting XMRV and MLV related viruses include those in Table 1.

TABLE 1

| Sequence Definition | Pair Rating | Product Length | Product Tm | Sense Primer (SEQ ID NO:) | Anti-sense Primer (SEQ ID NO:) | 5 XMRV position | 3 XMRV position |
|---|---|---|---|---|---|---|---|
| XMRV 1581-1778 | 66.8 | 178 | 78.2 | AGGTAGGAACCACCTAGTCC (28) | AGGGTCATAAGGAGTGTACC (29) | 1581 | 1758 |
| XMRV 1581-1778 | 63.6 | 168 | 78.3 | AGGTAGGAACCACCTAGTCC (30) | GGAGTGTACCTGCGATAGGC (31) | 1581 | 1748 |
| XMRV 1581-1778 | 63.5 | 198 | 78.9 | AGGTAGGAACCACCTAGTCC (32) | GTTTCTTGCCCTGGGTCCTC (33) | 1581 | 1778 |
| XMRV 1581-1778 | 62.5 | 188 | 78.8 | AGGTAGGAACCACCTAGTCC (34) | CTGGGTCCTCAGGGTCATAA (35) | 1581 | 1768 |
| XMRV 1581-1778 | 60.1 | 173 | 78 | AGGTAGGAACCACCTAGTCC (36) | CATAAGGAGTGTACCTGCGA (37) | 1581 | 1753 |
| XMRV 1729-1948 | 73.3 | 195 | 75.8 | TCGCAGGTACACTCCTTATG (38) | TCTCTTTCTTCCGGGGTTTC (39) | 1734 | 1928 |
| XMRV 1729-1948 | 69.8 | 215 | 76 | TCGCAGGTACACTCCTTATG (40) | TTTCTCTCCTGATACGTTCC (41) | 1734 | 1948 |
| XMRV 1729-1948 | 69 | 200 | 76 | TCGCAGGTACACTCCTTATG (42) | GTTCCTCTCTTTCTTCCGGG (43) | 1734 | 1933 |
| XMRV 1729-1948 | 68.2 | 200 | 76 | GCCTATCGCAGGTACACTCC (44) | TCTCTTTCTTCCGGGGTTTC (45) | 1729 | 1928 |
| XMRV 1729-1948 | 66 | 205 | 76.2 | GCCTATCGCAGGTACACTCC (46) | GTTCCTCTCTTTCTTCCGGG (47) | 1729 | 1933 |
| XMRV 1729-1948 | 66 | 210 | 76.2 | TCGCAGGTACACTCCTTATG (48) | CTCCTGATACGTTCCTCTCT (49) | 1734 | 1943 |

TABLE 1-continued

| Sequence Definition | Pair Rating | Product Length | Product Tm | Sense Primer (SEQ ID NO:) | Anti-sense Primer (SEQ ID NO:) | 5 XMRV position | 3 XMRV position |
|---|---|---|---|---|---|---|---|
| XMRV 1729-1948 | 63.8 | 180 | 75.1 | TTATGACCCTGAGGACCCAG (50) | TCTCTTTCTTCCGGGGTTTC (51) | 1749 | 1928 |
| XMRV 1729-1948 | 61.8 | 200 | 75.4 | TTATGACCCTGAGGACCCAG (52) | TTTCTCTCCTGATACGTTCC (53) | 1749 | 1948 |
| XMRV 1729-1948 | 61.4 | 210 | 75.8 | GGTACACTCCTTATGACCCT (54) | TTTCTCTCCTGATACGTTCC (55) | 1739 | 1948 |
| XMRV 1729-1948 | 61.1 | 185 | 75.3 | TTATGACCCTGAGGACCCAG (56) | GTTCCTCTCTTTCTTCCGGG (57) | 1749 | 1933 |

RT-PCR assay is performed to quantify RNA from biological samples, such as whole blood and plasma, without the need for RNA extraction. The assay employs a two-step amplification process with the initial step consisting of the distribution of 2 µL of experimental sample directly into a cDNA reaction mix. Following completion of the reverse transcriptase (RT) cDNA synthesis, a 2 µL aliquot is removed, transferred into a qPCR reaction mix and a qPCR protocol is performed.

In a separate embodiment, RNA is isolated from cell culture supernatants, whole blood or plasma using QIAamp® viral RNA Mini kit. The RNA is then used for reverse transcription. After reverse transcription, cDNA is subjected to qPCR assay.

A number of embodiments of the invention have been described. Nevertheless, it will be understood that various modifications may be made without departing from the spirit and scope of the invention. Accordingly, other embodiments are within the scope of the following claims.

What is claimed is:

1. An isolated oligonucleotide primer pair and probe, the primer pair consists of SEQ ID NO:10 and 11, or a sequence that is at least 95% identical to SEQ ID NO:10 and 11 and which can hybridize to an MLV-related polynucleotide.

2. A method of determining viral content in a subject prior to or after undergoing a retroviral gene delivery therapy using an MLV-related virus, comprising:
obtaining a sample from the subject;
contacting the sample with a primer pair as set forth in claim 1 under conditions suitable for nucleic acid amplification to obtain amplified products;
contacting the sample with a one or more probes that hydridizes to the amplified product;
detecting a hybridized product;
indicating that the subject has viral content comprising an MLV-related virus.

3. The method of claim 2, wherein the MLV-related virus is a recombinant retroviral vector used in gene delivery.

4. The method of claim 2, wherein the MLV-related virus is an XMRV virus.

5. The method of claim 2, wherein the MLV-related virus comprises a 5' LTR, gag, pol, env genes, a regulatory domain 3' of the env gene linked to a heterologous polynucleotide to be delivered and a 3' LTR.

6. The method of claim 5, wherein the regulatory domain is an internal ribosome entry site (IRES).

7. The method of claim 5, wherein the heterologous polynucleotide encodes a polypeptide having cytosine deaminase activity.

8. A method for detecting the presence of a viral agent in a sample comprising:
measuring the amount of a polynucleotide in a sample using a quantitative polymerase chain reaction or other amplification process comprising oligonucleotide primer/probe combination of claim 1.

9. The method of claim 8, wherein the polynucleotide is DNA.

10. The method of claim 8, wherein the polynucleotide is RNA.

11. The method of claim 8, wherein the quantitative polymerase chain reaction is RT-qPCR.

12. The method of claim 8, measuring detects a single copy of a viral agent related nucleic acid.

13. The method of claim 8, wherein the viral agent comprises a MLV related virus and/or XMRV.

14. The method of claim 8, wherein the sample is mammalian tissue or mammalian blood.

15. The method of claim 13, wherein the viral agent is a gene therapy vector.

16. The method of claim 15, wherein the gene therapy vector is a replication-competent vector.

17. The method of claim 8, wherein the method is performed prior to and/or subsequent to a therapeutic regimen comprising a gene therapy vector treatment.

18. The method of claim 8, wherein the method is performed to monitor the dosage of a therapeutic regimen comprising a gene therapy vector in a subject.

19. The method of claim 15, wherein the gene therapy vector comprises a replication competent MLV vector.

20. A kit comprising the isolated oligonucleotide primer pair and a probe of claim 1 and one or more reagents for (i) obtaining a sample from the subject; (ii) reverse transcribing RNA, and/or (iii) amplifying RNA or DNA.

21. A method of claim 2 for detecting <100 copies of MLV related DNA in a sample extracted from fixed histopathological sections.

22. A method of claim 2 for detecting <100 copies of MLV related RNA in a sample extracted from fixed histopathological sections.

23. A method of claim 2 or 8, wherein the method detects both MLV related virus and XMRV.

24. A method of claim 2 or 8, wherein the method detects only MLV related virus and does not detect XMRV.

25. A method of claim 2 or 8, wherein the method detects XMRV gag and MLV gag.

26. A method of claim 2 or 8, wherein the method detects XMRV pol and MLV pol.

27. A method of claim 2 or 8, wherein the method detects XMRV Env and MLV Env.

28. A method of screening a blood supply or tissue bank for infection by an MLV, MLV-variant or MLV-related virus comprising performing an amplification reaction on the blood supply or tissue bank utilizing the primers of claim 1, and detecting an amplified product.

29. The isolated oligonucleotide primer pair and a probe of claim 1, wherein the probe comprises the sequence of SEQ ID NO:12.

30. The isolated oligonucleotide primer pair and a probe of claim 29, wherein the probe is fluorescently labeled and comprises a sequence of SEQ ID NO:12.

* * * * *

SEQUENCE LISTING

<160> NUMBER OF SEQ ID NOS: 57

<210> SEQ ID NO 1
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 1 actaccccctc tgagtctaac c            21

<210> SEQ ID NO 2
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 2
ggccatccta cattgaaagt tg            22

<210> SEQ ID NO 3
<211> LENGTH: 24
<212> TYPE: DNA
<213> ORGANISM: Artificial Sequence
<220> FEATURE:
<223> OTHER INFORMATION: Oligonucleotide Probe

<400> SEQUENCE: 3
cgcattgcat ccaaccagtc tgtg            24

<210> SEQ ID NO 4
<211> LENGTH: 20
<212> TYPE: DNA
<213> ORGANISM: Artificial Sequence
<220> FEATURE:
<223> OTHER INFORMATION: Oligonucleotide primer

```
<400> SEQUENCE: 4
tttgattcct cagtgggctc                                              20

<210> SEQ ID NO 5
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 5
cgatacagtc ttagtcccca tg                                           22

<210> SEQ ID NO 6
<211> LENGTH: 26
<212> TYPE: DNA
<213> ORGANISM: Artificial Sequence
<220> FEATURE:
<223> OTHER INFORMATION: Oligonucleotide probe

<400> SEQUENCE: 6
cccttttacc cgcgtcagtg aattct                                       26

<210> SEQ ID NO 7
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 7
aacaagcggg tggaagacat c                                            21

<210> SEQ ID NO 8
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 8
caaaggcgaa gagaggctga c                                            21

<210> SEQ ID NO 9
<211> LENGTH: 25
<212> TYPE: DNA
<213> ORGANISM: Artificial Sequence
<220> FEATURE:
<223> OTHER INFORMATION: Oligonucleotide probe

<400> SEQUENCE: 9
cccaccgtgc ccaaccctta caacc                                        25

<210> SEQ ID NO 10
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 10
caaggggcta ctggaggaaa g                                            21

<210> SEQ ID NO 11
<211> LENGTH: 22
```

```
<212> TYPE: DNA
<213> ORGANISM: Artificial Sequence
<220> FEATURE:
<223> OTHER INFORMATION: Oligonucleotide primer

<400> SEQUENCE: 11
ctttcctcca tgtaccagac tg                                              22

<210> SEQ ID NO 12
<211> LENGTH: 23
<212> TYPE: DNA
<213> ORGANISM: Artificial Sequence
<220> FEATURE:
<223> OTHER INFORMATION: Oligonucleotide probe

<400> SEQUENCE: 12
tatcgctgga ccacggatcg caa                                             23

<210> SEQ ID NO 13
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 13
accctcaacc gccctacaa gt                                               22

<210> SEQ ID NO 14
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 14
gttaagcgcc tgataggctc                                                 20

<210> SEQ ID NO 15
<211> LENGTH: 26
<212> TYPE: DNA
<213> ORGANISM: Artificial Sequence
<220> FEATURE:
<223> OTHER INFORMATION: Oligonucleotide probe

<400> SEQUENCE: 15
ccccaaatga agaccccccg ctgacg                                          26

<210> SEQ ID NO 16
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 16
agcccacaac ccctcactc                                                  19

<210> SEQ ID NO 17
<211> LENGTH: 18
<212> TYPE: DNA
<213> ORGANISM: Artificial Sequence
<220> FEATURE:
<223> OTHER INFORMATION: Oligonucleotide primer

<400> SEQUENCE: 17
```

-continued

```
tctcccgatc ccggacga                                                    18
```

<210> SEQ ID NO 18
<211> LENGTH: 26
<212> TYPE: DNA
<213> ORGANISM: Artificial Sequence
<220> FEATURE:
<223> OTHER INFORMATION: Oligonucleotide probe

<400> SEQUENCE: 18

```
ccccaaatga aagacccccg ctgacg                                           26
```

<210> SEQ ID NO 19
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 19

```
atcatcatgt acggcatccc tag                                              23
```

<210> SEQ ID NO 20
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 20

```
tgaactgctt catcagcttc ttac                                             24
```

<210> SEQ ID NO 21
<211> LENGTH: 25
<212> TYPE: DNA
<213> ORGANISM: Artificial Sequence
<220> FEATURE:
<223> OTHER INFORMATION: Oligonucleotide probe

<400> SEQUENCE: 21

```
tcatcgtcaa caaccaccac ctcgt                                            25
```

<210> SEQ ID NO 22
<211> LENGTH: 11892
<212> TYPE: DNA
<213> ORGANISM: Artificial Sequence
<220> FEATURE:
<223> OTHER INFORMATION: RCR Vector - pAC3-yCD2

<400> SEQUENCE: 22

```
tagttattaa tagtaatcaa ttacggggtc attagttcat agcccatata tggagttccg      60
cgttacataa cttacggtaa atggcccgcc tggctgaccg cccaacgacc cccgcccatt     120
gacgtcaata atgacgtatg ttcccatagt aacgccaata gggactttcc attgacgtca     180
atgggtggag tatttacggt aaactgccca cttggcagta catcaagtgt atcatatgcc     240
aagtacgccc cctattgacg tcaatgacgg taaatggccc gcctggcatt atgcccagta     300
catgacctta tgggactttc ctacttggca gtacatctac gtattagtca tcgctattac     360
catggtgatg cggttttggc agtacatcaa tgggcgtgga tagcggtttg actcacgggg     420
atttccaagt ctccacccca ttgacgtcaa tgggagtttg ttttggcacc aaaatcaacg     480
ggactttcca aaatgtcgta caactccgcc ccattgacg caaatgggcg gtaggcgtgt     540
acggtgggag gtctatataa gcagagctgg tttagtgaac cggcgccagt cctccgattg     600
```

```
actgagtcgc ccgggtaccc gtgtatccaa taaaccctct tgcagttgca tccgacttgt    660
ggtctcgctg ttccttggga gggtctcctc tgagtgattg actacccgtc agcgggggtc    720
tttcatttgg gggctcgtcc gggatcggga accccctgcc cagggaccac cgacccacca    780
ccgggaggta agctggccag caacttatct gtgtctgtcc gattgtctag tgtctatgac    840
tgattttatg cgcctgcgtc ggtactagtt agctaactag ctctgtatct ggcggacccg    900
tggtggaact gacgagttcg gaacacccgg ccgcaaccct gggagacgtc cagggactt    960 cgggggccgt ttttgtggcc cgacctgagt ccaaaaatcc cgatcgtttt ggactctttg   1020 gtgcacccc cttagaggag ggatatgtgg ttctggtagg agacgagaac ctaaaacagt   1080
tcccgcctcc gtctgaattt ttgctttcgg tttgggaccg aagccgcgcc gcgcgtcttg   1140
tctgctgcag catcgttctg tgttgtctct gtctgactgt gtttctgtat ttgtctgaga   1200
atatgggcca gactgttacc actcccttaa gtttgacctt aggtcactgg aaagatgtcg   1260
agcggatcgc tcacaaccag tcggtagatg tcaagaagag acgttgggtt accttctgct   1320
ctgcagaatg gccaaccttt aacgtcggat ggccgcgaga cggcaccttt aaccgagacc   1380
tcatcaccca ggttaagatc aaggtctttt cacctggccc gcatggacac ccagaccagg   1440 tccctacat cgtgacctgg gaagccttgg cttttgaccc ccctccctgg gtcaagccct   1500
ttgtacaccc taagcctccg cctcctcttc tccatccgc cccgtctctc ccccttgaac   1560
ctcctcgttc gaccccgcct cgatcctccc tttatccagc cctcactcct tctctaggcg   1620
ccaaacctaa acctcaagtt ctttctgaca gtggggggcc gctcatcgac ctacttacag   1680 aagaccccc gccttatagg gacccaagac caccccttc cgacagggac ggaaatggtg   1740
gagaagcgac ccctgcggga gaggcaccgg acccctcccc aatggcatct cgcctacgtg   1800
ggagacggga gccccctgtg gccgactcca ctacctcgca ggcattcccc ctccgcgcag   1860
gaggaaacgg acagcttcaa tactggccgt tctcctcttc tgacctttac aactggaaaa   1920
ataataaccc ttcttttttct gaagatccag gtaaactgac agctctgatc gagtctgttc   1980
tcatcaccca tcagcccacc tgggacgact gtcagcagct gttggggact ctgctgaccg   2040
gagaagaaaa acaacgggtg ctcttagagg ctagaaaggc ggtgcgggc gatgatgggc   2100 gccccactca actgcccaat gaagtcgatg ccgcttttcc cctcgagcgc ccagactggg   2160
attacaccac ccaggcaggt aggaaccacc tagtccacta tcgccagttg ctcctagcgg   2220
gtctccaaaa cgcgggcaga agccccacca atttggccaa ggtaaaagga ataacacaag   2280
ggcccaatga gtctccctcg gccttcctag agagacttaa ggaagcctat cgcaggtaca   2340
ctccttatga ccctgaggac ccagggcaag aaactaatgt gtctatgtct ttcatttggc   2400
agtctgcccc agacattggg agaaagttag agaggttaga agatttaaaa acaagacgc   2460 ttggagattt ggttagagag gcagaaaaga tctttaataa acgagaaacc ccggaagaaa   2520
gagaggaacg tatcaggaga gaaacagagg aaaaagaaga acgccgtagg acagaggatg   2580
agcagaaaga gaaagaaaga gatcgtagga gacatagaga gatgagcaag ctattggcca   2640
ctgtcgttag tggacagaaa caggatagac agggaggaga acgaaggagg tcccaactcg   2700
atcgcgacca gtgtgcctac tgcaaagaaa aggggcactg gctaaagat tgtcccaaga   2760 aaccacgagg acctcgggga ccaagacccc agacctccct cctgacccta gatgactagg   2820
gaggtcaggt tcaggagccc cccctgaac ccaggataac cctcaaagtc gggggcaac   2880 ccgtcacctt cctggtagat actggggccc aaacactccgt gctgacccaa aatcctggac   2940
```

```
ccctaagtga taagtctgcc tgggtccaag gggctactgg aggaaagcgg tatcgctgga    3000
ccacggatcg caaagtacat ctagctaccg gtaaggtcac ccactctttc ctccatgtac    3060
cagactgtcc ctatcctctg ttaggaagag atttgctgac taaactaaaa gcccaaatcc    3120
actttgaggg atcaggagcc caggttatgg gaccaatggg gcagccctg caagtgttga     3180 ccctaaatat agaagatgag catcggctac atgagacctc aaaagagcca gatgtttctc    3240
tagggtccac atggctgtct gattttcctc aggcctgggc ggaaaccggg ggcatgggac    3300
tggcagttcg ccaagctcct ctgatcatac ctctgaaagc aacctctacc cccgtgtcca    3360
taaaacaata ccccatgtca caagaagcca gactggggat caagcccac atacagagac     3420 tgttggacca gggaatactg gtaccctgcc agtcccctg gaacacgccc ctgctacccg      3480
ttaagaaacc agggactaat gattataggc ctgtccagga tctgagagaa gtcaacaagc    3540
gggtggaaga catccacccc accgtgccca acccttacaa cctcttgagc gggctcccac    3600
cgtcccacca gtggtacact gtgcttgatt taaaggatgc cttttctgc ctgagactcc     3660 accccaccag tcagcctctc ttcgcctttg agtggagaga tccagagatg gaatctcag     3720 gacaattgac ctggaccaga ctcccacagg gttttcaaaaa cagtcccacc ctgtttgatg   3780
aggcactgca cagagaccta gcagacttcc ggatccagca cccagacttg atcctgctac    3840
agtacgtgga tgacttactg ctggccgcca cttctgagct agactgccaa caaggtactc    3900
gggccctgtt acaaaccta gggaacctcg ggtatcgggc ctcggccaag aaagcccaaa     3960
tttgccagaa acaggtcaag tatctggggt atcttctaaa agagggtcag agatggctga    4020
ctgaggccag aaaagagact gtgatggggc agcctactcc gaagacccct cgacaactaa    4080
gggagttcct agggacggca ggcttctgtc gcctctggat ccctgggttt gcagaaatgg    4140 cagcccctt gtaccctctc accaaaacgg ggactctgtt taattgggc ccagaccaac      4200 aaaaggccta tcaagaaatc aagcaagctc ttctaactgc cccagccctg gggttgccag    4260
atttgactaa gcccttgaa ctctttgtcg acgagaagca gggctacgcc aaaggtgtcc     4320
taacgcaaaa actgggacct tggcgtcggc cggtggccta cctgtccaaa aagctagacc    4380
cagtagcagc tgggtggccc ccttgcctac ggatggtagc agccattgcc gtactgacaa    4440
aggatgcagg caagctaacc atgggacagc cactagtcat tctggccccc catgcagtag    4500
aggcactagt caaacaaccc cccgaccgct ggctttccaa cgcccggatg actcactatc    4560
aggccttgct tttggacacg gaccgggtcc agttcggacc ggtggtagcc ctgaacccgg    4620
ctacgctgct cccactgcct gaggaagggc tgcaacacaa ctgccttgat atcctggccg    4680
aagcccacgg aaccgacccc gacctaacgg accagccgct cccagacgcc gaccacacct    4740
ggtacacgga tggaagcagt ctcttacaag agggacagcg taaggcggga gctgcggtga    4800
ccaccgagac cgaggtaatc tgggctaaag ccctgccagc cgggacatcc gctcagcggg    4860
ctgaactgat agcactcacc caggcccctaa agatggcaga aggtaagaag ctaaatgttt   4920
atactgatag ccgttatgct tttgctactg cccatatcca tggagaaata tacagaaggc    4980
gtgggttgct cacatcagaa ggcaaagaga tcaaaaataa agacgagatc ttggccctac    5040
taaaagcccc ctttctgccc aaaagactta gcataatcca ttgtccagga catcaaaagg    5100
gacacagcgc cgaggctaga ggcaaccgga tggctgacca agcggcccga aaggcagcca    5160
tcacagagac tccagacacc tctaccctcc tcatagaaaa ttcatcaccc tacacctcag    5220
aacattttca ttacacagtg actgatataa aggacctaac caagtggggg gccatttatg    5280
ataaaacaaa gaagtattgg gtctaccaag gaaaacctgt gatgcctgac cagtttactt    5340
```

```
ttgaattatt agactttctt catcagctga ctcacctcag cttctcaaaa atgaaggctc    5400
tcctagagag aagccacagt ccctactaca tgctgaaccg ggatcgaaca ctcaaaaata    5460
tcactgagac ctgcaaagct tgtgcacaag tcaacgccag caagtctgcc gttaaacagg    5520
gaactagggt ccgcgggcat cggcccggca ctcattggga gatcgatttc accgagataa    5580
agcccggatt gtatggctat aaatatcttc tagtttttat agatacccttt tctggctgga   5640 tagaagcctt cccaaccaag aaagaaaccg ccaaggtcgt aaccaagaag ctactagagg    5700
agatcttccc caggttcggc atgcctcagg tattgggaac tgacaatggg cctgccttcg    5760
tctccaaggt gagtcagaca gtggccgatc tgttggggat tgattggaaa ttacattgtg    5820
catacagacc ccaaagctca ggccaggtag aaagaatgaa tagaaccatc aaggagactt    5880
taactaaatt aacgcttgca actggctcta gagactgggg ctcctactc ccctttagccc    5940 tgtaccgagc ccgcaacacg ccgggccccc atggcctcac cccatatgag atcttatatg    6000
gggcaccccc gcccccttgta aacttccctg accctgacat gacaagagtt actaacagcc    6060
cctctctcca agctcactta caggctctct acttagtcca gcacgaagtc tggagacctc    6120
tggcggcagc ctaccaagaa caactggacc gaccggtggt acctcaccct taccgagtcg    6180
gcgacacagt gtgggtccgc cgacaccaga ctaagaacct agaacctcgc tggaaaggac    6240
cttacacagt cctgctgacc acccccaccg ccctcaaagt gacggcatc gcagcttgga    6300 tacacgccgc ccacgtgaag gctgccgacc ccggggggtgg accatcctct agactgacat    6360
ggcgcgttca acgctctcaa aaccccctca agataagatt aacccgtgga agcccttaat    6420
agtcatggga gtcctgttag gagtagggat ggcagagagc cccatcagg tctttaatgt    6480 aacctgagga gtcaccaacc tgatgactgg gcgtaccgcc aatgccacct ccctcctggg    6540
aactgtacaa gatgccttcc caaaattata ttttgatcta tgtgatctgg tcggagagga    6600
gtgggaccct tcagaccagg aaccgtatgt cgggtatggc tgcaagtacc ccgcagggag    6660
acagcggacc cggactttttg acttttacgt gtgccctggg cataccgtaa agtcggggtg    6720
tgggggacca ggagagggct actgtggtaa atggggggtgt gaaaccaccg gacaggctta    6780
ctggaagccc acatcatcgt gggacctaat ctcccttaag cgcggtaaca cccctggga    6840 cacgggatgc tctaaagttg cctgtggccc ctgctacgac ctctccaaag tatccaattc    6900
cttccaaggg gctactcgag ggggcagatg caacccctcta gtcctagaat tcactgatgc    6960
aggaaaaaag gctaactggg acgggcccaa atcgtgggga ctgagactgt accggacagg    7020
aacagatcct attaccatgt tctccctgac ccggcaggtc cttaatgtgg gaccccgagt    7080
ccccataggg cccaacccag tattacccga ccaaagactc ccttcctcac caatagagat    7140
tgtaccggct ccacagccac ctagccccct caataccagt tacccccctt ccactaccag    7200
tacaccctca acctccccta caagtccaag tgtcccacag ccaccccag gaactggaga    7260 tagactacta gctctagtca aaggagccta tcaggcgctt aacctcacca atcccgacaa    7320
gacccaagaa tgttggctgt gcttagtgtc gggacctcct tattacgaag gagtagcggt    7380
cgtgggcact tataccaatc attccaccgc tccggccaac tgtacggcca cttcccaaca    7440
taagcttacc ctatctgaag tgacaggaca gggcctatgc atgggggcag tacctaaaac    7500
tcaccaggcc ttatgtaaca ccacccaaag cgccggctca ggatcctact accttgcagc    7560
acccgccgga acaatgtggg cttgcagcac tggattgact ccctgcttgt ccaccacggt    7620
gctcaatcta accacagatt attgtgtatt agttgaactc tggcccagag taatttacca    7680
```

```
ctcccccgat tatatgtatg gtcagcttga acagcgtacc aaatataaaa gagagccagt    7740
atcattgacc ctggcccttc tactaggagg attaaccatg ggagggattg cagctggaat    7800
agggacgggg accactgcct taattaaaac ccagcagttt gagcagcttc atgccgctat    7860
ccagacagac ctcaacgaag tcgaaaagtc aattaccaac ctagaaaagt cactgacctc    7920
gttgtctgaa gtagtcctac agaaccgcag aggcctagat ttgctattcc taaaggaggg    7980
aggtctctgc gcagccctaa aagaagaatg ttgtttttat gcagaccaca cggggctagt    8040
gagagacagc atggccaaat taagagaaag gcttaatcag agacaaaaac tatttgagac    8100
aggccaagga tggttcgaag ggctgtttaa tagatccccc tggtttacca ccttaatctc    8160
caccatcatg ggacctctaa tagtactctt actgatctta ctctttggac cttgcattct    8220
caatcgattg gtccaatttg ttaaagacag gatctcagtg gtccaggctc tggttttgac    8280
tcagcaatat caccagctaa aacccataga gtacgagcca tgaacgcgtt actggccgaa    8340
gccgcttgga ataaggccgg tgtgcgtttg tctatatgtt attttccacc atattgccgt    8400
cttttggcaa tgtgagggcc cggaaacctg gccctgtctt cttgacgagc attcctaggg    8460
gtctttcccc tctcgccaaa ggaatgcaag gtctgttgaa tgtcgtgaag gaagcagttc    8520
ctctggaagc ttcttgaaga caaacaacgt ctgtagcgac cctttgcagg cagcggaacc    8580
ccccacctgg cgacaggtgc ctctgcggcc aaaagccacg tgtataagat acacctgcaa    8640
aggcggcaca accccagtgc cacgttgtga gttggatagt tgtggaaaga gtcaaatggc    8700
tctcctcaag cgtattcaac aaggggctga aggatgccca gaaggtaccc cattgtatgg    8760
gatctgatct ggggcctcgg tgcacatgct ttacatgtgt ttagtcgagg ttaaaaaaac    8820
gtctaggccc cccgaaccac ggggacgtgg ttttcctttg aaaaacacga ttataaatgg    8880
tgaccggcgg catggcctcc aagtgggatc aaaagggcat ggatatcgct tacgaggagg    8940
ccctgctggg ctacaaggag ggcggcgtgc ctatcggcgg ctgtctgatc aacaacaagg    9000
acggcagtgt gctgggcagg ggccacaaca tgaggttcca gaagggctcc gccaccctgc    9060
acggcgagat ctccaccctg gagaactgtg gcaggctgga gggcaaggtg tacaaggaca    9120
ccaccctgta caccaccctg tccccttgtg acatgtgtac cggcgctatc atcatgtacg    9180
gcatccctag gtgtgtgatc ggcgagaacg tgaacttcaa gtccaagggc gagaagtacc    9240
tgcaaaccag gggccacgag gtggtggttg ttgacgatga gaggtgtaag aagctgatga    9300
agcagttcat cgacgagagg cctcaggact ggttcgagga tatcggcgag taagcggccg    9360
cagataaaat aaaagatttt atttagtctc cagaaaaagg ggggaatgaa agaccccacc    9420
tgtaggtttg gcaagctagc ttaagtaacg ccattttgca aggcatggaa aaatacataa    9480
ctgagaatag agaagttcag atcaaggtca ggaacagatg aacagctgaa atatgggcca    9540
aacaggatat ctgtggtaag cagttcctgc cccggctcag ggccaagaac agatggaaca    9600
gctgaatatg ggccaaacag gatatctgtg taagcagtt cctgcccgg ctcagggcca    9660 agaacagatg gtccccagat gcggtccagc cctcagcagt ttctagagaa ccatcagatg    9720
tttccagggt gccccaagga cctgaaatga ccctgtgcct tatttgaact aaccaatcag    9780
ttcgcttctc gcttctgttc gcgcgcttct gctcccgag ctcaataaaa gagcccacaa    9840
cccctcactc ggggcgccag tcctccgatt gactgagtcg cccgggtacc cgtgtatcca    9900
ataaaccctc ttgcagttgc atccgacttg tggtctcgct gttccttggg agggtctcct    9960
ctgagtgatt gactacccgt cagcgggggt ctttcattac atgtgagcaa aaggccagca   10020
aaaggccagg aaccgtaaaa aggccgcgtt gctggcgttt ttccataggc tccgccccc   10080
```

-continued

```
tgacgagcat cacaaaaatc gacgctcaag tcagaggtgg cgaaacccga caggactata   10140
aagataccag gcgtttcccc ctggaagctc cctcgtgcgc tctcctgttc cgaccctgcc   10200
gcttaccgga tacctgtccg cctttctccc ttcgggaagc gtggcgcttt ctcaatgctc   10260
acgctgtagg tatctcagtt cggtgtaggt cgttcgctcc aagctgggct gtgtgcacga   10320
accccccgtt cagcccgacc gctgcgcctt atccggtaac tatcgtcttg agtccaaccc   10380
ggtaagacac gacttatcgc cactggcagc agccactggt aacaggatta gcagagcgag   10440
gtatgtaggc ggtgctacag agttcttgaa gtggtggcct aactacggct acactagaag   10500
gacagtattt ggtatctgcg ctctgctgaa gccagttacc ttcggaaaaa gagttggtag   10560
ctcttgatcc ggcaaacaaa ccaccgctgg tagcggtggt ttttttgttt gcaagcagca   10620
gattacgcgc agaaaaaaag gatctcaaga agatcctttg atcttttcta cggggtctga   10680
cgctcagtgg aacgaaaact cacgttaagg gattttggtc atgagattat caaaaaggat   10740
cttcacctag atccttttaa attaaaaatg aagttttaaa tcaatctaaa gtatatatga   10800
gtaaacttgg tctgacagtt accaatgctt aatcagtgag gcacctatct cagcgatctg   10860
tctatttcgt tcatccatag ttgcctgact ccccgtcgtg tagataacta cgatacggga   10920
gggcttacca tctggcccca gtgctgcaat gataccgcga gacccacgct caccggctcc   10980
agatttatca gcaataaacc agccagccgg aagggccgag cgcagaagtg gtcctgcaac   11040
tttatccgcc tccatccagt ctattaattg ttgccgggaa gctagagtaa gtagttcgcc   11100
agttaatagt ttgcgcaacg ttgttgccat tgctgcaggc atcgtggtgt cacgctcgtc   11160
gtttggtatg gcttcattca gctccggttc ccaacgatca aggcgagtta catgatcccc   11220
catgttgtgc aaaaaagcgg ttagctcctt cggtcctccg atcgttgtca gaagtaagtt   11280
ggccgcagtg ttatcactca tggttatggc agcactgcat aattctctta ctgtcatgcc   11340
atccgtaaga tgcttttctg tgactggtga gtactcaacc aagtcattct gagaatagtg   11400
tatgcggcga ccgagttgct cttgcccggc gtcaacacgg gataataccg cgccacatag   11460
cagaacttta aaagtgctca tcattggaaa acgttcttcg gggcgaaaac tctcaaggat   11520
cttaccgctg ttgagatcca gttcgatgta acccactcgt gcacccaact gatcttcagc   11580
atcttttact ttcaccagcg tttctgggtg agcaaaaaca ggaaggcaaa atgccgcaaa   11640
aaagggaata agggcgacac ggaaatgttg aatactcata ctcttccttt ttcaatatta   11700
ttgaagcatt tatcagggtt attgtctcat gagcggatac atatttgaat gtatttagaa   11760
aaataaacaa ataggggttc cgcgcacatt tccccgaaaa gtgccacctg acgtctaaga   11820
aaccattatt atcatgacat taacctataa aaataggcgt atcacgaggc cctttcgtct   11880
tcaagaattc at                                                       11892
```

<210> SEQ ID NO 23
<211> LENGTH: 11892
<212> TYPE: DNA
<213> ORGANISM: Artificial Sequence
<220> FEATURE:
<223> OTHER INFORMATION: RCR Vector - pAC3-yCD

<400> SEQUENCE: 23

```
tagttattaa tagtaatcaa ttacggggtc attagttcat agcccatata tggagttccg     60
cgttacataa cttacggtaa atggcccgcc tggctgaccg cccaacgacc cccgcccatt    120
gacgtcaata atgacgtatg ttcccatagt aacgccaata gggactttcc attgacgtca    180
```

-continued

```
atgggtggag tatttacggt aaactgccca cttggcagta catcaagtgt atcatatgcc    240
aagtacgccc cctattgacg tcaatgacgg taaatggccc gcctggcatt atgcccagta    300
catgacctta tgggactttc ctacttggca gtacatctac gtattagtca tcgctattac    360
catggtgatg cggttttggc agtacatcaa tgggcgtgga tagcggtttg actcacgggg    420
atttccaagt ctccacccca ttgacgtcaa tgggagtttg ttttggcacc aaaatcaacg    480
ggactttcca aaatgtcgta caactccgcc ccattgacg caaatgggcg gtaggcgtgt     540
acggtgggag gtctatataa gcagagctgg tttagtgaac cggcgccagt cctccgattg    600
actgagtcgc ccgggtaccc gtgtatccaa taaaccctct tgcagttgca tccgacttgt    660
ggtctcgctg ttccttggga gggtctcctc tgagtgattg actacccgtc agcggggtc    720 tttcatttgg gggctcgtcc gggatcggga accccctgcc cagggaccac cgacccacca    780
ccgggaggta agctggccag caacttatct gtgtctgtcc gattgtctag tgtctatgac    840
tgattttatg cgcctgcgtc ggtactagtt agctaactag ctctgtatct ggcggacccg    900
tggtggaact gacgagttcg gaacacccgg ccgcaaccct gggagacgtc ccaggggactt   960 cgggggccgt ttttgtggcc cgacctgagt ccaaaaatcc cgatcgtttt ggactctttg   1020 gtgcacccc cttagaggag ggatatgtgg ttctggtagg agacgagaac ctaaaacagt    1080
tcccgcctcc gtctgaattt ttgctttcgg tttgggaccg aagccgcgcc gcgcgtcttg   1140
tctgctgcag catcgttctg tgttgtctct gtctgactgt gtttctgtat ttgtctgaga   1200
atatgggcca gactgttacc actcccttaa gtttgacctt aggtcactgg aaagatgtcg   1260
agcggatcgc tcacaaccag tcggtagatg tcaagaagag cgttgggtt accttctgct    1320 ctgcagaatg gccaaccttt aacgtcggat ggccgcgaga cggcacctt aaccgagacc    1380 tcatcaccca ggtaagatc aaggtctttt cacctggccc gcatggacac ccagaccagg    1440
tcccctacat cgtgacctgg gaagccttgg cttttgaccc ccctccctgg gtcaagccct   1500
ttgtacaccc taagcctccg cctcctcttc tccatccgc cccgtctctc ccccttgaac    1560
ctcctcgttc gaccccgcct cgatcctccc tttatccagc cctcactcct tctctaggcg   1620
ccaaacctaa acctcaagtt ctttctgaca gtgggggcc gctcatcgac ctacttacag    1680
aagacccccc gccttatagg gacccaagac caccccttc cgacagggac ggaaatggtg    1740
gagaagcgac ccctgcggga gaggcaccgg acccctcccc aatggcatct cgcctacgtg   1800
ggagacggga gcccctgtg gccgactcca ctacctcgca ggcattcccc ctccgcgcag    1860
gaggaaacgg acagcttcaa tactggccgt tctcctcttc tgacctttac aactggaaaa   1920
ataataaccc ttctttttct gaagatccag gtaaactgac agctctgatc gagtctgttc   1980
tcatcaccca tcagcccacc tgggacgact gtcagcagct gttggggact ctgctgaccg   2040
gagaagaaaa acaacggggtg ctcttagagg ctagaaaggc ggtgcggggc gatgatgggc   2100
gccccactca actgcccaat gaagtcgatg ccgcttttcc cctcgagcgc ccagactggg   2160
attacaccac ccaggcaggt aggaaccacc tagtccacta tcgccagttg ctcctagcgg   2220
gtctccaaaa cgcgggcaga agccccacca atttggccaa ggtaaaagga ataacacaag   2280
ggcccaatga gtccctcg gccttcctag agagacttaa ggaagcctat cgcaggtaca    2340
ctccttatga ccctgaggac ccagggcaag aaactaatgt gtctatgtct ttcatttggc   2400
agtctgcccc agacattggg agaaagttag agaggttaga agatttaaaa aacaagacgc   2460
ttggagattt ggttagagag gcagaaaaga tctttaataa cgagaaacc ccggaagaaa    2520 gagaggaacg tatcaggaga gaaacagagg aaaagaaga acgccgtagg acagaggatg   2580
```

```
agcagaaaga gaaagaaaga gatcgtagga gacatagaga gatgagcaag ctattggcca    2640
ctgtcgttag tggacagaaa caggatagac agggaggaga acgaaggagg tcccaactcg    2700
atcgcgacca gtgtgcctac tgcaaagaaa aggggcactg gctaaagat tgtcccaaga     2760 aaccacgagg acctcgggga ccaagacccc agacctccct cctgaccta gatgactagg     2820 gaggtcaggg tcaggagccc ccccctgaac ccaggataac cctcaaagtc gggggcaac     2880 ccgtcacctt cctggtagat actggggccc aacactccgt gctgacccaa aatcctggac    2940
ccctaagtga taagtctgcc tgggtccaag gggctactgg aggaaagcgg tatcgctgga    3000
ccacggatcg caaagtacat ctagctaccg gtaaggtcac ccactctttc ctccatgtac    3060
cagactgtcc ctatcctctg ttaggaagag atttgctgac taaactaaaa gcccaaatcc    3120
actttgaggg atcaggagcc caggttatgg accaatggg gcagccctg caagtgttga     3180 ccctaaatat agaagatgag catcggctac atgagacctc aaaagagcca gatgtttctc    3240
tagggtccac atggctgtct gattttcctc aggcctgggc ggaaaccggg ggcatgggac    3300
tggcagttcg ccaagctcct ctgatcatac ctctgaaagc aacctctacc cccgtgtcca    3360
taaaacaata ccccatgtca caagaagcca gactggggat caagcccac atacagagac     3420 tgttggacca gggaatactg gtaccctgcc agtccccctg gaacacgccc ctgctacccg    3480
ttaagaaacc agggactaat gattataggc ctgtccagga tctgagagaa gtcaacaagc    3540
gggtggaaga catccacccc accgtgccca acccttacaa cctcttgagc gggctcccac    3600
cgtcccacca gtggtacact gtgcttgatt taaaggatgc ctttttctgc ctgagactcc    3660
accccaccag tcagcctctc ttcgcctttg agtggagaga tccagagatg ggaatctcag    3720
gacaattgac ctggaccaga ctcccacagg gtttcaaaaa cagtcccacc ctgtttgatg    3780
aggcactgca cagagaccta gcagacttcc ggatccagca cccagacttg atcctgctac    3840
agtacgtgga tgacttactg ctggccgcca cttctgagct agactgccaa caaggtactc    3900
gggccctgtt acaaacccta gggaacctcg ggtatcgggc ctcggccaag aaagcccaaa    3960
tttgccagaa acaggtcaag tatctgggt atcttctaaa agagggtcag agatggctga    4020
ctgaggccag aaaagagact gtgatggggc agcctactcc gaagacccct cgacaactaa    4080
gggagttcct agggacggca ggcttctgtc gcctctggat ccctgggttt gcagaaatgg    4140
cagccccctt gtaccctctc accaaaacgg ggactctgtt taattgggc ccagaccaac     4200 aaaaggccta tcaagaaatc aagcaagctc ttctaactgc cccagccctg gggttgccag    4260
atttgactaa gcccttgaa ctctttgtcg acgagaagca gggctacgcc aaaggtgtcc     4320
taacgcaaaa actgggacct tggcgtcggc cggtggccta cctgtccaaa agctagacc     4380 cagtagcagc tgggtggccc ccttgcctac ggatggtagc agccattgcc gtactgacaa    4440
aggatgcagg caagctaacc atgggacagc cactagtcat tctggcccc catgcagtag     4500 aggcactagt caaacaaccc cccgaccgct ggctttccaa cgcccggatg actcactatc    4560
aggccttgct tttggacacg gaccgggtcc agttcggacc ggtggtagcc ctgaacccgg    4620
ctacgctgct cccactgcct gaggaaggc tgcaacacaa ctgccttgat atcctggccg     4680
aagcccacgg aacccgaccc gacctaacgg accagccgct cccagacgcc gaccacacct    4740
ggtacacgga tggaagcagt ctcttacaag agggacagcg taaggcggga gctgcggtga    4800
ccaccgagac cgaggtaatc tgggctaaag ccctgccagc cggacatcc gctcagcggg     4860 ctgaactgat agcactcacc caggccctaa agatggcaga aggtaagaag ctaaatgttt    4920
```

```
atactgatag ccgttatgct tttgctactg cccatatcca tggagaaata tacagaaggc    4980
gtgggttgct cacatcagaa ggcaaagaga tcaaaaataa agacgagatc ttggccctac    5040
taaaagccct ctttctgccc aaaagactta gcataatcca ttgtccagga catcaaaagg    5100
gacacagcgc cgaggctaga ggcaaccgga tggctgacca agcggcccga aaggcagcca    5160
tcacagagac tccagacacc tctaccctcc tcatagaaaa ttcatcaccc tacacctcag    5220
aacattttca ttacacagtg actgatataa aggacctaac caagttgggg gccatttatg    5280
ataaaacaaa gaagtattgg gtctaccaag gaaaacctgt gatgcctgac cagtttactt    5340
ttgaattatt agactttctt catcagctga ctcacctcag cttctcaaaa atgaaggctc    5400
tcctagagag aagccacagt ccctactaca tgctgaaccg ggatcgaaca ctcaaaaata    5460
tcactgagac ctgcaaagct tgtgcacaag tcaacgccag caagtctgcc gttaaacagg    5520
gaactagggt ccgcgggcat cggcccggca ctcattggga gatcgatttc accgagataa    5580
agcccggatt gtatggctat aaatatcttc tagtttttat agatacctt tctggctgga    5640
tagaagcctt cccaaccaag aaagaaaccg ccaaggtcgt aaccaagaag ctactagagg    5700
agatcttccc caggttcggc atgcctcagg tattgggaac tgacaatggg cctgccttcg    5760
tctccaaggt gagtcagaca gtggccgatc tgttggggat tgattggaaa ttacattgtg    5820
catacagacc ccaaagctca ggccaggtag aaagaatgaa tagaaccatc aaggagactt    5880
taactaaatt aacgcttgca actggctcta gagactgggt gctcctactc cccttagccc    5940
tgtaccgagc ccgcaacacg ccgggccccc atggcctcac cccatatgag atcttatatg    6000
gggcaccccc gccccttgta aacttccctg accctgacat gacaagagtt actaacagcc    6060
cctctctcca agctcactta caggctctct acttagtcca gcacgaagtc tggagacctc    6120
tggcggcagc ctaccaagaa caactggacc gaccggtggg acctcaccct taccgagtcg    6180
gcgacacagt gtgggtccgc cgacaccaga ctaagaacct agaacctcgc tggaaaggac    6240
cttacacagt cctgctgacc acccccaccg ccctcaaagt agacggcatc gcagcttgga    6300
tacacgccgc ccacgtgaag gctgccgacc ccgggggtgg accatcctct agactgacat    6360
ggcgcgttca acgctctcaa aaccccctca agataagatt aacccgtgga agcccttaat    6420
agtcatggga gtcctgttag gagtagggat ggcagagagc cccatcagg tctttaatgt    6480
aacctggaga gtcaccaacc tgatgactgg gcgtaccgcc aatgccacct ccctcctggg    6540
aactgtacaa gatgccttcc caaaattata ttttgatcta tgtgatctgg tcggagagga    6600
gtgggacccct tcagaccagg aaccgtatgt cgggtatggc tgcaagtacc ccgcagggag    6660
acagcggacc cggactttg acttttacgt gtgccctggg cataccgtaa agtcggggtg    6720
tgggggacca ggagagggct actgtggtaa atgggggtgt gaaaccaccg acaggcttaa    6780
ctggaagccc acatcatcgt gggacctaat ctcccttaag cgcggtaaca ccccctggga    6840
cacgggatgc tctaaagttg cctgtggccc ctgctacgac ctctccaaag tatccaattc    6900
cttccaaggg gctactcgag ggggcagatg caacccctcta gtcctagaat tcactgatgc    6960
aggaaaaaag gctaactggg acgggcccaa atcgtgggga ctgagactgt accggacagg    7020
aacagatcct attaccatgt tctccctgac ccggcaggtc cttaatgtgg accccgagt    7080
ccccataggg cccaacccag tattacccga ccaaagactc ccttcctcac caatagagat    7140
tgtaccggct ccacagccac ctagcccct caataccagt tacccccctt ccactaccag    7200
tacaccctca acctccccta caagtccaag tgtcccacag ccaccccag gaactggaga    7260
tagactacta gctctagtca aaggagccta tcaggcgctt aaccctcacca atcccgacaa    7320
```

```
gacccaagaa tgttggctgt gcttagtgtc gggacctcct tattacgaag gagtagcggt    7380
cgtgggcact tataccaatc attccaccgc tccggccaac tgtacggcca cttcccaaca    7440
taagcttacc ctatctgaag tgacaggaca gggcctatgc atgggggcag tacctaaaac    7500
tcaccaggcc ttatgtaaca ccacccaaag cgccggctca ggatcctact accttgcagc    7560
acccgccgga acaatgtggg cttgcagcac tggattgact ccctgcttgt ccaccacggt    7620
gctcaatcta accacagatt attgtgtatt agttgaactc tggcccagag taatttacca    7680
ctcccccgat tatatgtatg gtcagcttga acagcgtacc aaatataaaa gagagccagt    7740
atcattgacc ctggcccttc tactaggagg attaaccatg ggagggattg cagctggaat    7800
agggacgggg accactgcct taattaaaac ccagcagttt gagcagcttc atgccgctat    7860
ccagacagac ctcaacgaag tcgaaaagtc aattaccaac ctagaaaagt cactgacctc    7920
gttgtctgaa gtagtcctac agaaccgcag aggcctagat ttgctattcc taaaggaggg    7980
aggtctctgc gcagccctaa aagaagaatg ttgtttttat gcagaccaca cggggctagt    8040
gagagacagc atggccaaat aagagaaag gcttaatcag agacaaaaac tatttgagac    8100
aggccaagga tggttcgaag ggctgtttaa tagatccccc tggtttacca ccttaatctc    8160
caccatcatg ggacctctaa tagtactctt actgatctta ctctttggac cttgcattct    8220
caatcgattg gtccaatttg ttaaagacag gatctcagtg gtccaggctc tggttttgac    8280
tcagcaatat caccagctaa aacccataga gtacgagcca tgaacgcgtt actggccgaa    8340
gccgcttgga ataaggccgg tgtgcgtttg tctatatgtt attttccacc atattgccgt    8400
cttttggcaa tgtgagggcc cggaaacctg gccctgtctt cttgacgagc attcctaggg    8460
gtctttcccc tctcgccaaa ggaatgcaag gtctgttgaa tgtcgtgaag gaagcagttc    8520
ctctggaagc ttcttgaaga caaacaacgt ctgtagcgac cctttgcagg cagcggaacc    8580
ccccacctgg cgacaggtgc ctctgcggcc aaaagccacg tgtataagat acacctgcaa    8640
aggcggcaca accccagtgc cacgttgtga gttggatagt tgtggaaaga gtcaaatggc    8700
tctcctcaag cgtattcaac aaggggctga aggatgccca gaaggtaccc cattgtatgg    8760
gatctgatct ggggcctcgg tgcacatgct ttacatgtgt ttagtcgagg ttaaaaaaac    8820
gtctaggccc cccgaaccac ggggacgtgg ttttcctttg aaaaacacga ttataaatgg    8880
tgacaggggg aatggcaagc aagtgggatc agaagggtat ggacattgcc tatgaggagg    8940
cggccttagg ttacaaagag ggtggtgttc ctattggcgg atgtcttatc aataacaaag    9000
acggaagtgt tctcggtcgt ggtcacaaca tgagatttca aaagggatcc gccacactac    9060
atggtgagat ctccactttg gaaaactgtg ggagattaga gggcaaagtg tacaaagata    9120
ccactttgta tacgacgctg tctccatgcg acatgtgtac aggtgccatc atcatgtatg    9180
gtattccacg ctgtgttgtc ggtgagaacg ttaatttcaa agtaagggc gagaaatatt    9240
tacaaactag aggtcacgag gttgttgttg ttgacgatga gaggtgtaaa agatcatga    9300
aacaatttat cgatgaaaga cctcaggatt ggtttgaaga tattggtgag taggcggccg    9360
cagataaaat aaaagatttt atttagtctc cagaaaaagg ggggaatgaa agaccccacc    9420
tgtaggtttg gcaagctagc ttaagtaacg ccattttgca aggcatggaa aaatacataa    9480
ctgagaatag agaagttcag atcaaggtca ggaacagatg gaacagctga atatgggcca    9540
aacaggatat ctgtggtaag cagttcctgc cccggctcag ggccaagaac agatggaaca    9600
gctgaatatg ggccaaacag gatatctgtg gtaagcagtt cctgccccgg ctcagggcca    9660
```

```
agaacagatg gtccccagat gcggtccagc cctcagcagt ttctagagaa ccatcagatg    9720
tttccagggt gccccaagga cctgaaatga ccctgtgcct tatttgaact aaccaatcag    9780
ttcgcttctc gcttctgttc gcgcgcttct gctccccgag ctcaataaaa gagcccacaa    9840
cccctcactc ggggcgccag tcctccgatt gactgagtcg cccgggtacc cgtgtatcca    9900
ataaaccctc ttgcagttgc atccgacttg tggtctcgct gttccttggg agggtctcct    9960
ctgagtgatt gactacccgt cagcgggggt ctttcattac atgtgagcaa aaggccagca   10020
aaaggccagg aaccgtaaaa aggccgcgtt gctggcgttt ttccataggc tccgcccccc   10080
tgacgagcat cacaaaaatc gacgctcaag tcagaggtgg cgaaacccga caggactata   10140
aagataccag gcgtttcccc ctggaagctc cctcgtgcgc tctcctgttc cgaccctgcc   10200
gcttaccgga tacctgtccg cctttctccc ttcgggaagc gtggcgcttt ctcaatgctc   10260
acgctgtagg tatctcagtt cggtgtaggt cgttcgctcc aagctgggct gtgtgcacga   10320
accccccgtt cagcccgacc gctgcgcctt atccggtaac tatcgtcttg agtccaaccc   10380
ggtaagacac gacttatcgc cactggcagc agccactggt aacaggatta gcagagcgag   10440
gtatgtaggc ggtgctacag agttcttgaa gtggtggcct aactacggct acactagaag   10500
gacagtattt ggtatctgcg ctctgctgaa gccagttacc ttcggaaaaa gagttggtag   10560
ctcttgatcc ggcaaacaaa ccaccgctgg tagcggtggt ttttttgttt gcaagcagca   10620
gattacgcgc agaaaaaaag gatctcaaga agatcctttg atcttttcta cggggtctga   10680
cgctcagtgg aacgaaaact cacgttaagg gattttggtc atgagattat caaaaaggat   10740
cttcacctag atccttttaa attaaaaatg aagttttaaa tcaatctaaa gtatatatga   10800
gtaaacttgg tctgacagtt accaatgctt aatcagtgag gcacctatct cagcgatctg   10860
tctatttcgt tcatccatag ttgcctgact ccccgtcgtg tagataacta cgatacggga   10920
gggcttacca tctggcccca gtgctgcaat gataccgcga gacccacgct caccggctcc   10980
agatttatca gcaataaacc agccagccgg aagggccgag cgcagaagtg gtcctgcaac   11040
tttatccgcc tccatccagt ctattaattg ttgccgggaa gctagagtaa gtagttcgcc   11100
agttaatagt ttgcgcaacg ttgttgccat tgctgcaggc atcgtggtgt cacgctcgtc   11160
gtttggtatg gcttcattca gctccggttc ccaacgatca aggcgagtta catgatcccc   11220
catgttgtgc aaaaaagcgg ttagctcctt cggtcctccg atcgttgtca gaagtaagtt   11280
ggccgcagtg ttatcactca tggttatggc agcactgcat aattctctta ctgtcatgcc   11340
atccgtaaga tgcttttctg tgactggtga gtactcaacc aagtcattct gagaatagtg   11400
tatgcggcga ccgagttgct cttgcccggc gtcaacacgg gataataccg cgccacatag   11460
cagaacttta aaagtgctca tcattggaaa acgttcttcg gggcgaaaac tctcaaggat   11520
cttaccgctg ttgagatcca gttcgatgta acccactcgt gcacccaact gatcttcagc   11580
atcttttact ttcaccagcg tttctgggtg agcaaaaaca ggaaggcaaa atgccgcaaa   11640
aaagggaata agggcgacac ggaaatgttg aatactcata ctcttccttt ttcaatatta   11700
ttgaagcatt tatcagggtt attgtctcat gagcggatac atatttgaat gtatttagaa   11760
aaataaacaa ataggggttc cgcgcacatt tccccgaaaa gtgccacctg acgtctaaga   11820
aaccattatt atcatgacat taacctataa aaataggcgt atcacgaggc cctttcgtct   11880
tcaagaattc at                                                      11892
```

<210> SEQ ID NO 24
<211> LENGTH: 12007

<212> TYPE: DNA
<213> ORGANISM: Artificial Sequence
<220> FEATURE:
<223> OTHER INFORMATION: RCR Vector - pACE-CD

<400> SEQUENCE: 24

```
tagttattaa tagtaatcaa ttacggggtc attagttcat agcccatata tggagttccg      60
cgttacataa cttacggtaa atggcccgcc tggctgaccg cccaacgacc cccgcccatt     120
gacgtcaata atgacgtatg ttcccatagt aacgccaata gggactttcc attgacgtca     180
atgggtggag tatttacggt aaactgccca cttggcagta catcaagtgt atcatatgcc     240
aagtacgccc cctattgacg tcaatgacgg taaatggccc gcctggcatt atgcccagta     300
catgacctta tgggactttc ctacttggca gtacatctac gtattagtca tcgctattac     360
catggtgatg cggttttggc agtacatcaa tgggcgtgga tagcggtttg actcacgggg     420
atttccaagt ctccacccca ttgacgtcaa tgggagtttg ttttggcacc aaaatcaacg     480
ggactttcca aaatgtcgta caactccgcc ccattgacg caaatgggcg gtaggcgtgt     540
acggtgggag gtctatataa gcagagctgg tttagtgaac cggcgccagt cctccgattg     600
actgagtcgc ccgggtaccc gtgtatccaa taaaccctct tgcagttgca tccgacttgt     660
ggtctcgctg ttccttggga gggtctcctc tgagtgattg actaccgtc agcggggtc      720
tttcatttgg ggctcgtcc gggatcggga gaccccctgcc cagggaccac cgacccacca     780
ccgggaggta agctggccag caacttatct gtgtctgtcc gattgtctag tgtctatgac     840
tgattttatg cgcctgcgtc ggtactagtt agctaactag ctctgtatct ggcggacccg     900
tggtggaact gacgagttcg gaacacccgg ccgcaaccct gggagacgtc ccagggactt     960
cgggggccgt ttttgtggcc cgacctgagt ccaaaaatcc cgatcgtttt ggactctttg    1020
gtgcaccccc cttagaggag ggatatgtgg ttctggtagg agacgagaac ctaaaacagt    1080
tcccgcctcc gtctgaattt ttgctttcgg tttgggaccg aagccgcgcc gcgcgtcttg    1140
tctgctgcag catcgttctg tgttgtctct gtctgactgt gtttctgtat ttgtctgaga    1200
atatgggcca gactgttacc actcccttaa gtttgacctt aggtcactgg aaagatgtcg    1260
agcggatcgc tcacaaccag tcggtagatg tcaagaagag acgttgggtt accttctgct    1320
ctgcagaatg gccaaccttt aacgtcggat ggccgcgaga cggcaccttt aaccgagacc    1380
tcatcaccca ggttaagatc aaggtctttt cacctggccc gcatggacac ccagaccagg    1440
tccctacat cgtgacctgg gaagccttgg cttttgaccc cctccctgg gtcaagccct    1500
ttgtacaccc taagcctccg cctcctcttc tccatccgc ccgtctctc cccttgaac     1560
ctcctcgttc gaccccgcct cgatcctccc tttatccagc cctcactcct tctctaggcg    1620
ccaaacctaa acctcaagtt ctttctgaca gtggggggcc gctcatcgac ctacttacag    1680
aagacccccc gccttatagg gacccaagac cacccccttc cgacagggac ggaaatggtg    1740
gagaagcgac ccctgcggga gaggcaccgg acccctcccc aatggcatct cgcctacgtg    1800
ggagacggga gccccctgtg gccgactcca ctacctcgca ggcattcccc ctccgcgcag    1860
gaggaaacgg acagcttcaa tactggccgt tctcctcttc tgacctttac aactggaaaa    1920
ataataaccc ttcttttct gaagatccag gtaaactgac agctctgatc gagtctgttc    1980
tcatcaccca tcagcccacc tgggacgact gtcagcagct gttggggact ctgctgaccg    2040
gagaagaaaa acaacgggtg ctcttagagg ctagaaaggc ggtgcgggc gatgatgggc    2100
gccccactca actgcccaat gaagtcgatg ccgctttttcc cctcgagcgc ccagactggg    2160
```

-continued

```
attacaccac ccaggcaggt aggaaccacc tagtccacta tcgccagttg ctcctagcgg    2220
gtctccaaaa cgcgggcaga agccccacca atttggccaa ggtaaaagga ataacacaag    2280
ggcccaatga gtctccctcg gccttcctag agagacttaa ggaagcctat cgcaggtaca    2340
ctccttatga ccctgaggac ccagggcaag aaactaatgt gtctatgtct ttcatttggc    2400
agtctgcccc agacattggg agaaagttag agaggttaga agatttaaaa aacaagacgc    2460
ttggagattt ggttagagag gcagaaaaga tctttaataa acgagaaacc ccggaagaaa    2520
gagaggaacg tatcaggaga gaaacagagg aaaagaaga acgccgtagg acagaggatg     2580
agcagaaaga gaaagaaaga gatcgtagga gacatagaga gatgagcaag ctattggcca    2640
ctgtcgttag tggacagaaa caggatagac agggaggaga acgaaggagg tcccaactcg    2700
atcgcgacca gtgtgcctac tgcaaagaaa aggggcactg gctaaagat tgtcccaaga     2760 aaccacgagg acctcgggga ccaagacccc agacctccct cctgacccta gatgactagg    2820
gaggtcaggg tcaggagccc ccccctgaac ccaggataac cctcaaagtc gggggggcaac   2880 ccgtcacctt cctggtagat actggggccc aacactccgt gctgacccaa aatcctggac    2940
ccctaagtga taagtctgcc tgggtccaag gggctactgg aggaaagcgg tatcgctgga   3000
ccacggatcg caaagtacat ctagctaccg gtaaggtcac ccactctttc ctccatgtac   3060
cagactgtcc ctatcctctg ttaggaagag atttgctgac taaactaaaa gcccaaatcc   3120
actttgaggg atcaggagcc caggttatgg gaccaatggg gcagccctg caagtgttga     3180 ccctaaatat agaagatgag catcggctac atgagacctc aaaagagcca gatgtttctc    3240
tagggtccac atggctgtct gattttcctc aggcctgggc ggaaaccggg gcatgggac    3300 tggcagttcg ccaagctcct ctgatcatac ctctgaaagc aacctctacc cccgtgtcca    3360
taaaacaata ccccatgtca caagaagcca gactggggat caagcccac atacagagac    3420 tgttggacca gggaatactg gtaccctgcc agtcccctg gaacacgccc ctgctacccg     3480
ttaagaaacc agggactaat gattataggc ctgtccagga tctgagagaa gtcaacaagc    3540
gggtggaaga catccacccc accgtgccca acccttacaa cctcttgagc gggctcccac    3600
cgtcccacca gtggtacact gtgcttgatt taaaggatgc cttttttctgc ctgagactcc   3660 accccaccag tcagcctctc ttcgcctttg agtggagaga tccagagatg ggaatctcag    3720
gacaattgac ctggaccaga ctcccacagg gtttcaaaaa cagtcccacc ctgtttgatg    3780
aggcactgca cagagaccta gcagacttcc ggatccagca cccagacttg atcctgctac    3840
agtacgtgga tgacttactg ctggccgcca cttctgagct agactgccaa caaggtactc    3900
gggccctgtt acaaaccta gggaacctcg ggtatcgggc ctcggccaag aaagcccaaa     3960
tttgccagaa acaggtcaag tatctggggt atcttctaaa agagggtcag agatggctga    4020
ctgaggccag aaaagagact gtgatggggc agcctactcc gaagacccct cgacaactaa    4080
gggagttcct agggacggca ggcttctgtc gcctctggat ccctgggttt gcagaaatgg    4140 cagcccccctt gtaccctctc accaaaacgg ggactctgtt taattggggc ccagaccaac    4200
aaaaggccta tcaagaaatc aagcaagctc ttctaactgc cccagccctg gggttgccag    4260
atttgactaa gcccttgaa ctctttgtcg acgagaagca gggctacgcc aaaggtgtcc     4320
taacgcaaaa actgggacct tggcgtcggc cggtggccta cctgtccaaa aagctagacc    4380
cagtagcagc tgggtggccc ccttgcctac ggatggtagc agccattgcc gtactgacaa    4440
aggatgcagg caagctaacc atgggacagc cactagtcat tctggccccc catgcagtag    4500
aggcactagt caaacaaccc cccgaccgct ggctttccaa cgcccggatg actcactatc    4560
```

```
aggccttgct tttggacacg gaccgggtcc agttcggacc ggtggtagcc ctgaacccgg   4620
ctacgctgct cccactgcct gaggaagggc tgcaacacaa ctgccttgat atcctggccg   4680
aagcccacgg aacccgaccc gacctaacgg accagccgct cccagacgcc gaccacacct   4740
ggtacacgga tggaagcagt ctcttacaag agggacagcg taaggcggga gctgcggtga   4800
ccaccgagac cgaggtaatc tgggctaaag ccctgccagc cgggacatcc gctcagcggg   4860
ctgaactgat agcactcacc caggccctaa agatggcaga aggtaagaag ctaaatgttt   4920
atactgatag ccgttatgct tttgctactg cccatatcca tggagaaata tacagaaggc   4980
gtgggttgct cacatcagaa ggcaaagaga tcaaaaataa agacgagatc ttggccctac   5040
taaaagccct ctttctgccc aaaagactta gcataatcca ttgtccagga catcaaaagg   5100
gacacagcgc cgaggctaga ggcaaccgga tggctgacca agcggcccga aaggcagcca   5160
tcacagagac tccagacacc tctaccctcc tcatagaaaa ttcatcaccc tacacctcag   5220
aacattttca ttacacagtg actgatataa aggacctaac caagttgggg gccatttatg   5280
ataaaacaaa gaagtattgg gtctaccaag gaaaacctgt gatgcctgac cagtttactt   5340
ttgaattatt agactttctt catcagctga ctcacctcag cttctcaaaa atgaaggctc   5400
tcctagagag aagccacagt ccctactaca tgctgaaccg ggatcgaaca ctcaaaaata   5460
tcactgagac ctgcaaagct tgtgcacaag tcaacgccag caagtctgcc gttaaacagg   5520
gaactagggt ccgcgggcat cggcccggca ctcattggga gatcgatttc accgagataa   5580
agcccggatt gtatggctat aaatatcttc tagtttttat agatacctt tctggctgga   5640 tagaagcctt cccaaccaag aaagaaaccg ccaaggtcgt aaccaagaag ctactagagg   5700
agatcttccc caggttcggc atgcctcagg tattgggaac tgacaatggg cctgccttcg   5760
tctccaaggt gagtcagaca gtggccgatc tgttggggat tgattggaaa ttacattgtg   5820
catacagacc ccaaagctca ggccaggtag aaagaatgaa tagaaccatc aaggagactt   5880
taactaaatt aacgcttgca actggctcta gagactgggt gctcctactc cccttagccc   5940
tgtaccgagc ccgcaacacg ccgggccccc atggcctcac cccatatgag atcttatatg   6000
gggcaccccc gccccttgta aacttccctg accctgacat gacaagagtt actaacagcc   6060
cctctctcca agctcactta caggctctct acttagtcca gcacgaagtc tggagacctc   6120
tggcggcagc ctaccaagaa caactggacc gaccggtggt acctcaccct taccgagtcg   6180
gcgacacagt gtgggtccgc cgacaccaga ctaagaacct agaacctcgc tggaaaggac   6240
cttacacagt cctgctgacc accccaccg ccctcaaagt agacggcatc gcagcttgga   6300
tacacgccgc ccacgtgaag gctgccgacc ccggggtgg accatcctct agactgacat   6360
ggcgcgttca acgctctcaa aaccccctca agataagatt aacccgtgga agcccttaat   6420
agtcatggga gtcctgttag gagtagggat ggcagagagc ccccatcagg tctttaatgt   6480
aacctggaga gtcaccaacc tgatgactgg gcgtaccgcc aatgccacct ccctcctggg   6540
aactgtacaa gatgccttcc caaaattata ttttgatcta tgtgatctgg tcggagagga   6600 gtgggacct tcagaccagg aaccgtatgt cgggtatggc tgcaagtacc ccgcagggag   6660
acagcggacc cggactttg acttttacgt gtgccctggg cataccgtaa agtcggggtg   6720
tgggggacca ggagagggct actgtggtaa atggggtgt gaaaccaccg gacaggctta   6780
ctggaagccc acatcatcgt gggacctaat ctcccttaag cgcggtaaca ccccctggga   6840
cacgggatgc tctaaagttg cctgtggccc ctgctacgac ctctccaaag tatccaattc   6900
```

```
cttccaaggg gctactcgag ggggcagatg caaccctcta gtcctagaat tcactgatgc  6960
aggaaaaaag gctaactggg acgggcccaa atcgtgggga ctgagactgt accggacagg  7020
aacagatcct attaccatgt tctccctgac ccggcaggtc cttaatgtgg gacccccagt  7080
ccccataggg cccaacccag tattacccga ccaaagactc ccttcctcac caatagagat  7140
tgtaccggct ccacagccac ctagccccct caataccagt tacccccctt ccactaccag  7200
tacaccctca acctccccta caagtccaag tgtcccacag ccaccccag gaactggaga  7260 tagactacta gctctagtca aaggagccta tcaggcgctt aacctcacca atcccgacaa  7320
gacccaagaa tgttggctgt gcttagtgtc gggacctcct tattacgaag gagtagcggt  7380
cgtgggcact tataccaatc attccaccgc tccggccaac tgtacggcca cttcccaaca  7440
taagcttacc ctatctgaag tgacaggaca gggcctatgc atgggggcag tacctaaaac  7500
tcaccaggcc ttatgtaaca cacccaaag cgccggctca ggatcctact accttgcagc  7560
acccgccgga acaatgtggg cttgcagcac tggattgact ccctgcttgt ccaccacggt  7620
gctcaatcta accacagatt attgtgtatt agttgaactc tggcccagag taatttacca  7680
ctcccccgat tatatgtatg gtcagcttga acagcgtacc aaatataaaa gagagccagt  7740
atcattgacc ctggcccttc tactaggagg attaaccatg ggagggattg cagctggaat  7800
agggacgggg accactgcct taattaaaac ccagcagttt gagcagcttc atgccgctat  7860
ccagacagac ctcaacgaag tcgaaaagtc aattaccaac ctagaaaagt cactgacctc  7920
gttgtctgaa gtagtcctac agaaccgcag aggcctagat ttgctattcc taaggagggg  7980
aggtctctgc gcagccctaa aagaagaatg ttgtttttat gcagaccaca cggggctagt  8040
gagagacagc atggccaaat taagagaaag gcttaatcag agacaaaaac tatttgagac  8100
aggccaagga tggttcgaag ggctgtttaa tagatccccc tggtttacca ccttaatctc  8160
caccatcatg ggacctctaa tagtactctt actgatctta ctcttggac cttgcattct  8220 caatcgatta gtccaatttg ttaaagacag gatatcagtg gtccaggctc tagttttgac  8280
tcaacaatat caccagctga agcctataga gtacgagcca tgacgtacgt tactggccga  8340
agccgcttgg aataaggccg gtgtgcgttt gtctatatgt tattttccac catattgccg  8400
tcttttggca atgtgagggc ccggaaacct ggccctgtct tcttgacgag cattcctagg  8460
ggtctttccc ctctcgccaa aggaatgcaa ggtctgttga atgtcgtgaa ggaagcagtt  8520
cctctggaag cttcttgaag acaaacaacg tctgtagcga ccctttgcag gcagcggaac  8580
cccccacctg gcgacaggtg cctctgcggc caaaagccac gtgtataaga tacacctgca  8640
aaggcggcac aaccccagtg ccacgttgtg agttggatag ttgtggaaag agtcaaatgg  8700
ctctcctcaa gcgtattcaa caagggggctg aaggatgccc agaaggtacc ccattgtatg  8760
ggatctgatc tggggcctcg gtgcacatgc tttacatgtg tttagtcgag gttaaaaaaa  8820
cgtctaggcc ccccgaacca cggggacgtg gttttccttt gaaaaacacg ataataccat  8880
ggtgacaggg ggaatggcaa gcaagtggga tcagaagggt atggacattg cctatgagga  8940
ggcggcctta ggttacaaag agggtggtgt tcctattggc ggatgtctta tcaataacaa  9000
agacggaagt gttctcggtc gtggtcacaa catgagattt caaaagggat ccgccacact  9060
acatggtgag atctccactt tggaaaactg tgggagatta gagggcaaag tgtacaaaga  9120
taccactttg tatacgacgc tgtctccatg cgacatgtgt acaggtgcca tcatcatgta  9180
tggtattcca cgctgtgttg tcggtgagaa cgttaatttc aaaagtaagg gcgagaaata  9240
tttacaaact agaggtcacg aggttgttgt tgttgacgat gagaggtgta aaaagatcat  9300
```

```
gaaacaattt atcgatgaaa gacctcagga ttggtttgaa gatattggtg agtaggcggc    9360
cgcgccatag ataaaataaa agattttatt tagtctccag aaaaaggggg gaatgaaaga    9420
ccccacctgt aggtttggca agctagctta agtaacgcca ttttgcaagg catggaaaaa    9480
tacataactg agaatagaga agttcagatc aaggtcagga acagatggaa cagctgaata    9540
tgggccaaac aggatatctg tggtaagcag ttcctgcccc ggctcagggc aagaacaga     9600
tggaacagct gaatatgggc caaacaggat atctgtggta agcagttcct gccccggctc    9660
agggccaaga acagatggtc cccagatgcg gtccagccct cagcagtttc tagagaacca    9720
tcagatgttt ccagggtgcc ccaaggacct gaaatgaccc tgtgccttgt ttaaactaac    9780
caatcagttc gcttctcgct tctgttcgcg cgcttctgct ccccgagctc aataaaagag    9840
cccacaaccc ctcactcggg gcgccagtcc tccgattgac tgagtcgccc gggtacccgt    9900
gtatccaata aaccctcttg cagttgcatc cgacttgtgg tctcgctgtt ccttgggagg    9960
gtctcctctg agtgattgac tacccgtcag cgggggtctt tcatttgggg gctcgtccgg   10020
gatcgggaga cccctgccca gggaccaccg acccaccacc gggaggtaag ctggctgcct   10080
cgcgcgtttc ggtgatgacg gtgaaaacct ctgacatgtg agcaaaaggc cagcaaaagg   10140
ccaggaaccg taaaaaggcc gcgttgctgg cgttttttcca taggctccgc cccctgacg   10200
agcatcacaa aaatcgacgc tcaagtcaga ggtggcgaaa cccgacagga ctataaagat   10260
accaggcgtt ccccctgga agctccctcg tgcgctctcc tgttccgacc ctgccgctta   10320
ccggatacct gtccgccttt ctcccttcgg gaagcgtggc gctttctcaa tgctcacgct   10380
gtaggtatct cagttcggtg taggtcgttc gctccaagct gggctgtgtg cacgaacccc   10440
ccgttcagcc cgaccgctgc gccttatccg gtaactatcg tcttgagtcc aacccggtaa   10500
gacacgactt atcgccactg gcagcagcca ctggtaacag gattagcaga gcgaggtatg   10560
taggcggtgc tacagagttc ttgaagtggt ggcctaacta cggctacact agaaggacag   10620
tatttggtat ctgcgctctg ctgaagccag ttaccttcgg aaaaagagtt ggtagctctt   10680
gatccggcaa acaaaccacc gctggtagcg gtggtttttt tgtttgcaag cagcagatta   10740
cgcgcagaaa aaaaggatct caagaagatc ctttgatctt ttctacgggg tctgacgctc   10800
agtggaacga aaactcacgt taagggattt tggtcatgag attatcaaaa aggatcttca   10860
cctagatcct tttaaattaa aaatgaagtt ttaaatcaat ctaaagtata tatgagtaaa   10920
cttggtctga cagttaccaa tgcttaatca gtgaggcacc tatctcagcg atctgtctat   10980
ttcgttcatc catagttgcc tgactccccg tcgtgtagat aactacgata cgggagggct   11040
taccatctgg ccccagtgct gcaatgatac cgcgagaccc acgctcaccg gctccagatt   11100
tatcagcaat aaaccagcca gccggaaggg ccgagcgcag aagtggtcct gcaactttat   11160
ccgcctccat ccagtctatt aattgttgcc gggaagctag agtaagtagt tcgccagtta   11220
atagtttgcg caacgttgtt gccattgctg caggcatcgt ggtgtcacgc tcgtcgtttg   11280
gtatggcttc attcagctcc ggttcccaac gatcaaggcg agttacatga tcccccatgt   11340
tgtgcaaaaa agcggttagc tccttcggtc ctccgatcgt tgtcagaagt aagttggccg   11400
cagtgttatc actcatggtt atggcagcac tgcataattc tcttactgtc atgccatccg   11460
taagatgctt ttctgtgact ggtgagtact caaccaagtc attctgagaa tagtgtatgc   11520
ggcgaccgag ttgctcttgc ccggcgtcaa cacgggataa taccgcgcca catagcagaa   11580
ctttaaaagt gctcatcatt ggaaaacgtt cttcggggcg aaaactctca aggatcttac   11640
```

| | |
|---|---:|
| cgctgttgag atccagttcg atgtaaccca ctcgtgcacc caactgatct tcagcatctt | 11700 |
| ttactttcac cagcgtttct gggtgagcaa aaacaggaag gcaaaatgcc gcaaaaaagg | 11760 |
| gaataagggc gacacggaaa tgttgaatac tcatactctt cctttttcaa tattattgaa | 11820 |
| gcatttatca gggttattgt ctcatgagcg gatacatatt tgaatgtatt tagaaaaata | 11880 |
| aacaaatagg ggttccgcgc acatttcccc gaaaagtgcc acctgacgtc taagaaacca | 11940 |
| ttattatcat gacattaacc tataaaaata ggcgtatcac gaggccctt cgtcttcaag | 12000 |
| aattcat | 12007 |

<210> SEQ ID NO 25
<211> LENGTH: 11893
<212> TYPE: DNA
<213> ORGANISM: Artificial Sequence
<220> FEATURE:
<223> OTHER INFORMATION: RCR Vector - pAC3-yCD2

<400> SEQUENCE: 25

| | |
|---|---:|
| tagttattaa tagtaatcaa ttacggggtc attagttcat agcccatata tggagttccg | 60 |
| cgttacataa cttacggtaa atggcccgcc tggctgaccg cccaacgacc cccgcccatt | 120 |
| gacgtcaata atgacgtatg ttcccatagt aacgccaata gggactttcc attgacgtca | 180 |
| atgggtggag tatttacggt aaactgccca cttggcagta catcaagtgt atcatatgcc | 240 |
| aagtacgccc cctattgacg tcaatgacgg taaatggccc gcctggcatt atgcccagta | 300 |
| catgacctta tgggactttc ctacttggca gtacatctac gtattagtca tcgctattac | 360 |
| catggtgatg cggttttggc agtacatcaa tgggcgtgga tagcggtttg actcacgggg | 420 |
| atttccaagt ctccacccca ttgacgtcaa tgggagtttg ttttggcacc aaaatcaacg | 480 |
| ggactttcca aaatgtcgta acaactccgc cccattgacg caaatgggcg gtaggcgtgt | 540 |
| acggtgggag gtctatataa gcagagctgg tttagtgaac cggcgccagt cctccgattg | 600 |
| actgagtcgc ccgggtaccc gtgtatccaa taaaccctct tgcagttgca tccgacttgt | 660 |
| ggtctcgctg ttccttggga gggtctcctc tgagtgattg actacccgtc agcggggggtc | 720 |
| tttcatttgg gggctcgtcc gggatcggga gaccctgcc cagggaccac cgacccacca | 780 |
| ccgggaggta agctggccag caacttatct gtgtctgtcc gattgtctag tgtctatgac | 840 |
| tgatttatg cgcctgcgtc ggtactagtt agctaactag ctctgtatct ggcggacccg | 900 |
| tggtggaact gacgagttcg gaacacccgg ccgcaaccct gggagacgtc ccagggactt | 960 |
| cgggggccgt ttttgtggcc cgacctgagt ccaaaaatcc cgatcgtttt ggactctttg | 1020 |
| gtgcacccc cttagaggag ggatatgtgg ttctggtagg agacgagaac ctaaaacagt | 1080 |
| tcccgcctcc gtctgaattt ttgctttcgg tttgggaccg aagccgcgcc gcgcgtcttg | 1140 |
| tctgctgcag catcgttctg tgttgtctct gtctgactgt gtttctgtat ttgtctgaaa | 1200 |
| atatgggcca gactgttacc actcccttaa gtttgacctt aggtcactgg aaagatgtcg | 1260 |
| agcggatcgc tcacaaccag tcggtagatg tcaagaagag acgttgggtt accttctgct | 1320 |
| ctgcagaatg gccaaccttt aacgtcggat ggccgcgaga cggcaccttt aaccgagacc | 1380 |
| tcatcaccca ggttaagatc aaggtctttt cacctggccc gcatggacac ccagaccagg | 1440 |
| tccctacat cgtgacctgg gaagccttgg cttttgaccc ccctccctgg gtcaagccct | 1500 |
| ttgtacaccc taagcctccg cctcctcttc ctccatccgc ccgtctctc cccttgaac | 1560 |
| ctcctcgttc gaccccgcct cgatcctccc tttatccagc cctcactcct tctctaggcg | 1620 |
| ccaaacctaa acctcaagtt ctttctgaca gtgggggggcc gctcatcgac ctacttacag | 1680 |

-continued

```
aagaccccc gccttatagg gacccaagac caccccttc cgacagggac ggaaatggtg    1740
gagaagcgac ccctgcggga gaggcaccgg acccctcccc aatggcatct cgcctacgtg    1800
ggagacggga gccccctgtg gccgactcca ctacctcgca ggcattcccc ctccgcgcag    1860
gaggaaacgg acagcttcaa tactggccgt tctcctcttc tgacctttac aactggaaaa    1920
ataataaccc ttcttttct gaagatccag gtaaactgac agctctgatc gagtctgtcc    1980
tcatcaccca tcagcccacc tgggacgact gtcagcagct gttggggact ctgctgaccg    2040
gagaagaaaa acaacgggtg ctcttagagg ctagaaaggc ggtgcggggc gatgatgggc    2100
gccccactca actgcccaat gaagtcgatg ccgcttttcc cctcgagcgc ccagactggg    2160
attacaccac ccaggcaggt aggaaccacc tagtccacta tcgccagttg ctcctagcgg    2220
gtctccaaaa cgcgggcaga agccccacca atttggccaa ggtaaaagga ataacacaag    2280
ggcccaatga gtctccctcg gccttcctag agagacttaa ggaagcctat cgcaggtaca    2340
ctccttatga ccctgaggac ccagggcaag aaactaatgt gtctatgtct ttcatttggc    2400
agtctgcccc agacattggg agaaagttag agaggttaga agatttaaaa aacaagacgc    2460
ttggagattt ggttagagag gcagaaaaga tctttaataa acgagaaacc ccggaagaaa    2520
gagaggaacg tatcaggaga gaaacagagg aaaaagaaga acgccgtagg acagaggatg    2580
agcagaaaga gaaagaaaga gatcgtagga gacatagaga gatgagcaag ctattggcca    2640
ctgtcgttag tggacagaaa caggatagac agggaggaga acgaaggagg tcccaactcg    2700
atcgcgacca gtgtgcctac tgcaaagaaa aggggcactg ggctaaagat tgtcccaaga    2760
aaccacgagg acctcgggga ccaagacccc agacctccct cctgacccta gatgactagg    2820
gaggtcaggg tcaggagccc cccctgaac ccaggataac cctcaaagtc ggggggcaac    2880
ccgtcacctt cctggtagat actggggccc aacactccgt gctgacccaa atcctggac    2940 ccctaagtga taagtctgcc tgggtccaag ggctactgg aggaaagcgg tatcgctgga    3000
ccacggatcg caaagtacat ctagctaccg gtaaggtcac ccactctttc ctccatgtac    3060
cagactgtcc ctatcctctg ttaggaagag atttgctgac taaactaaaa gcccaaatcc    3120
actttgaggg atcaggagcc caggttatgg gaccaatggg gcagcccctg caagtgttga    3180
ccctaaatat agaagatgag tatcggctac atgagacctc aaaagagcca gatgtttctc    3240
tagggtccac atggctgtct gattttcctc aggcctgggc ggaaaccggg gcatgggac    3300 tggcagttcg ccaagctcct ctgatcatac ctctgaaagc aacctctacc cccgtgtcca    3360
taaaacaata ccccatgtca caagaagcca gactggggat caagcccac atacagagac    3420 tgttggacca gggaatactg gtaccctgcc agtcccctg gaacacgccc ctgctacccg    3480
ttaagaaacc agggactaat gattataggc ctgtccagga tctgagagaa gtcaacaagc    3540
gggtggaaga catccacccc accgtgccca accctacaa cctcttgagc gggctcccac    3600
cgtcccacca gtggtacact gtgcttgatt taaaggatgc ctttttctgc ctgagactcc    3660
accccaccag tcagcctctc ttcgcctttg agtggagaga tccagagatg ggaatctcag    3720
gacaattgac ctggaccaga ctcccacagg gtttcaaaaa cagtcccacc ctgtttgatg    3780
aggcactgca cagagaccta gcagacttcc ggatccagca cccagacttg atcctgctac    3840
agtacgtgga tgacttactg ctggccgcca cttctgagct agactgccaa caaggtactc    3900
gggccctgtt acaaaccta gggaacctcg ggtatcgggc ctcggccaag aaagcccaaa    3960
tttgccagaa acaggtcaag tatctggggt atcttctaaa agagggtcag agatggctga    4020
```

```
ctgaggccag aaaagagact gtgatggggc agcctactcc gaagacccct cgacaactaa      4080
gggagttcct agggacggca ggcttctgtc gcctctggat ccctgggttt gcagaaatgg      4140
cagccccctt gtaccctctc accaaaacgg ggactctgtt taattggggc ccagaccaac      4200
aaaaggccta tcaagaaatc aagcaagctc ttctaactgc cccagccctg gggttgccag      4260
atttgactaa gcccttttgaa ctctttgtcg acgagaagca gggctacgcc aaaggtgtcc      4320
taacgcaaaa actgggacct tggcgtcggc cggtggccta cctgtccaaa agctagacc      4380 cagtagcagc tgggtggccc ccttgcctac ggatggtagc agccattgcc gtactgacaa      4440
aggatgcagg caagctaacc atgggacagc cactagtcat tctggccccc catgcagtag      4500
aggcactagt caaacaaccc cccgaccgct ggctttccaa cgcccggatg actcactatc      4560
aggccttgct tttggacacg gaccgggtcc agttcggacc ggtggtagcc ctgaacccgg      4620
ctacgctgct cccactgcct gaggaagggc tgcaacacaa ctgccttgat atcctggccg      4680
aagcccacgg aacccgaccc gacctaacgg accagccgct cccagacgcc gaccacacct      4740
ggtacacgga tggaagcagt ctcttacaag agggacagcg taaggcggga gctgcggtga      4800
ccaccgagac cgaggtaatc tgggctaaag ccctgccagc cgggacatcc gctcagcggg      4860
ctgaactgat agcactcacc caggccctaa agatggcaga aggtaagaag ctaaatgttt      4920
atactgatag ccgttatgct tttgctactg cccatatcca tggagaaata tacagaaggc      4980
gtgggttgct cacatcagaa ggcaaagaga tcaaaaataa agacgagatc ttggccctac      5040
taaaagccct ctttctgccc aaaagactta gcataatcca ttgtccagga catcaaaagg      5100
gacacagcgc cgaggctaga ggcaaccgga tggctgacca gcggcccga aaggcagcca      5160 tcacagagac tccagacacc tctaccctcc tcatagaaaa ttcatcaccc tacacctcag      5220
aacattttca ttacacagtg actgatataa aggacctaac caagttgggg gccatttatg      5280
ataaaacaaa gaagtattgg gtctaccaag gaaaacctgt gatgcctgac cagtttactt      5340
ttgaattatt agactttctt catcagctga ctcacctcag cttctcaaaa atgaaggctc      5400
tcctagagag aagccacagt ccctactaca tgctgaaccg ggatcgaaca ctcaaaaata      5460
tcactgagac ctgcaaagct tgtgcacaag tcaacgccag caagtctgcc gttaaacagg      5520
gaactagggt ccgcgggcat cggcccggca ctcattggga gatcgatttc accgagataa      5580
agcccggatt gtatggctat aaatatcttc tagtttttat agatacctttt tctggctgga      5640 tagaagcctt cccaaccaag aaagaaaccg ccaaggtcgt aaccaagaag ctactagagg      5700
agatcttccc caggttcggc atgcctcagg tattgggaac tgacaatggg cctgccttcg      5760
tctccaaggt gagtcagaca gtggccgatc tgttggggat tgattggaaa ttacattgtg      5820
catacagacc ccaaagctca ggccaggtag aaagaatgaa tagaaccatc aaggagactt      5880
taactaaatt aacgcttgca actggctcta gagactgggt gctcctactc cccttagccc      5940
tgtaccgagc ccgcaacacg ccgggccccc atgcctcac cccatatgag atcttatatg      6000
gggcaccccc gccccttgta aacttccctg accctgacat gacaagagtt actaacagcc      6060
cctctctcca agctcactta caggctctct acttagtcca gcacgaagtc tggagacctc      6120
tggcggcagc ctaccaagaa caactggacc gaccggtggt acctcaccct taccgagtcg      6180
gcgacacagt gtgggtccgc cgacaccaga ctaagaacct agaacctcgc tggaaaggac      6240
cttacacagt cctgctgacc accccaccg cccctcaaagt agacggcatc gcagcttgga      6300
tacacgccgc ccacgtgaag gctgccgacc ccggggtgg accatcctct agactgacat      6360
ggcgcgttca acgctctcaa aaccccctca agataagatt aacccgtgga agcccttaat      6420
```

-continued

```
agtcatggga gtcctgttag gagtagggat ggcagagagc ccccatcagg tctttaatgt    6480
aacctggaga gtcaccaacc tgatgactgg gcgtaccgcc aatgccacct ccctcctggg    6540
aactgtacaa gatgccttcc caaaattata ttttgatcta tgtgatctgg tcggagagga    6600
gtgggaccct tcagaccagg aaccgtatgt cgggtatggc tgcaagtacc ccgcaggag     6660 acagcggacc cggacttttg acttttacgt gtgccctggg cataccgtaa agtcggggtg    6720
tgggggacca ggagagggct actgtggtaa atggggtgt gaaaccaccg gacaggctta     6780
ctggaagccc acatcatcgt gggacctaat ctcccttaag cgcggtaaca ccccctggga    6840
cacgggatgc tctaaagttg cctgtggccc ctgctacgac ctctccaaag tatccaattc    6900
cttccaaggg gctactcgag ggggcagatg caaccctcta gtcctagaat tcactgatgc    6960
aggaaaaaag gctaactggg acgggcccaa atcgtgggga ctgagactgt accgacagg     7020 aacagatcct attaccatgt tctccctgac ccggcaggtc cttaatgtgg gaccccgagt    7080
ccccataggg cccaacccag tattacccga ccaaagactc ccttcctcac caatagagat    7140
tgtaccggct ccacagccac ctagcccct caataccagt taccccctt ccactaccag      7200 tacaccctca acctcccta caagtccaag tgtcccacag ccacccccag gaactggaga     7260
tagactacta gctctagtca aaggagccta tcaggcgctt aacctcacca atcccgacaa    7320
gacccaagaa tgttggctgt gcttagtgtc gggaccctcct tattacgaag gagtagcggt   7380
cgtgggcact tataccaatc attccaccgc tccggccaac tgtacggcca cttcccaaca    7440
taagcttacc ctatctgaag tgacaggaca gggcctatgc atggggcag tacctaaaac     7500 tcaccaggcc ttatgtaaca ccacccaaag cgccggctca ggatcctact accttgcagc    7560
acccgccgga acaatgtggg cttgcagcac tggattgact ccctgcttgt ccaccacggt    7620
gctcaatcta accacagatt attgtgtatt agttgaactc tggcccagag taatttacca    7680
ctcccccgat tatatgtatg tcagcttga acagcgtacc aaatataaaa gagagccagt     7740
atcattgacc ctggcccttc tactaggagg attaaccatg ggagggattg cagctggaat    7800
agggacgggg accactgcct taattaaaac ccagcagttt gagcagcttc atgccgctat    7860
ccagacagac ctcaacgaag tcgaaaagtc aattaccaac ctagaaaagt cactgacctc    7920
gttgtctgaa gtagtcctac agaaccgcag aggcctagat ttgctattcc taaaggaggg    7980
aggtctctgc gcagccctaa aagaagatg ttgtttttat gcagaccaca cggggctagt    8040
gagagacagc atggccaaat taagagaaag gcttaatcag agacaaaaac tatttgagac    8100
aggccaagga tggttcgaag ggtgttttaa tagatccccc tggttaccca ccttaatctc    8160
caccatcatg ggacctctaa tagtactctt actgatctta ctctttggac cttgcattct    8220
caatcgattg tgtccaatttg ttaaagacag gatctcagtg gtccaggctc tggttttgac   8280
tcagcaatat caccagctaa aacccataga gtacgagcca tgaacgcgtt actggccgaa    8340
gccgcttgga ataaggccgg tgtgcgtttg tctatatgtt attttccacc atattgccgt    8400
cttttggcaa tgtgagggcc cggaaacctg gccctgtctt cttgacgagc attcctaggg    8460
gtctttcccc tctcgccaaa ggaatgcaag gtctgttgaa tgtcgtgaag gaagcagttc    8520
ctctggaagc ttcttgaaga caacaacgt ctgtagcgac cctttgcagg cagcggaacc     8580
ccccacctgg cgacaggtgc ctctgcggcc aaaagccacg tgtataagat acacctgcaa    8640
aggcggcaca accccagtgc cacgttgtga gttggatagt tgtggaaaga gtcaaatggc    8700
tctcctcaag cgtattcaac aaggggctga aggatgccca gaaggtaccc cattgtatgg    8760
```

-continued

```
gatctgatct ggggcctcgg tgcacatgct ttacatgtgt ttagtcgagg ttaaaaaaac    8820
gtctaggccc cccgaaccac ggggacgtgg ttttcctttg aaaaacacga ttataaatgg    8880
tgaccggcgg catggcctcc aagtgggatc aaaagggcat ggatatcgct tacgaggagg    8940
ccctgctggg ctacaaggag ggcggcgtgc ctatcggcgg ctgtctgatc aacaacaagg    9000
acggcagtgt gctgggcagg ggccacaaca tgaggttcca gaagggctcc gccaccctgc    9060
acggcgagat ctccaccctg gagaactgtg gcaggctgga gggcaaggtg tacaaggaca    9120
ccaccctgta caccaccctg tccccttgtg acatgtgtac cggcgctatc atcatgtacg    9180
gcatccctag gtgtgtgatc ggcgagaacg tgaacttcaa gtccaagggc gagaagtacc    9240
tgcaaaccag gggccacgag gtggtggttg ttgacgatga gaggtgtaag aagctgatga    9300
agcagttcat cgacgagagg cctcaggact ggttcgagga tatcggcgag taagcggccg    9360
cagataaaat aaaagatttt atttagtctc cagaaaaagg ggggaatgaa agaccccacc    9420
tgtaggtttg gcaagctagc ttaagtaacg ccattttgca aggcatggaa aaatacataa    9480
ctgagaatag agaagttcag atcaaggtca ggaacagatg gaacagctga atatgggcca    9540
aacaggatat ctgtggtaag cagttcctgc cccggctcag gccaagaac agatggaaca    9600
gctgaatatg ggccaaacag gatatctgtg gtaagcagtt cctgccccgg ctcagggcca    9660
agaacagatg gtccccagat gcggtccagc cctcagcagt ttctagagaa ccatcagatg    9720
tttccagggt gccccaagga cctgaaatga ccctgtgcct tatttgaact aaccaatcag    9780
ttcgcttctc gcttctgttc gcgcgcttct gctccccgag ctcaataaaa gagcccacaa    9840
cccctcactc ggggcgccag tcctccgatt gactgagtcg cccgggtacc cgtgtatcca    9900
ataaaccctc ttgcagttgc atccgacttg tggtctcgct gttccttggg agggtctcct    9960
ctgagtgatt gactacccgt cagcgggggt ctttcattac atgtgagcaa aaggccagca   10020
aaaggccagg aaccgtaaaa aggccgcgtt gctggcgttt ttccataggc tccgcccccc   10080
tgacgagcat cacaaaaatc gacgctcaag tcagaggtgg cgaaacccga caggactata   10140
aagataccag gcgtttcccc ctggaagctc cctcgtgcgc tctcctgttc cgaccctgcc   10200
gcttaccgga tacctgtccg cctttctccc ttcgggaagc gtggcgcttt ctcatagctc   10260
acgctgtagg tatctcagtt cggtgtaggt cgttcgctcc aagctgggct gtgtgcacga   10320
accccccgtt cagcccgacc gctgcgcctt atccggtaac tatcgtcttg agtccaaccc   10380
ggtaagacac gacttatcgc cactggcagc agccactggt aacaggatta gcagagcgag   10440
gtatgtaggc ggtgctacag agttcttgaa gtggtggcct aactacggct acactagaag   10500
gacagtattt ggtatctgcg ctctgctgaa gccagttacc ttcggaaaaa gagttggtag   10560
ctcttgatcc ggcaaacaaa ccaccgctgg tagcggtggt ttttttgttt gcaagcagca   10620
gattacgcgc agaaaaaaag gatctcaaga agatcctttg atcttttcta cggggtctga   10680
cgctcagtgg aacgaaaact cacgttaagg gattttggtc atgagattat caaaaaggat   10740
cttcacctag atccttttaa attaaaaatg aagttttaaa tcaatctaaa gtatatatga   10800
gtaaacttgg tctgacagtt accaatgctt aatcagtgag gcacctatct cagcgatctg   10860
tctatttcgt tcatccatag ttgcctgact ccccgtcgtg tagataacta cgatacggga   10920
gggcttacca tctggcccca gtgctgcaat gataccgcga acccacgct caccggctcc   10980
agatttatca gcaataaacc agccagccgg aagggccgag cgcagaagtg gtcctgcaac   11040
tttatccgcc tccatccagt ctattaattg ttgccgggaa gctagagtaa gtagttcgcc   11100
agttaatagt ttgcgcaacg ttgttgccat tgctgcaggc atcgtggtgt cacgctcgtc   11160
```

```
gtttggtatg gcttcattca gctccggttc ccaacgatca aggcgagtta catgatcccc    11220
catgttgtgc aaaaaagcgg ttagctcctt cggtcctccg atcgttgtca gaagtaagtt    11280
ggccgcagtg ttatcactca tggttatggc agcactgcat aattctctta ctgtcatgcc    11340
atccgtaaga tgcttttctg tgactggtga gtactcaacc aagtcattct gagaatagtg    11400
tatgcggcga ccgagttgct cttgcccggc gtcaacacgg ataataccg cgccacatag     11460 cagaacttta aaagtgctca tcattggaaa acgttcttcg gggcgaaaac tctcaaggat    11520
cttaccgctg ttgagatcca gttcgatgta acccactcgt gcacccaact gatcttcagc    11580
atcttttact ttcaccagcg tttctgggtg agcaaaaaca ggaaggcaaa atgccgcaaa    11640
aaagggaata agggcgacac ggaaatgttg aatactcata ctcttccttt ttcaatatta    11700
ttgaagcatt tatcagggtt attgtctcat gagcggatac atatttgaat gtatttagaa    11760
aaataaacaa ataggggttc cgcgcacatt tccccgaaaa gtgccacctg acgtctaaga    11820
aaccattatt atcatgacat taacctataa aaataggcgt atcacgaggc cctttcgtct    11880
tcaagaattc cat                                                       11893
```

<210> SEQ ID NO 26
<211> LENGTH: 7090
<212> TYPE: DNA
<213> ORGANISM: Artificial Sequence
<220> FEATURE:
<223> OTHER INFORMATION: Partial-fragmented Sequence of MoMLV (NCBI
      ref. NC_001501.1)

<400> SEQUENCE: 26

```
acagttcccg cctccgtctg aattttgct ttcggtttgg gaccgaagcc gcgccgcgcg      60
tcttgtctgc tgcagcatcg ttctgtgttg tctctgtctg actgtgtttc tgtatttgtc    120
tgagaatatg ggccagactg ttaccactcc cttaagtttg accttaggtc actggaaaga    180
tgtcgagcgg atcgctcaca accagtcggt agatgtcaag aagagacgtt gggttacctt    240
ctgctctgca gaatggccaa cctttaacgt cggatggccg cgagacggca cctttaaccg    300
agacctcatc acccaggtta agatcaaggt cttttcacct ggcccgcatg gacacccaga    360
ccaggtcccc tacatcgtga cctgggaagc cttggctttt gacccccctc cctgggtcaa    420
gccctttgta caccctaagc ctccgcctcc tcttcctcca tccgcccgt ctctccccct     480 tgaacctcct cgttcgaccc cgcctcgatc ctcccttat ccagccctca ctccttctct     540
aggcgccaaa cctaaacctc aagttctttt gacagtggg gggccgctca tcgacctact    600
tacagaagac ccccgcctt atagggaccc aagaccaccc cttccgaca gggacggaaa     660 tggtggagaa cgaccccctg cgggagaggc accggacccc tccccaatgg catctcgcct    720
acgtgggaga cgggagcccc ctgtggccga ctccactacc tcgcaggcat tccccctccg    780
cgcaggagga aacggacagc ttcaatactg gccgttctcc tcttctgacc tttacaactg    840
gaaaaataat aaccccttctt tttctgaaga tccaggtaaa ctgacagctc tgatcgagtc    900
tgttctcatc acccatcagc ccacctggga cgactgtcag cagctgttgg ggactctgct    960
gaccggagaa gaaaaacaac gggtgctctt agaggctaga aaggcggtgc ggggcgatga    1020
tgggcgcccc actcaactgc ccaatgaagt cgatgccgct tttcccctcg agcgcccaga    1080
ctgggattac accacccagg caggtaggaa ccacctagtc cactatcgcc agttgctcct    1140
agcgggtctc caaaacgcgg gcagaagccc caccaatttg gccaaggtaa aggaataac    1200 acaagggccc aatgagtctc cctcggcctt cctagagaga cttaaggaag cctatcgcag    1260
```

```
gtacactcct tatgaccctg aggacccagg gcaagaaact aatgtgtcta tgtctttcat    1320
ttggcagtct gccccagaca ttgggagaaa gttagagagg ttagaagatt taaaaaacaa    1380
gacgcttgga gatttggtta gagaggcaga aaagatcttt aataaacgag aaaccccgga    1440
agaaagagag gaacgtatca ggagagaaac agaggaaaaa gaagaacgcc gtaggacaga    1500
ggatgagcag aaagagaaag aaagagatcg taggagacat agagagatga gcaagctatt    1560
ggccactgtc gttagtggac agaaacagga tagacaggga ggagaacgaa ggaggtccca    1620
actcgatcgc gaccagtgtg cctactgcaa agaaagggg cactgggcta agattgtcc      1680 caagaaacca cgaggacctc ggggaccaag accccagacc tccctcctga ccctagatga    1740
ctagggaggt cagggtcagg agcccccccc tgaacccagg ataaccctca aagtcggggg    1800
gcaacccgtc accttcctgg tagatactgg ggcccaacac tccgtgctga cccaaaatcc    1860
tggaccccta agtgataagt ctgcctgggt ccaaggggct actggaggaa agcggtatcg    1920
ctggaccacg gatcgcaaag tacatctagc taccggtaag gtcacccact ctttcctcca    1980
tgtaccagac tgtccctatc ctctgttagg aagagatttg ctgactaaac taaaagccca    2040
aatccacttt gagggatcag gagctcaggt tatgggacca atggggcagc ccctgcaagt    2100
gttgacccta aatatagaag atgagcatcg gctacatgag acctcaaaag agccagatgt    2160
ttctctaggg tccacatggc tgtctgattt cctcaggcc tgggcggaaa ccggggggcat     2220 gggactggca gttcgccaag ctcctctgat catacctctg aaagcaacct ctaccccgt     2280 gtccataaaa caatacccca tgtcacaaga agccagactg gggatcaagc cccacataca    2340
gagactgttg gaccagggaa tactggtacc ctgccagtcc cctggaaaca cgcccctgct    2400
acccgttaag aaaccaggga ctaatgatta taggcctgtc caggatctga gagaagtcaa    2460
caagcgggtg gaagacatcc accccaccgt gcccaaccct acaacctct gagcgggct      2520 cccaccgtcc caccagtggt acactgtgct tgatttaaag gatgcctttt tctgcctgag    2580
actccacccc accagtcagc ctctcttcgc cttttgagtgg agagatccag agatgggaat    2640
ctcaggacaa ttgacctgga ccagactccc acagggttc aaaaacagtc ccaccctgtt     2700
tgatgaggca ctgcacagag acctagcaga cttccggatc cagcacccag acttgatcct    2760
gctacagtac gtggatgact tactgctggc cgccacttct gagctagact gccaacaagg    2820
tactcgggcc ctgttacaaa ccctagggaa cctcgggtat cggcctcgg ccaagaaagc     2880 ccaaatttgc cagaaacagg tcaagtatct ggggtatctt ctaaaagagg gtcagagatg    2940
gctgactgag gccagaaaag agactgtgat ggggcagcct actccgaaga cccctcgaca    3000
actaagggag ttcctaggga cggcaggctt ctgtcgcctc tggatccctg ggtttgcaga    3060
aatggcagcc cccttgtacc ctctcaccaa aacgggggact ctgtttaatt ggggcccaga    3120
ccaacaaaag gcctatcaag aaatcaagca agctcttcta actgccccag ccctggggtt    3180
gccagatttg actaagccct ttgaactctt tgtcgacgag aagcagggct acgccaaagg    3240
tgtcctaacg caaaaactgg accttggccg tcggccggtg gcctacctgt ccaaaaagct    3300
agacccagta gcagctgggt gggccccctt cctacggatg gtagcagcca ttgccgtact    3360
gacaaaggat gcaggcaagc taaccatggg acagccacta gtcattctgg cccccatgc     3420 agtagaggca ctagtcaaac aaccccccga ccgctggctt tccaacgccc ggatgactca    3480
ctatcaggcc ttgctttgg acacggaccg ggtccagttc ggaccggtgg tagccctgaa     3540
cccggctacg ctgctcccac tgcctgagga agggctgcaa cacaactgcc ttgatatcct    3600
```

```
ggccgaagcc cacggaaccc gacccgacct aacggaccag ccgctcccag acgccgacca    3660
cacctggtac acggatggaa gcagtctctt acaagaggga cagcgtaagg cgggagctgc    3720
ggtgaccacc gagaccgagg taatctgggc taaagccctg ccagccggga catccgctca    3780
gcgggctgaa ctgatagcac tcacccaggc cctaaagatg gcagaaggta agaagctaaa    3840
tgtttatact gatagccgtt atgcttttgc tactgcccat atccatggag aaatatacag    3900
aaggcgtggg ttgctcacat cagaaggcaa agagatcaaa aataaagacg agatcttggc    3960
cctactaaaa gccctctttc tgcccaaaag acttagcata atccattgtc caggacatca    4020
aaagggacac agcgccgagg ctagaggcaa ccggatggct gaccaagcgg cccgaaaggc    4080
agccatcaca gagactccag acacctctac cctcctcata gaaaattcat caccctacac    4140
ctcagaacat tttcattaca cagtgactga tataaaggac ctaaccaagt tgggggccat    4200
ttatgataaa acaaagaagt attgggtcta ccaaggaaaa cctgtgatgc ctgaccagtt    4260 tactttgaa ttattagact ttcttcatca gctgactcac ctcagcttct caaaaatgaa    4320
ggctctccta gagagaagcc acagtcccta ctacatgctg aaccgggatc gaacactcaa    4380
aaatatcact gagacctgca aagcttgtgc acaagtcaac gccagcaagt ctgccgttaa    4440
acagggaact agggtccgcg ggcatcggcc ggcactcat tgggagatcg atttcaccga    4500
gataaagccc ggattgtatg ctataaata tcttctagtt tttatagata cctttttctgg    4560 ctggatagaa gccttcccaa ccaagaaaga aaccgccaag gtcgtaacca agaagctact    4620
agaggagatc ttccccaggt tcggcatgcc tcaggtattg ggaactgaca atgggcctgc    4680
cttcgtctcc aaggtgagtc agacagtggc cgatctgttg gggattgatt ggaaattaca    4740
ttgtgcatac agaccccaaa gctcaggcca ggtagaaaga atgaatagaa ccatcaagga    4800
gactttaact aaaattaacg cttgcaactg gctctagagac tgggtgctcc tactcccctt    4860
agccctgtac cgagcccgca cacgccgggg ccccatggc ctcacccat atgagatctt    4920 atatggggca cccccgcccc ttgtaaactt ccctgacccct gacatgacaa gagttactaa    4980
cagcccctct ctccaagctc acttacaggc tctctactta gtccagcacg aagtctggag    5040
acctctggcg gcagcctacc aagaacaact ggaccgaccg gtggtacctc acccttaccg    5100
agtcggcgac acagtgtggg tccgccgaca ccagactaag aacctagaac ctcgctggaa    5160
aggaccttac acagtcctgc tgaccacccc caccgccctc aaagtagacg gcatcgcagc    5220
ttggatacac gccgccacg tgaaggctgc cgacgggaac ggaaaatagg ctgctaaact    5280
tagtagacgg agcctaccaa gccctcaacc tcaccagtcc tgacaaaacc caagagtgct    5340
ggttgtgtct agtagcggga ccccctact acgaaggggt tgccgtcctg ggtacctact    5400
ccaaccatac ctctgctcca gccaactgct ccgtggcctc ccaacacaag ttgaccctgt    5460
ccgaagtgac cggacaggga ctctgcatag gagcagttcc caaaacacat caggccctat    5520
gtaataccac ccagacaagc agtcgagggt cctattatct agttgcccct acaggtacca    5580
tgtgggcttg tagtaccggg cttactccat gcatctccac caccatactg aaccttacca    5640
ctgattattg tgttcttgtc gaactctggc caagagtcac ctatcattcc cccagctatg    5700
tttacggcct gtttgagaga tccaaccgac acaaaagaga accggtgtcg ttaaccctgg    5760
ccctattatt gggtggacta accatggggg gaattgccgc tggaatagga acagggacta    5820
ctgctctaat ggccactcag caattccagc agctccaagc cgcagtacag gatgatctca    5880
gggaggttga aaaatcaatc tctaacctag aaaagtctct cacttccctg tctgaagttg    5940
tcctacagaa tcgaagggc ctagacttgt tatttctaaa agaaggaggg ctgtgtgctg    6000
```

```
ctctaaaaga agaatgttgc ttctatgcgg accacacagg actagtgaga gacagcatgg    6060
ccaaattgag agagaggctt aatcagagac agaaactgtt tgagtcaact caaggatggt    6120
ttgagggact gtttaacaga tccccttggt ttaccacctt gatatctacc attatgggac    6180
ccctcattgt actcctaatg attttgctct tcggaccctg cattcttaat cgattagtcc    6240
aatttgttaa agacaggata tcagtggtcc aggctctagt tttgactcaa caatatcacc    6300
agctgaagcc tatagagtac gagccataga taaaataaaa gattttattt agtctccaga    6360
aaaagggggg aatgaaagac cccacctgta ggtttggcaa gctagcttaa gtaacgccat    6420
tttgcaaggc atggaaaaat acataactga aatagagaa gttcagatca aggtcaggaa    6480
cagatggaac agctgaatat gggccaaaca ggatatctgt ggtaagcagt tcctgccccg    6540
gctcagggcc aagaacagat gggcgccagt cctccgattg actgagtcgc ccgggtaccc    6600
gtgtatccaa taaaccctct tgcagttgca tccgacttgt ggtctcgctg ttccttggga    6660
gggtctcctc tgagtgattg actacccgtc agcggggtc tttcatttgg gggctcgtcc    6720
gggatcggga gacccctgcc cagggaccac cgacccacca ccgggaggta agctggccgg    6780
gccaaacagg atatctgtgg taagcagttc ctgccccggc tcagggccaa gaacagatgg    6840
tccccagatg cggtccagcc ctcagcagtt tctagagaac catcagatgt ttccagggtg    6900
ccccaaggac ctgaaatgac cctgtgcctt atttgaacta accaatcagt tcgcttctcg    6960
cttctgttcg cgcgcttctg ctccccgagc tcaataaaag agcccacaac ccctcactcg    7020
gggcgccagt cctccgattg actgagtcgc ccgggtaccc gtgtatccaa taaaccctct    7080
tgcagttgca                                                           7090
```

<210> SEQ ID NO 27
<211> LENGTH: 7107
<212> TYPE: DNA
<213> ORGANISM: Artificial Sequence
<220> FEATURE:
<223> OTHER INFORMATION: Patial/fragmented sequence of XMRV (VP62, NCBI
   ref. NC_007815.1)

<400> SEQUENCE: 27

```
acacttcccg cccccgtctg aattttttgct ttcggtttta cgccgaaacc gcgccgcgcg    60
tctgatttgt tttgttgttc ttctgttctt cgttagtttt cttctgtctt taagtgttct   120
cgagatcatg ggacagaccg taactacccc tctgagtcta accttgcagc actggggaga   180
tgtccagcgc attgcatcca accagtctgt ggatgtcaag aagaggcgct gggttacctt   240
ctgttccgcc gaatggccaa cttttcaatgt aggatggcct caggatggta cttttaattt   300
aggtgttatc tctcaggtca agtctagagt gtttttgtcct ggtccccacg gacacccgga   360
tcaggtccca tatatcgtca cctgggaggc acttgcctat gacccccctc cgtgggtcaa   420
accgttttgtc tctcctaaac cccctccttt accgacagct cccgtcctcc cgcccggtcc   480
ttctcgcgcaa cctccgtccc gatctgccct ttaccctgcc cttaccccct ctataaagtc   540
caaacctcct aagccccagg ttctccctga tagcggcgga cctctcattg accttctcac    600
agaggatccc ccgccgtacg gagcacaacc ttcctcctct gccagggaga acaatgaaga   660
agaggcggcc accacctccg aggtttcccc cccttctccc atggtgtctc gactgcgggg    720
aaggagagac cctccccgcag cggactccac cacctcccag gcattccac tccgcatggg    780
gggagatggc cagcttcagt actggccgtt ttcctcctct gatttatata attggaaaaa   840
taataaccct tcctttttctg aagatccagg taaattgacg gccttgattg agtccgtcct   900
```

```
catcacccac cagcccacct gggacgactg tcagcagttg ttggggaccc tgctgaccgg    960
agaagaaaag cagcgggtgc tcctagaggc tagaaaggca gtccggggca atgatggacg   1020
ccccactcag ttgcctaatg aagtcaatgc tgcttttccc cttgagcgcc ccgattggga   1080
ttacaccact acagaaggta ggaaccacct agtcctctac cgccagttgc tcttagcggg   1140
tctccaaaac gcgggcagga gccccaccaa tttggccaag gtaaaaggga taacccaggg   1200
acctaatgag tctccctcag ccttttaga gagactcaag gaggcctatc gcaggtacac    1260
tccttatgac cctgaggacc cagggcaaga aaccaatgtg tccatgtcat tcatctggca   1320
gtctgccccg gatatcggac gaaagttaga gcggttagaa gatttaaaga gcaagacctt   1380
aggagactta gtgagggaag ctgaaaagat ctttaataag cgagaaaccc cggaagaaag   1440
agaggaacgt atcaggagag aaatagagga aaagaagaa cgccgtaggg cagaggatga    1500
gcagagagag agagaaaggg accgcagaag acatagagag atgagcaagc tcttggccac   1560
tgtagttatt ggtcagagac aggatagaca ggggggagag cggaggaggc ccaacttga    1620 taaggaccaa tgcgcctact gcaaagaaaa gggacactgg gctaaggact gcccaaagaa   1680
gccacgaggg ccccgaggac cgaggcccca gacctccctc ctgaccttag gtgactaggg   1740
aggtcagggt caggagcccc ccctgaacc caggataacc ctcaaagtcg ggggcaacc    1800 cgtcaccttc ctggtagata ctggggccca acactccgtg ctgacccaaa atcctggacc   1860
cctaagtgac aagtctgcct gggtccaagg ggctactgga ggaaagcggt atcgctggac   1920
cacggatcgc aaagtacatc tggctaccgg taaggtcacc cactctttcc tccatgtacc   1980
agactgcccc tatcctctgc taggaagaga cttgctgact aaactaaaag cccaaatcca   2040
ctttgaggga tcaggagctc aggttgtggg accgatggga cagcccctgc aagtgctgac   2100
agtaaacata gaagatgagt attggctaca tgataccagg aaagagccag atgttcctct   2160
agggtccaca tggctttctg atttccttca ggcctgggcg gaaaccgggg gcatgggact   2220
ggcagttcgc caagctcctc tgatcatacc tctgaaggca acctctaccc ccgtgtccat   2280
aaaacaatac cccatgtcac aagaagccag actggggatc aagccccaca tacagaggct   2340
gttggaccag ggaatactgg taccctgcca gtccccctgg aacacgcccc tgctacccgt   2400
taagaaacca gggactaatg attataggcc tgtccaggat ctgagagaag tcaacaagcg   2460
ggtggaagac atccacccca ccgtgcccaa cccttacaac ctcttgagcg ggctcccacc   2520
gtcccaccag tggtacactg tgcttgattt aaaggatgcc ttttctgcc tgagactcca    2580 ccccaccagt cagcctctct tcgcctttga gtggagagat ccagagatgg gaatctcagg   2640
acaactgacc tggaccagac tcccacaggg tttcaaaaac agtcccaccc tgtttgatga   2700
ggcactgcac agagacctag cagatttccg gatccagcac ccagcttga tcctgctaca    2760 gtacgtggat gacttactgc tggccgccac ttctgagcaa gactgccaac gaggtactcg   2820
ggccctatta caaaccctag gaacctcgg gtatcgggcc tcggcaaga aagcccaaat   2880 ttgccagaaa caggtcaagt atctggggta tctcctaaaa gagggacaga gatggctgac   2940
tgaggccaga aaagactg tgatggggca gcccactccg aagaccctc gacaactaag    3000 ggagttccta gggacggcag gcttctgtcg cctctggatc cctgggtttg cagaaatggc   3060 agccccttg taccctctta ccaaaacggg gactctgttt aattggggcc cagaccagca    3120
aaaggcctat caagaaatca aacaggctct tctaactgcc cccgccctgg gattgccaga   3180
tttgactaag ccctttgaac tctttgtcga cgagaagcag ggctacgcca aggcgtcct    3240
```

```
aacgcaaaaa ctgggacctt ggcgtcggcc tgtggcctac ctgtccaaaa agctagaccc      3300
agtggcagct gggtggcccc cttgcctacg gatggtagca gccattgccg ttctgacaaa      3360
aaatgcaggc aagctaacta tgggacagcc gctagtcatt ctggcccccc atgcggtaga      3420
agcactggtc aaacaacccc ctgaccgttg gctatccaat gcccgcatga cccactatca      3480
ggcaatgctc ctggatacag accgggttca gttcggaccg gtggtggccc tcaacccggc      3540
caccctgctc cccctaccgg aaaaggaagc cccccatgac tgcctcgaga tcttggctga      3600
gacgcacgga accagaccgg acctcacgga ccagcccatc ccagacgctg attacacttg      3660
gtacacagat ggaagcagct tcctacaaga aggacaacgg agagctggag cagcggtgac      3720
tactgagacc gaggtaatct gggcgagggc tctgccggct ggaacatccg cccaacgagc      3780
cgaactgata gcactcaccc aagccttaaa gatggcagaa ggtaagaagc taatgtttta      3840
cactgatagc cgctatgcct tcgccacggc ccatgtccat ggagaaatat ataggaggcg      3900
agggttgctg acctcagaag gcagagaaat taaaaacaag aacgagatct tggccttgct      3960
aaaagctctc tttctgccca aacgactag tataattcac tgtccaggac atcaaaaagg      4020
aaacagtgct gaggccagag gcaaccgtat ggcagatcaa gcagcccgag aggcagccat      4080
gaaggcagtt ctagaaacct ctacactcct catagaggac tcaaccccgt atacgcctcc      4140
ccatttccat tacaccgaaa cagatctcaa aagactacgg gaactgggag ccacctacaa      4200
tcagacaaaa ggatattggg tcctacaagg caaacctgtg atgcccgatc agtccgtgtt      4260
tgaactgtta gactccctac acagactcac ccatctgagc cctcaaaaga tgaaggcact      4320
cctcgacaga gaagaaagcc cctactacat gttaaaccgg gacagaacta tccagtatgt      4380
gactgagacc tgcaccgcct gtgcccaagt aaatgccagc aaagccaaaa ttggggcagg      4440
ggtgcgagta cgcggacatc ggccaggcac ccattgggaa gttgatttca cggaagtaaa      4500
gccaggactg tatgggtaca agtacctcct agtgtttgta gacaccttct ctggctgggt      4560
agaggcattc ccgaccaagc gggaaactgc caaggtcgtg tccaaaaagc tgttagaaga      4620
cattttccg agatttggaa tgccgcaggt attgggatct gataacgggc ctgccttcgc      4680
ctcccaggta agtcagtcag tggccgattt actggggatc gattggaagt tacattgtgc      4740
ttatagaccc cagagttcag gacaggtaga aagaatgaat agaacaatta aggagacttt      4800
gaccaaatta acgcttgcat ctggcactag agactgggta ctcctactcc ccttagccct      4860
ctaccgagcc cggaatactc cgggcccca cggactgact ccgtatgaaa ttctgtatgg      4920
ggcaccccg ccccttgtca attttcatga tcctgaaatg tcaaagttaa ctaatagtcc      4980
ctctctccaa gctcacttac aggccctcca agcagtacaa caagaggtct ggaagccgct      5040
ggccgctgct tatcaggacc agctagatca gccagtgata ccacacccct tccgtgtcgg      5100
tgacgccgtg tgggtacgcc ggcaccagac taagaactta gaacctcgct ggaaaggacc      5160
ctacaccgtc ctgctgacaa cccccaccgc tctcaaagta gacggcatct ctgcgtggat      5220
acacgccgct cacgtaaagg cggcgacggg acgggagaca ggctgctaaa cctggtagaa      5280
ggagcctacc tagccctcaa cctcaccagt cccgacaaaa cccaagagtg ctggctgtgt      5340
ctagtatcgg gaccccccta ctacgaaggg gtggccgtcc taggtactta ctccaaccat      5400
acctctgccc cggctaactg ctccgtgacc tcccaacaca agctgaccct gtccgaagtg      5460
accgggcagg gactctgcat aggagcagtt cccaaaaccc atcaggccct gtgtaatacc      5520
acccagaaga cgacgacgg gtcctactat ttggcctctc ccgccgggac catttgggct      5580
tgcagcaccg ggctcactcc ctgtctatct actactgtgc ttaacttaac cactgattac      5640
```

-continued

```
tgtgtcctgg ttgaactctg gccaaaggta acctaccact cccctaatta tgtttatggc    5700
cagtttgaaa agaaaactaa atataaaaga gagccggtgt cattaactct ggccctgctg    5760
ttgggaggac ttactatggg cggcatagct gcaggagttg aacagggac tacagccta     5820 gtggccacca acaattcga gcagctccag gcagccatac atacgacct tggggcctta     5880 gaaaaatcag tcagtgccct agaaaagtct ctgacctcgt tgtctgaggt ggtcctacag    5940
aaccggaggg gattagatct actgttccta aagaaggag gattatgtgc tgccctaaaa    6000
gaagaatgct gttttacgc ggaccacact ggcgtagtaa gagatagcat ggcaaagcta    6060
agagaaaggt taaccagag acaaaaattg ttcgaatcag acaagggtg gtttgaggga     6120 ctgtttaaca ggtccccatg gttcacgacc ctgatatcca ccattatggg ccctctgata    6180
gtacttttat taatcctact cttcggaccc tgtattctca accgcttggt ccagtttgta    6240
aaagacagaa tttcggtagt gcaggccctg ttctgaccc aacagtatca ccaactcaaa     6300
tcaatagatc cagaagaagt ggaatcacgt gaataaaaga ttttattcag tttccagaaa    6360 gagggggaa tgaaagaccc caccataagg cttagcacgc tagctacagt aacgccattt     6420
tgcaaggcat ggaaaagtac cagagctgag ttctcaaaag ttacaaggaa gtttaattaa    6480
agaataaggc tgaataacac tgggacaggg gccaaacagg atatctgtag tcaggcacct    6540 gggcccggc tcagggccaa gaacagatgg gcgccagtca tccgatagac tgagtcgccc    6600
gggtacccgt gttcccaata aagccttttg ctgtttgcat ccgaagcgtg gcctcgctgt    6660
tccttgggag ggtctcctca gagtgattga ctacccagct cgggggtctt tcatttgggg    6720
gctcgtccgg gattcggaga ccccgccca gggaccaccg acccaccgtc gggaggtaag    6780
ccggccgggc caaacaggat atctgtagtc aggcacctgg gccccggctc agggccaaga    6840
acagatggtc ctcagataaa gcgaaactaa caacagtttc tggaaagtcc cacctcagtt    6900
tcaagttccc caaaagaccg ggaaataccc caagccttat ttaaactaac caatcagctc    6960
gcttctcgct tctgtacccg cgcttttttgc tccccagtcc tagccctata aaaagggggt    7020
aagaactcca cactcggcgc gccagtcatc cgatagactg agtcgcccgg gtacccgtgt    7080
tcccaataaa gccttttgct gtttgca                                         7107
```

```
<210> SEQ ID NO 28
<211> LENGTH: 20
<212> TYPE: DNA
<213> ORGANISM: Artificial Sequence
<220> FEATURE:
<223> OTHER INFORMATION: XMRV Primer

<400> SEQUENCE: 28
aggtaggaac cacctagtcc                                                    20

<210> SEQ ID NO 29
<211> LENGTH: 20
<212> TYPE: DNA
<213> ORGANISM: Artificial Sequence
<220> FEATURE:
<223> OTHER INFORMATION: XMRV Primer

<400> SEQUENCE: 29
agggtcataa ggagtgtacc                                                    20

<210> SEQ ID NO 30
<211> LENGTH: 20
<212> TYPE: DNA
```

```
<213> ORGANISM: Artificial Sequence
<220> FEATURE:
<223> OTHER INFORMATION: XMRV Primer

<400> SEQUENCE: 30
aggtaggaac cacctagtcc                                               20

<210> SEQ ID NO 31
<211> LENGTH: 20
<212> TYPE: DNA
<213> ORGANISM: Artificial Sequence
<220> FEATURE:
<223> OTHER INFORMATION: XMRV Primer

<400> SEQUENCE: 31
ggagtgtacc tgcgataggc                                               20

<210> SEQ ID NO 32
<211> LENGTH: 20
<212> TYPE: DNA
<213> ORGANISM: Artificial Sequence
<220> FEATURE:
<223> OTHER INFORMATION: XMRV Primer

<400> SEQUENCE: 32
aggtaggaac cacctagtcc                                               20

<210> SEQ ID NO 33
<211> LENGTH: 20
<212> TYPE: DNA
<213> ORGANISM: Artificial Sequence
<220> FEATURE:
<223> OTHER INFORMATION: XMRV Primer

<400> SEQUENCE: 33
gtttcttgcc ctgggtcctc                                               20

<210> SEQ ID NO 34
<211> LENGTH: 20
<212> TYPE: DNA
<213> ORGANISM: Artificial Sequence
<220> FEATURE:
<223> OTHER INFORMATION: XMRV Primer

<400> SEQUENCE: 34
aggtaggaac cacctagtcc                                               20

<210> SEQ ID NO 35
<211> LENGTH: 20
<212> TYPE: DNA
<213> ORGANISM: Artificial Sequence
<220> FEATURE:
<223> OTHER INFORMATION: XMRV Primer

<400> SEQUENCE: 35
ctgggtcctc agggtcataa                                               20

<210> SEQ ID NO 36
<211> LENGTH: 20
<212> TYPE: DNA
<213> ORGANISM: Artificial Sequence
<220> FEATURE:
<223> OTHER INFORMATION: XMRV Primer

<400> SEQUENCE: 36
aggtaggaac cacctagtcc                                               20
```

<210> SEQ ID NO 37
<211> LENGTH: 20
<212> TYPE: DNA
<213> ORGANISM: Artificial Sequence
<220> FEATURE:
<223> OTHER INFORMATION: XMRV Primer

<400> SEQUENCE: 37
cataaggagt gtacctgcga                                              20

<210> SEQ ID NO 38
<211> LENGTH: 20
<212> TYPE: DNA
<213> ORGANISM: Artificial Sequence
<220> FEATURE:
<223> OTHER INFORMATION: XMRV Primer

<400> SEQUENCE: 38
tcgcaggtac actccttatg                                              20

<210> SEQ ID NO 39
<211> LENGTH: 20
<212> TYPE: DNA
<213> ORGANISM: Artificial Sequence
<220> FEATURE:
<223> OTHER INFORMATION: XMRV Primer

<400> SEQUENCE: 39
tctctttctt ccggggtttc                                              20

<210> SEQ ID NO 40
<211> LENGTH: 20
<212> TYPE: DNA
<213> ORGANISM: Artificial Sequence
<220> FEATURE:
<223> OTHER INFORMATION: XMRV Primer

<400> SEQUENCE: 40
tcgcaggtac actccttatg                                              20

<210> SEQ ID NO 41
<211> LENGTH: 20
<212> TYPE: DNA
<213> ORGANISM: Artificial Sequence
<220> FEATURE:
<223> OTHER INFORMATION: XMRV Primer

<400> SEQUENCE: 41
tttctctcct gatacgttcc                                              20

<210> SEQ ID NO 42
<211> LENGTH: 20
<212> TYPE: DNA
<213> ORGANISM: Artificial Sequence
<220> FEATURE:
<223> OTHER INFORMATION: XMRV Primer

<400> SEQUENCE: 42
tcgcaggtac actccttatg                                              20

<210> SEQ ID NO 43
<211> LENGTH: 20
<212> TYPE: DNA
<213> ORGANISM: Artificial Sequence
<220> FEATURE:

```
<223> OTHER INFORMATION: XMRV Primer

<400> SEQUENCE: 43
gttcctctct ttcttccggg                                           20

<210> SEQ ID NO 44
<211> LENGTH: 20
<212> TYPE: DNA
<213> ORGANISM: Artificial Sequence
<220> FEATURE:
<223> OTHER INFORMATION: XMRV Primer

<400> SEQUENCE: 44
gcctatcgca ggtacactcc                                           20

<210> SEQ ID NO 45
<211> LENGTH: 20
<212> TYPE: DNA
<213> ORGANISM: Artificial Sequence
<220> FEATURE:
<223> OTHER INFORMATION: XMRV Primer

<400> SEQUENCE: 45
tctctttctt ccggggtttc                                           20

<210> SEQ ID NO 46
<211> LENGTH: 20
<212> TYPE: DNA
<213> ORGANISM: Artificial Sequence
<220> FEATURE:
<223> OTHER INFORMATION: XMRV Primer

<400> SEQUENCE: 46
gcctatcgca ggtacactcc                                           20

<210> SEQ ID NO 47
<211> LENGTH: 20
<212> TYPE: DNA
<213> ORGANISM: Artificial Sequence
<220> FEATURE:
<223> OTHER INFORMATION: XMRV Primer

<400> SEQUENCE: 47
gttcctctct ttcttccggg                                           20

<210> SEQ ID NO 48
<211> LENGTH: 20
<212> TYPE: DNA
<213> ORGANISM: Artificial Sequence
<220> FEATURE:
<223> OTHER INFORMATION: XMRV Primer

<400> SEQUENCE: 48
tcgcaggtac actccttatg                                           20

<210> SEQ ID NO 49
<211> LENGTH: 20
<212> TYPE: DNA
<213> ORGANISM: Artificial Sequence
<220> FEATURE:
<223> OTHER INFORMATION: XMRV Primer

<400> SEQUENCE: 49
ctcctgatac gttcctctct                                           20
```

```
<210> SEQ ID NO 50
<211> LENGTH: 20
<212> TYPE: DNA
<213> ORGANISM: Artificial Sequence
<220> FEATURE:
<223> OTHER INFORMATION: XMRV Primer

<400> SEQUENCE: 50
ttatgaccct gaggacccag                                               20

<210> SEQ ID NO 51
<211> LENGTH: 20
<212> TYPE: DNA
<213> ORGANISM: Artificial Sequence
<220> FEATURE:
<223> OTHER INFORMATION: XMRV Primer

<400> SEQUENCE: 51
tctctttctt ccggggtttc                                               20

<210> SEQ ID NO 52
<211> LENGTH: 20
<212> TYPE: DNA
<213> ORGANISM: Artificial Sequence
<220> FEATURE:
<223> OTHER INFORMATION: XMRV Primer

<400> SEQUENCE: 52
ttatgaccct gaggacccag                                               20

<210> SEQ ID NO 53
<211> LENGTH: 20
<212> TYPE: DNA
<213> ORGANISM: Artificial Sequence
<220> FEATURE:
<223> OTHER INFORMATION: XMRV Primer

<400> SEQUENCE: 53
tttctctcct gatacgttcc                                               20

<210> SEQ ID NO 54
<211> LENGTH: 20
<212> TYPE: DNA
<213> ORGANISM: Artificial Sequence
<220> FEATURE:
<223> OTHER INFORMATION: XMRV Primer

<400> SEQUENCE: 54
ggtacactcc ttatgaccct                                               20

<210> SEQ ID NO 55
<211> LENGTH: 20
<212> TYPE: DNA
<213> ORGANISM: Artificial Sequence
<220> FEATURE:
<223> OTHER INFORMATION: XMRV Primer

<400> SEQUENCE: 55
tttctctcct gatacgttcc                                               20

<210> SEQ ID NO 56
<211> LENGTH: 20
<212> TYPE: DNA
<213> ORGANISM: Artificial Sequence
<220> FEATURE:
<223> OTHER INFORMATION: XMRV Primer
```

```
<400> SEQUENCE: 56
ttatgaccct gaggacccag                                              20

<210> SEQ ID NO 57
<211> LENGTH: 20
<212> TYPE: DNA
<213> ORGANISM: Artificial Sequence
<220> FEATURE:
<223> OTHER INFORMATION: XMRV Primer

<400> SEQUENCE: 57
gttcctctct ttcttccggg                                              20
```